United States Patent
Wei et al.

(10) Patent No.: US 11,672,430 B2
(45) Date of Patent: Jun. 13, 2023

(54) SYSTEM AND METHOD FOR HEALTH MONITORING

(71) Applicant: VITA-COURSE TECHNOLOGIES CO., LTD., Guangdong (CN)

(72) Inventors: Chuanmin Wei, Shenzhen (CN); Zhiyong Wang, Shenzhen (CN); Jiao Yu, Shenzhen (CN); Jiwei Zhao, Shenzhen (CN); Zhiqiang Lv, Shenzhen (CN)

(73) Assignee: VITA-COURSE TECHNOLOGIES CO., LTD., Shenzhen (CN)

( * ) Notice: Subject to any disclaimer, the term of this patent is extended or adjusted under 35 U.S.C. 154(b) by 387 days.

(21) Appl. No.: 16/914,466

(22) Filed: Jun. 28, 2020

(65) Prior Publication Data

US 2020/0359908 A1    Nov. 19, 2020

Related U.S. Application Data

(63) Continuation of application No. 15/537,377, filed as application No. PCT/CN2016/070017 on Jan. 4, 2016, now abandoned.

(30) Foreign Application Priority Data

Jan. 4, 2015 (CN) .......................... 201510005387.4
Mar. 31, 2015 (CN) .......................... 201520186879.3
(Continued)

(51) Int. Cl.
*A61B 5/0205* (2006.01)
*A61B 5/01* (2006.01)
(Continued)

(52) U.S. Cl.
CPC .......... *A61B 5/0205* (2013.01); *A61B 5/0002* (2013.01); *A61B 5/0022* (2013.01);
(Continued)

(58) Field of Classification Search
CPC ....... A61B 5/0205; A61B 5/0022; A61B 5/01; A61B 5/021; A61B 5/318; A61B 5/681; A61B 5/7203; A61B 5/7282; G16H 50/20
See application file for complete search history.

(56) References Cited

U.S. PATENT DOCUMENTS 5,626,135 A * 5/1997 Sanfilippo ............ A61N 1/0492
600/394
5,873,834 A    2/1999 Yanagi et al.
(Continued)

FOREIGN PATENT DOCUMENTS

CN    1698535 A    11/2005
CN    1849998 A    10/2006
(Continued)

OTHER PUBLICATIONS

Extended European Search Report in European Application No. 17773043.9 dated Mar. 21, 2019, 8 pages.
(Continued)

*Primary Examiner* — Jonathan T Kuo
(74) *Attorney, Agent, or Firm* — Bay State IP, LLC

(57) ABSTRACT

The present disclosure relates to a device, method and system for estimating or monitoring the health condition of a subject. At least one processor, when executing instructions, may perform one or more of the following operations. At least one physiological signal or information including a physiological signal of a subject may be received. At least one physiological parameter of interest may be generated based on the physiological signal. The physiological parameter of interest may be analyzed according to an analysis model. A physiological result may be generated. A recommendation may be provided based on the physiological analysis result.

20 Claims, 28 Drawing Sheets

(30) Foreign Application Priority Data

| Mar. 31, 2015 | (CN) | 201520188127.0 |
| --- | --- | --- |
| Mar. 31, 2015 | (CN) | 201520188128.5 |
| Mar. 31, 2015 | (CN) | 201520188130.2 |
| Mar. 31, 2015 | (CN) | 201520188151.4 |
| Mar. 31, 2015 | (CN) | 201520188152.9 |
| Mar. 31, 2015 | (CN) | 201520188308.3 |
| Apr. 1, 2015 | (CN) | 201520192648.3 |
| Apr. 21, 2015 | (CN) | 201520242994.8 |
| Jun. 3, 2015 | (CN) | 201520377166.5 |
| Jul. 3, 2015 | (WO) | PCT/CN2015/083334 |
| Dec. 5, 2015 | (WO) | PCT/CN2015/096498 |

(51) Int. Cl.

| A61B 5/145 | (2006.01) |
| --- | --- |
| A61B 5/00 | (2006.01) |
| A61B 5/021 | (2006.01) |
| A61B 5/11 | (2006.01) |
| G16H 40/67 | (2018.01) |
| A61B 5/0537 | (2021.01) |
| A61B 5/16 | (2006.01) |
| A61B 5/318 | (2021.01) |
| G16H 50/50 | (2018.01) |
| G16H 50/20 | (2018.01) |
| A61B 5/024 | (2006.01) |

(52) U.S. Cl.
CPC ............... *A61B 5/01* (2013.01); *A61B 5/021* (2013.01); *A61B 5/0537* (2013.01); *A61B 5/1112* (2013.01); *A61B 5/14542* (2013.01); *A61B 5/165* (2013.01); *A61B 5/318* (2021.01); *A61B 5/486* (2013.01); *A61B 5/681* (2013.01); *A61B 5/6803* (2013.01); *A61B 5/6893* (2013.01); *A61B 5/6895* (2013.01); *A61B 5/6897* (2013.01); *A61B 5/6898* (2013.01); *A61B 5/7203* (2013.01); *A61B 5/7207* (2013.01); *A61B 5/7282* (2013.01); *G16H 40/67* (2018.01); *G16H 50/20* (2018.01); *G16H 50/50* (2018.01); *A61B 5/02405* (2013.01); *A61B 5/742* (2013.01); *A61B 2560/0209* (2013.01); *A61B 2562/0219* (2013.01); *A61B 2562/0233* (2013.01); *A61B 2562/0247* (2013.01); *A61B 2562/046* (2013.01)

(56) References Cited

U.S. PATENT DOCUMENTS

| 6,355,000 | B1 | 3/2002 | Ogura |
| --- | --- | --- | --- |
| 7,674,231 | B2 | 3/2010 | McCombie et al. |
| 7,887,491 | B2 | 2/2011 | Marks et al. |
| 8,313,439 | B2 | 11/2012 | McCombie et al. |
| 9,439,599 | B2 | 9/2016 | Thompson et al. |
| 9,865,176 | B2 | 1/2018 | Tran |
| 2002/0147402 | A1 | 10/2002 | Nitzan et al. |
| 2003/0167012 | A1 | 9/2003 | Friedman et al. |
| 2005/0208969 | A1 | 9/2005 | Kwoen |
| 2005/0261593 | A1 | 11/2005 | Zhang et al. |
| 2007/0100247 | A1* | 5/2007 | Platt ............... A61B 5/02233 600/490 |
| 2008/0039731 | A1 | 2/2008 | McCombie et al. |
| 2008/0221461 | A1 | 9/2008 | Zhou et al. |
| 2009/0018422 | A1 | 1/2009 | Banet et al. |
| 2009/0105605 | A1* | 4/2009 | Abreu ............... A61B 5/4076 600/549 |
| 2009/0273467 | A1 | 11/2009 | Elixmann et al. |
| 2010/0049006 | A1 | 2/2010 | Magar et al. |
| 2010/0087743 | A1 | 4/2010 | Hatib et al. |
| 2010/0160798 | A1 | 6/2010 | Banet et al. |
| 2011/0009718 | A1 | 1/2011 | Gavish |
| 2011/0066045 | A1* | 3/2011 | Moon ............... A61B 5/021 600/485 |
| 2011/0231152 | A1 | 9/2011 | Kawabe |
| 2012/0101350 | A1 | 4/2012 | Bychkov |
| 2012/0136261 | A1 | 5/2012 | Sethi et al. |
| 2012/0316448 | A1 | 12/2012 | Gu et al. |
| 2013/0012823 | A1 | 1/2013 | Ripoll et al. |
| 2013/0053655 | A1 | 2/2013 | Castellanos |
| 2013/0116534 | A1 | 5/2013 | Woo |
| 2013/0197369 | A1 | 8/2013 | Xiang |
| 2014/0066788 | A1 | 3/2014 | Mukkamala et al. |
| 2014/0206976 | A1* | 7/2014 | Thompson ............ G16Z 99/00 600/391 |
| 2015/0018637 | A1 | 1/2015 | Chen et al. |
| 2015/0125832 | A1* | 5/2015 | Tran .................... G09B 5/00 434/127 |
| 2015/0313486 | A1 | 11/2015 | Mestha et al. |
| 2015/0320359 | A1 | 11/2015 | Luo |
| 2015/0374244 | A1 | 12/2015 | Yoo et al. |
| 2015/0377909 | A1 | 12/2015 | Cavet et al. |
| 2016/0270708 | A1 | 9/2016 | Tateda et al. |
| 2017/0109495 | A1 | 4/2017 | Xin |

FOREIGN PATENT DOCUMENTS

| CN | 101327121 A | 12/2008 |
| --- | --- | --- |
| CN | 101524270 A | 9/2009 |
| CN | 101732040 A | 6/2010 |
| CN | 101810470 A | 8/2010 |
| CN | 102008296 A | 4/2011 |
| CN | 102397064 A | 4/2012 |
| CN | 102429649 A | 5/2012 |
| CN | 102488503 A | 6/2012 |
| CN | 202505340 U | 10/2012 |
| CN | 103190891 A | 7/2013 |
| CN | 103385702 A | 11/2013 |
| CN | 103462598 A | 12/2013 |
| CN | 103598876 A | 2/2014 |
| CN | 103637787 A | 3/2014 |
| CN | 103637788 A | 3/2014 |
| CN | 104173036 A | 12/2014 |
| CN | 204044771 U | 12/2014 |
| CN | 104257371 A | 1/2015 |
| CN | 104323764 A | 2/2015 |
| CN | 104382571 A | 3/2015 |
| CN | 104414626 A | 3/2015 |
| CN | 204207743 A | 3/2015 |
| CN | 104523252 A | 4/2015 |
| CN | 104665768 A | 6/2015 |
| CN | 104706348 A | 6/2015 |
| CN | 104720773 A | 6/2015 |
| CN | 204499693 U | 7/2015 |
| CN | 204506976 U | 7/2015 |
| CN | 104814729 A | 8/2015 |
| CN | 204674751 U | 9/2015 |
| WO | 2007110158 A1 | 10/2007 |
| WO | 2010135516 A2 | 11/2010 |
| WO | 2011008383 A1 | 1/2011 |
| WO | 2012040931 A1 | 4/2012 |
| WO | 2012128407 A1 | 9/2012 |
| WO | 2013171599 A1 | 11/2013 |
| WO | 2014199578 A1 | 12/2014 |
| WO | 2016155138 A1 | 10/2016 |
| WO | 2016155348 A1 | 10/2016 |
| WO | 2017005016 A1 | 1/2017 |

OTHER PUBLICATIONS

International Search Report in PCT/CN2016/077469 dated Jun. 8, 2016, 5 pages.
Written Opinion in PCT/CN2016/077469 dated June 8, 2016, 4 pages.
International Search Report in PCT/CN2017/076702 dated Jun. 7, 2017, 5 pages.
Written Opinion in PCT/CN2017/076702 dated Jun. 7, 2017, 5 pages.

(56) References Cited

OTHER PUBLICATIONS

The Second Office Action in Chinese Application No. 201580078735.9 dated Mar. 16, 2020, 25 pages.
Nth Office Action for Chinese Patent Application 201510005387.4 dated May 17, 2017, 20 pages.
International Search Report and Written Opinion for PCT/CN2016/070017 dated Apr. 13, 2016, 12 pages.
Search Report and First Office Action for Chinese Patent Application 201510005387.4 dated Apr. 25, 2016, 13 pages.
Nth Office Action for Chinese Patent Application 201510005387.4 dated Dec. 15, 2016, 12 pages.
International Search Report and Witten Opinion for PCT/CN2015/083334 dated Dec. 18, 2015, 11 pages.
International Search Report and Written Opinion for PCT/CN2015/096498 dated Mar. 9, 2016, 10 pages.

* cited by examiner

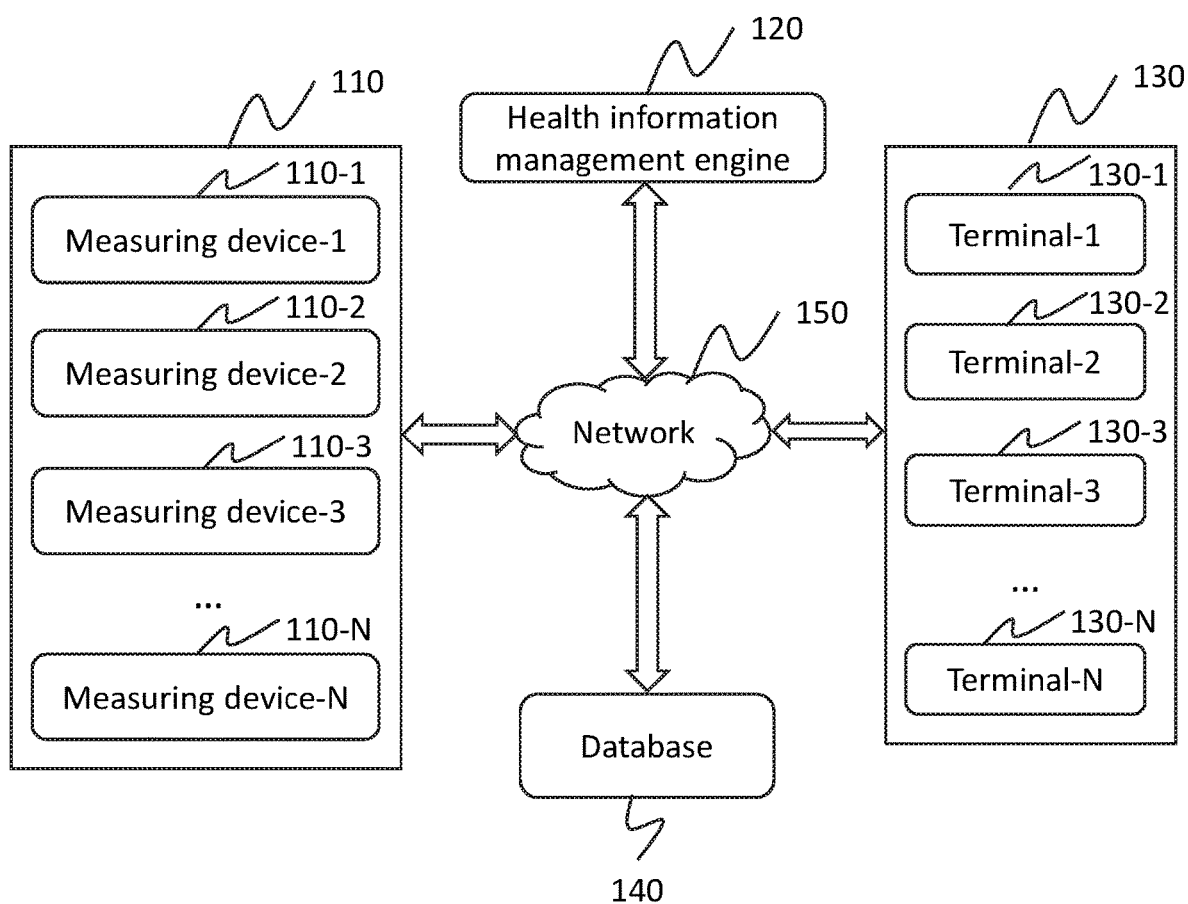
FIG. 1-A

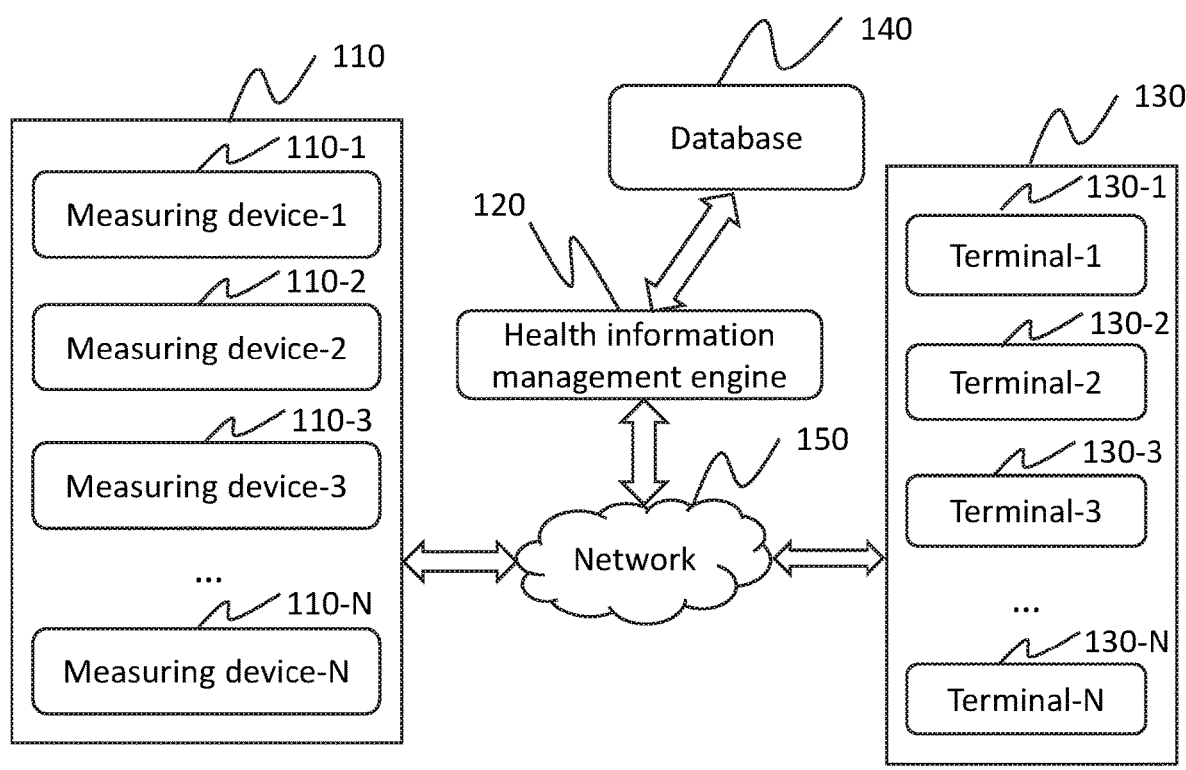
FIG. 1-B

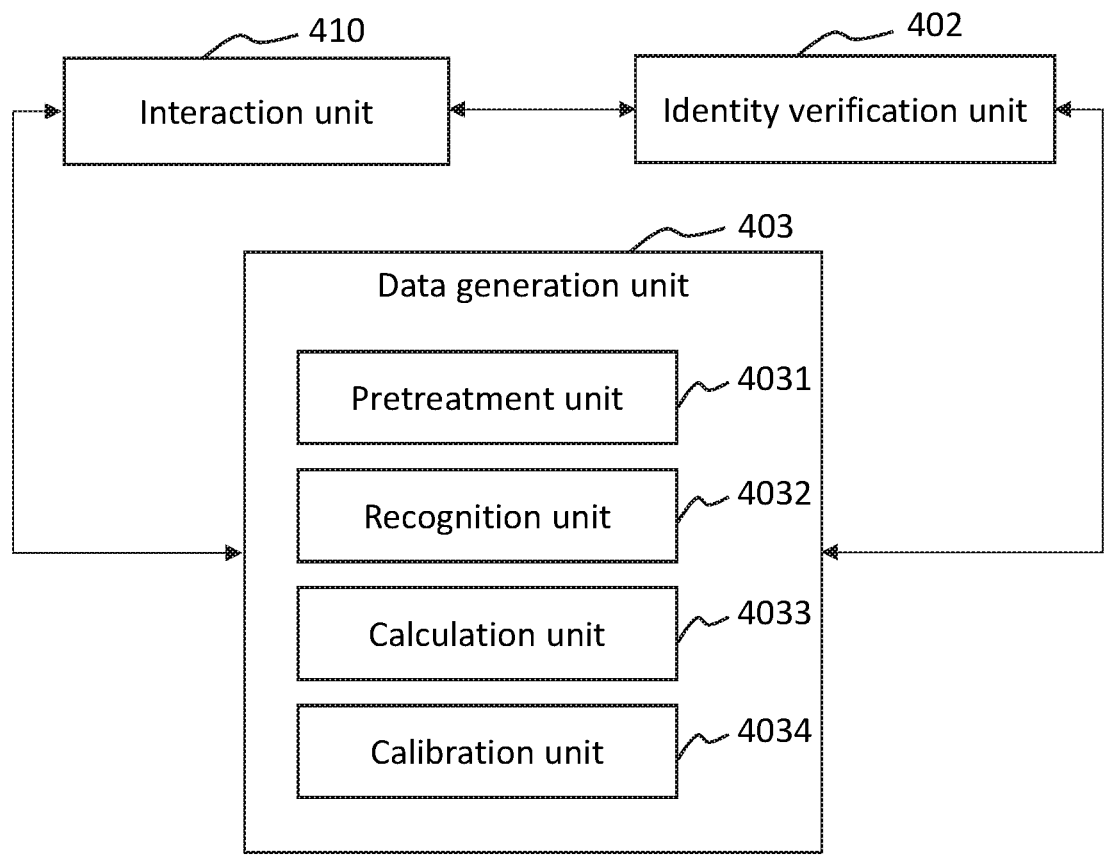
FIG. 4-A
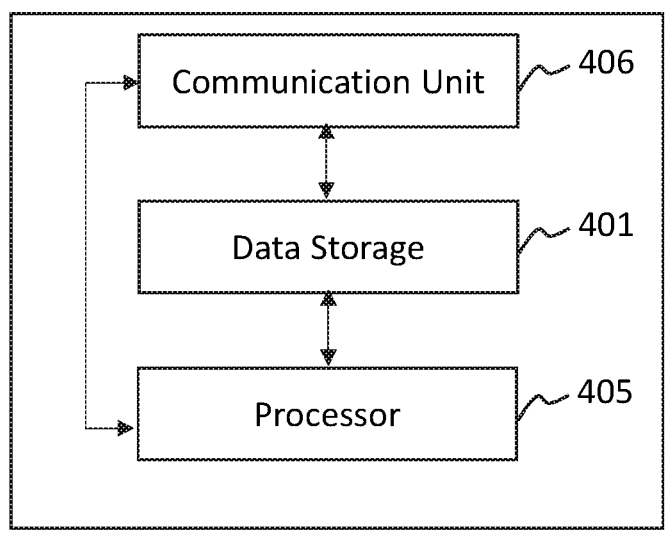
FIG. 4-B

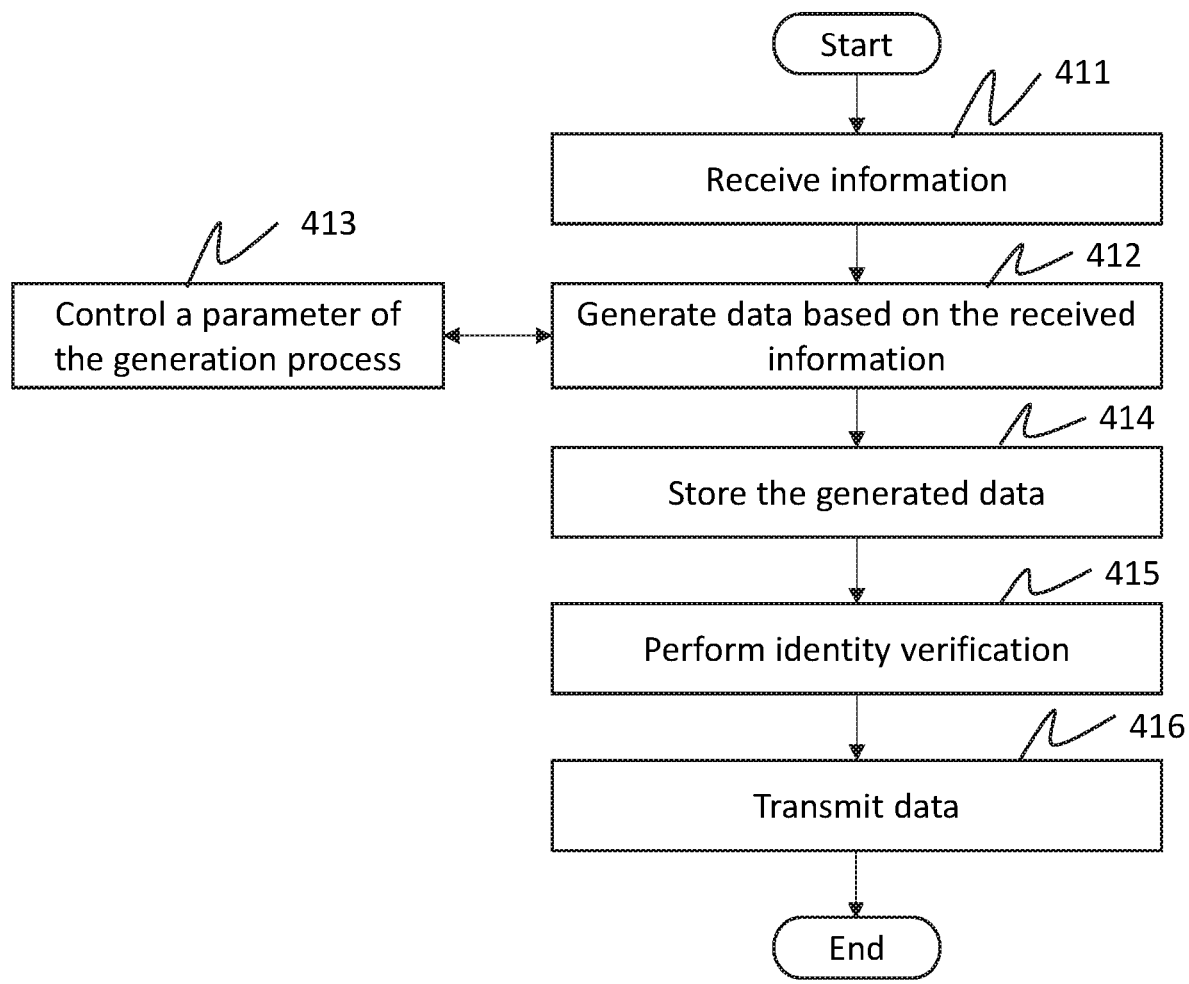
FIG. 4-C

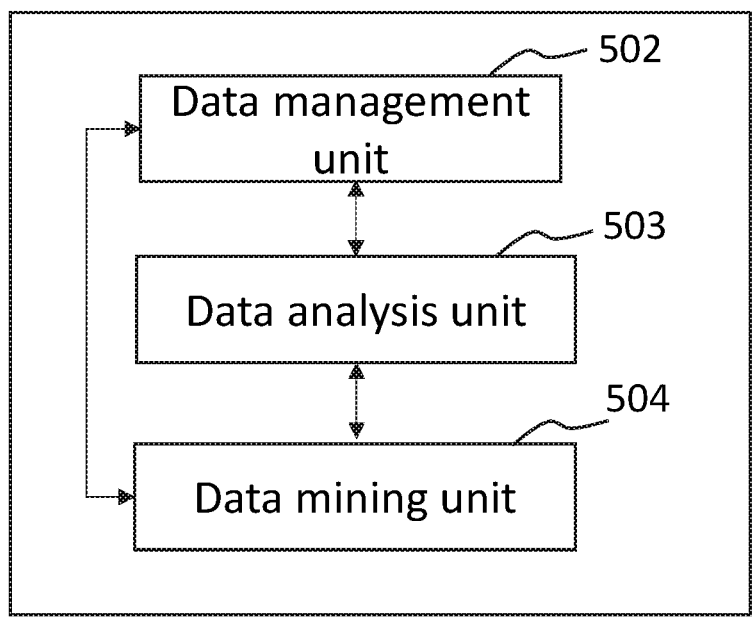
FIG. 5-A
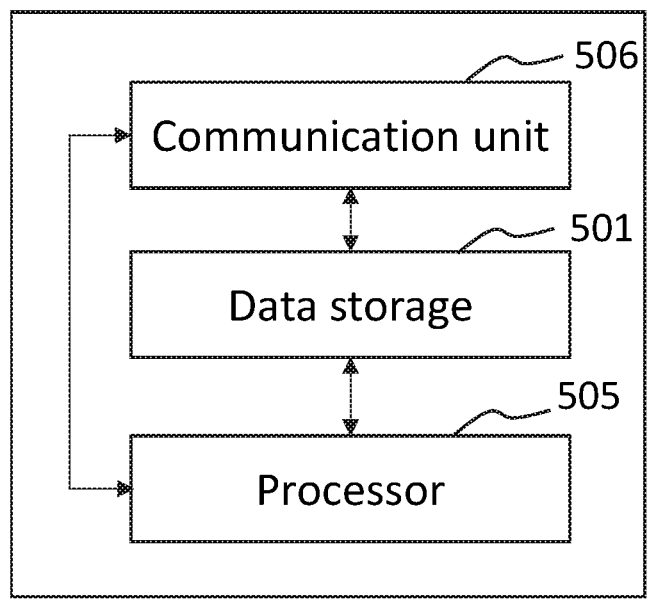
FIG. 5-B

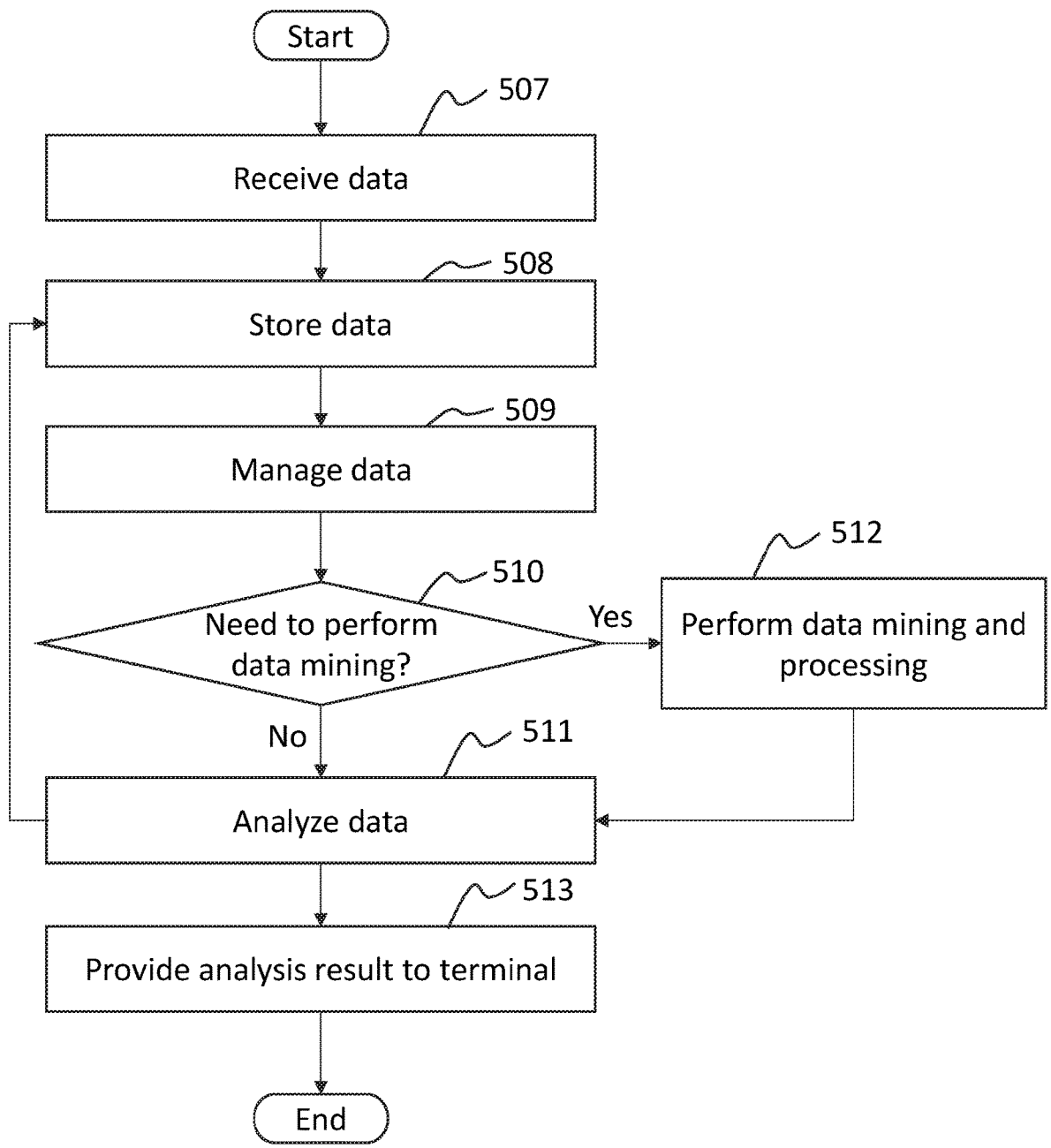
FIG. 5-C

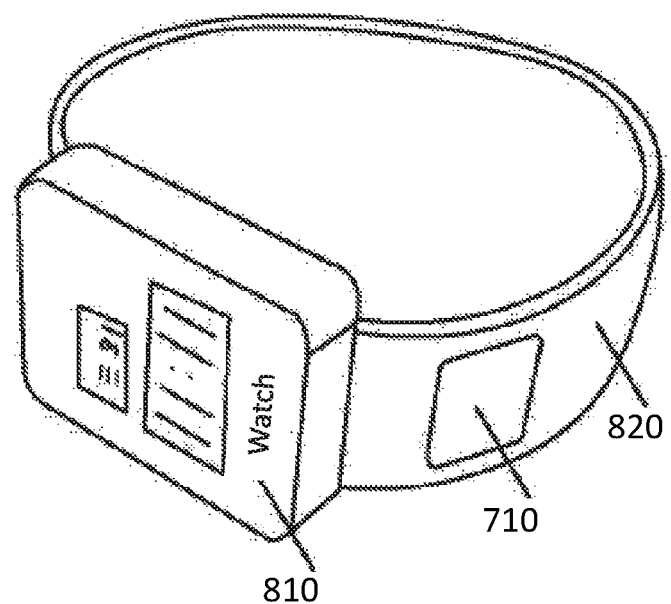
FIG. 8-A
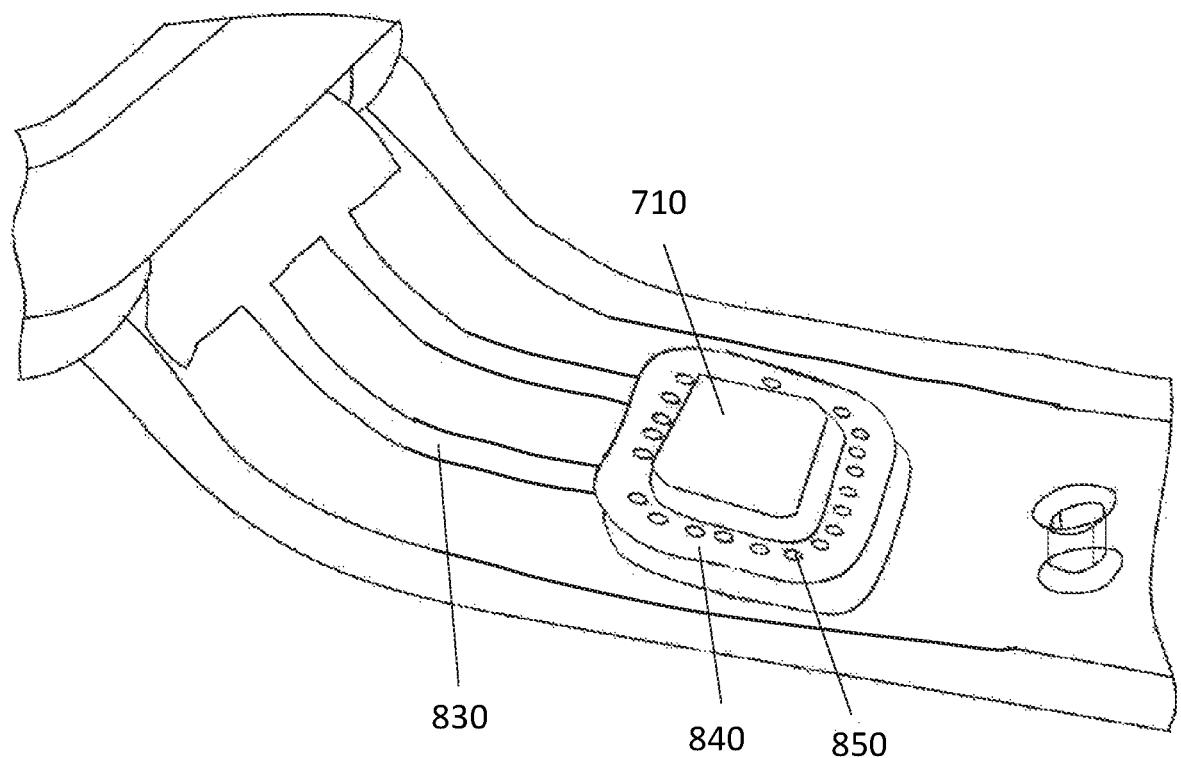
FIG. 8-B

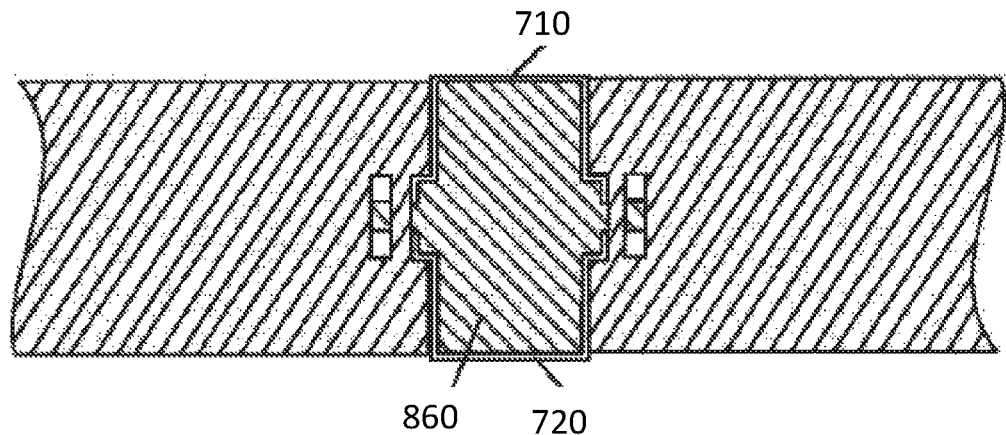
FIG. 8-C
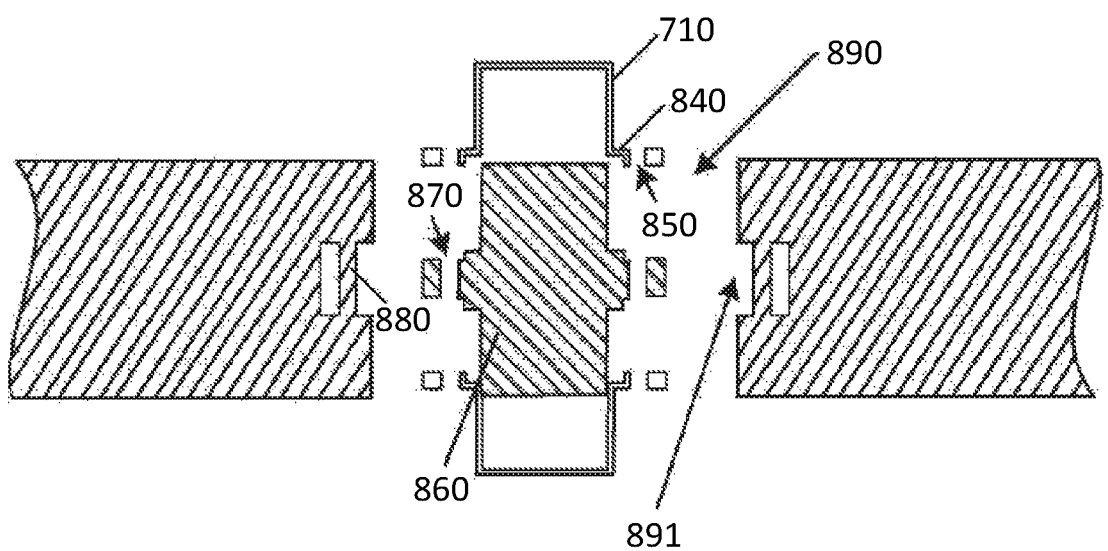
FIG. 8-D

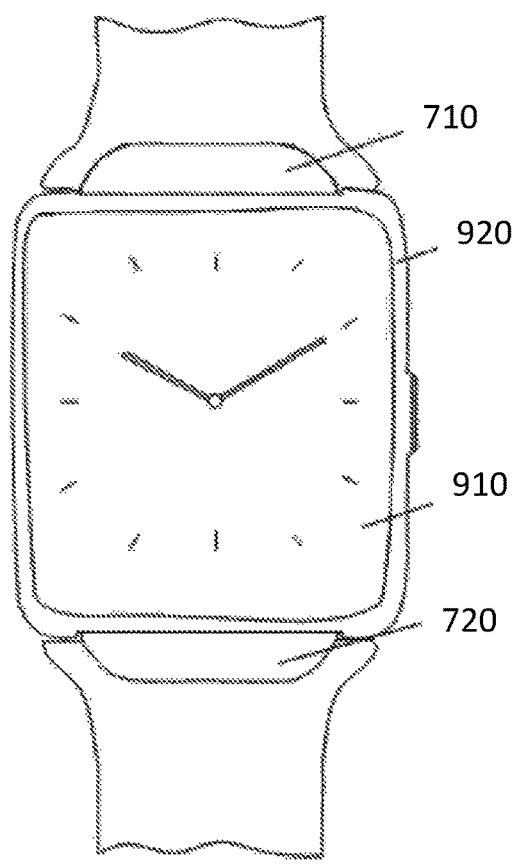
FIG. 9-A
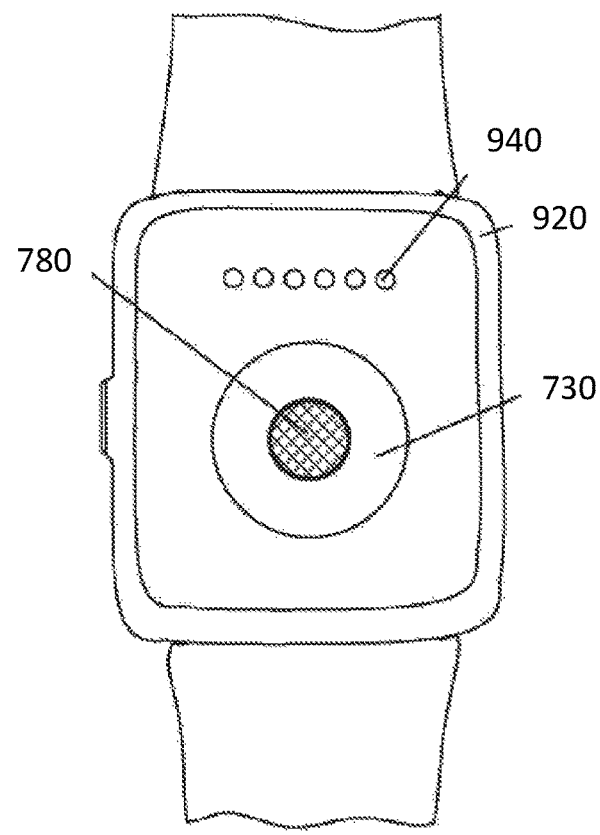
FIG. 9-B

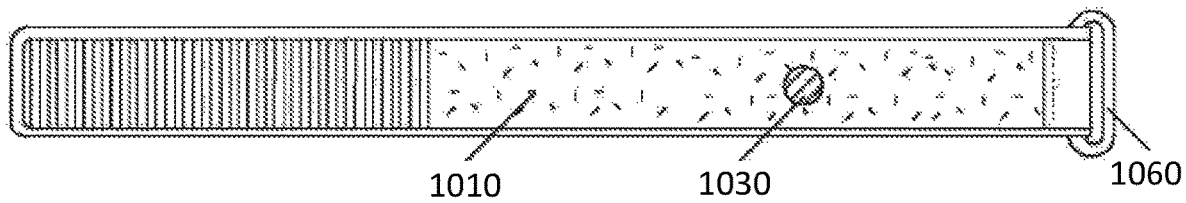
FIG. 10-A
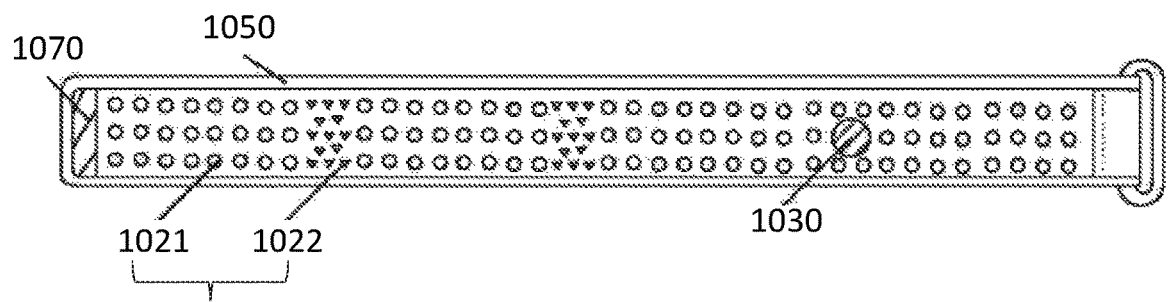
FIG. 10-B
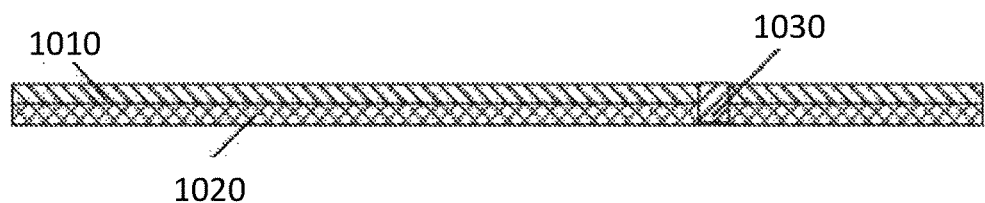
FIG. 10-C

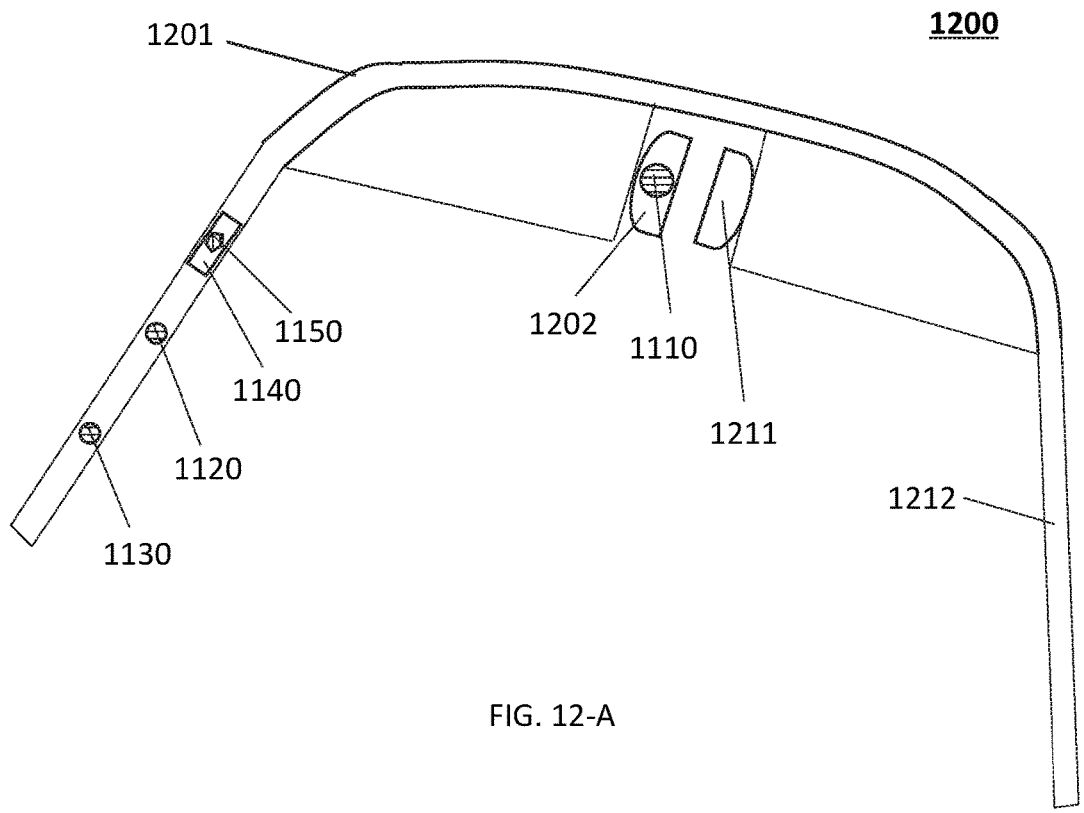
FIG. 12-A
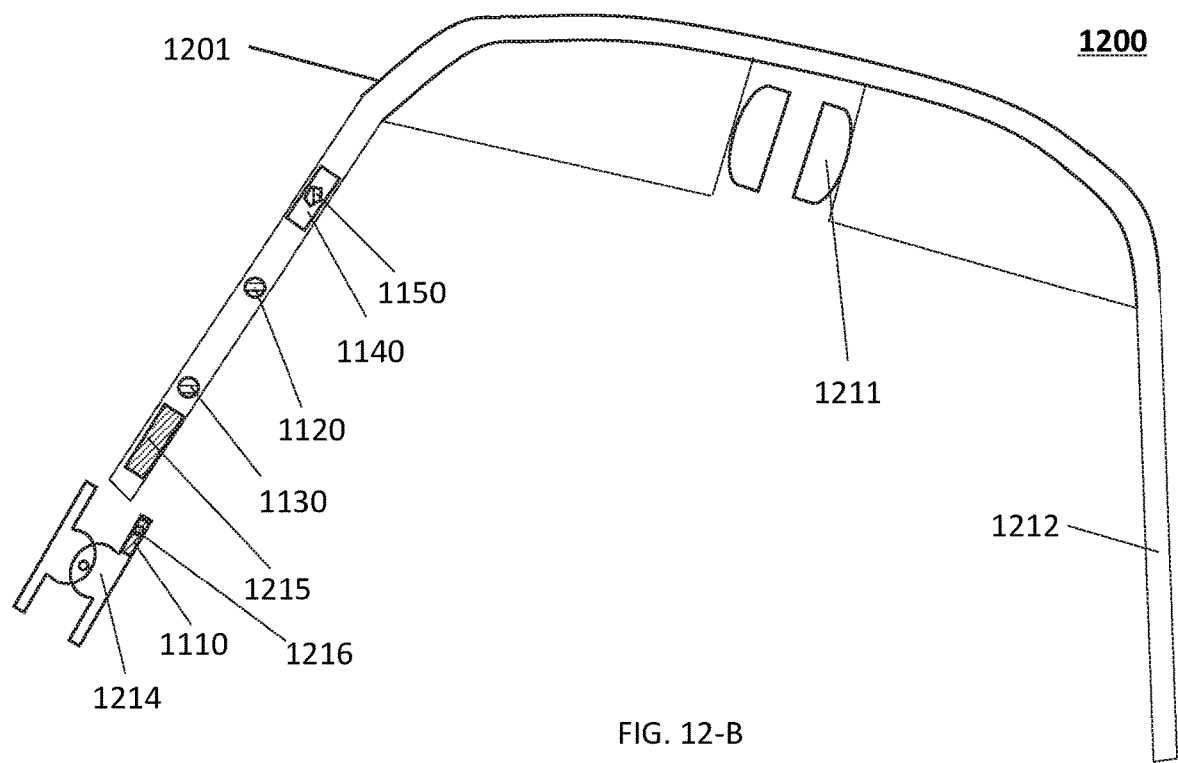
FIG. 12-B

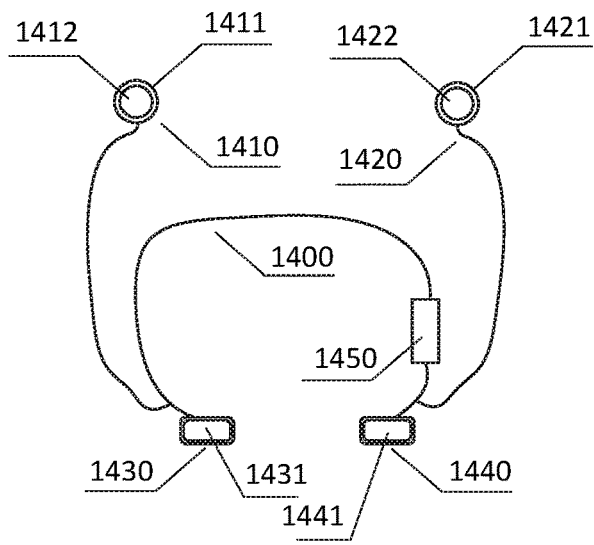
FIG. 14-A
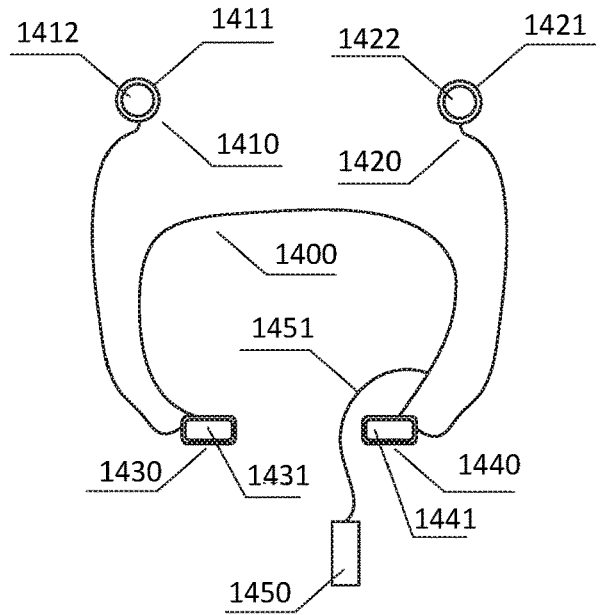
FIG. 14-B
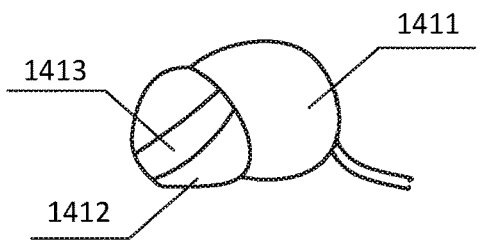
FIG. 14-C

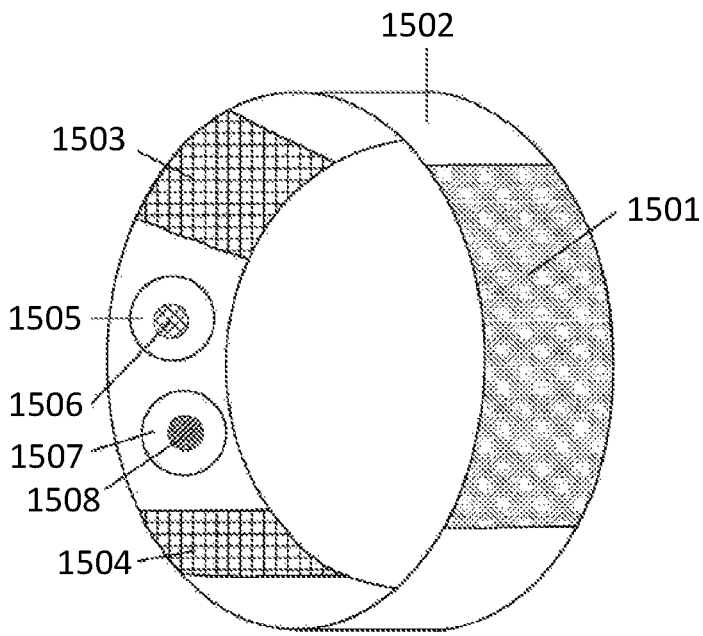
FIG. 15-A
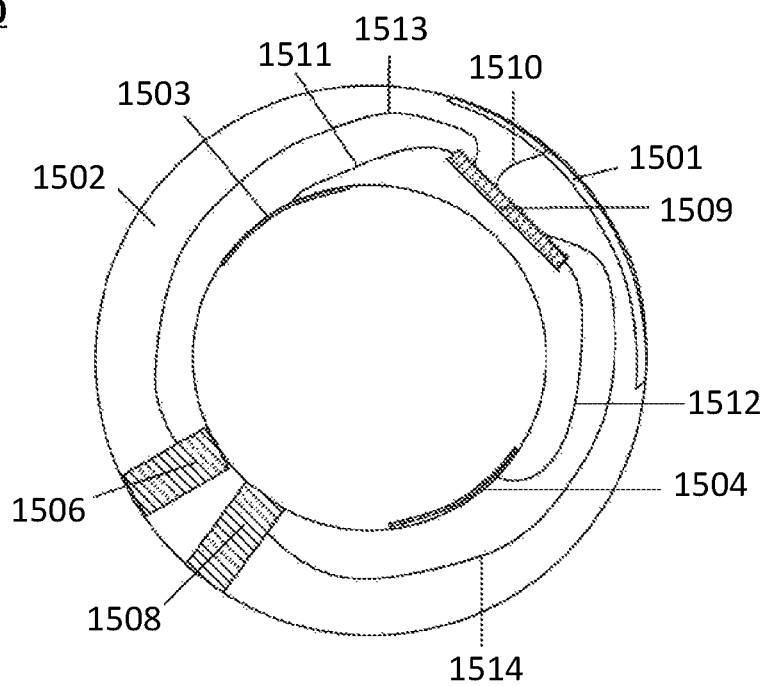
FIG. 15-B

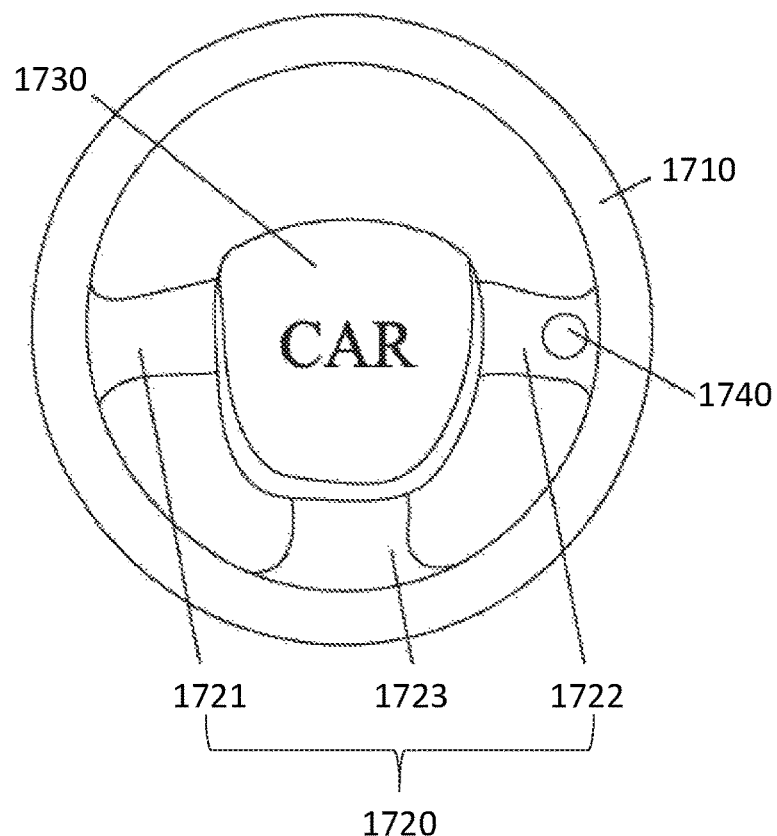
FIG. 17-A
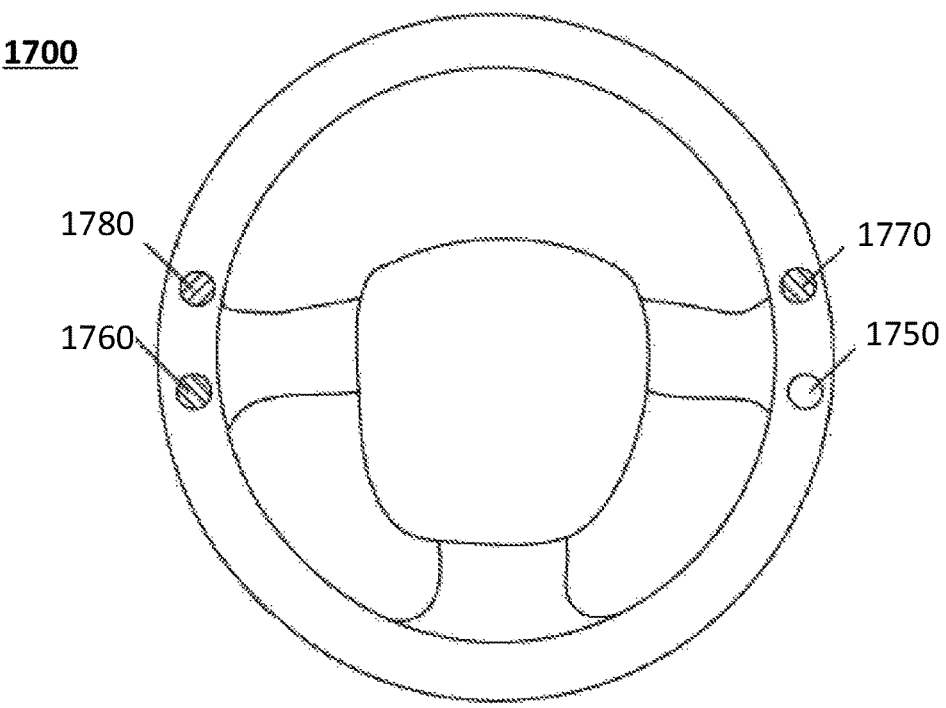
FIG. 17-B

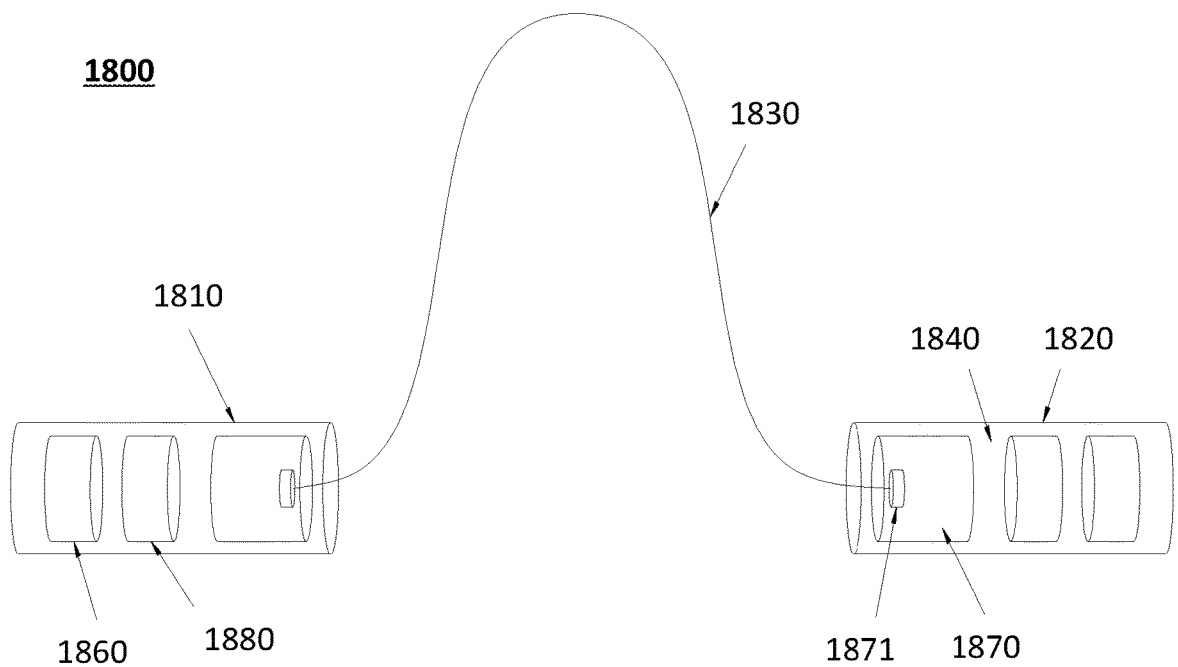
FIG. 18-A
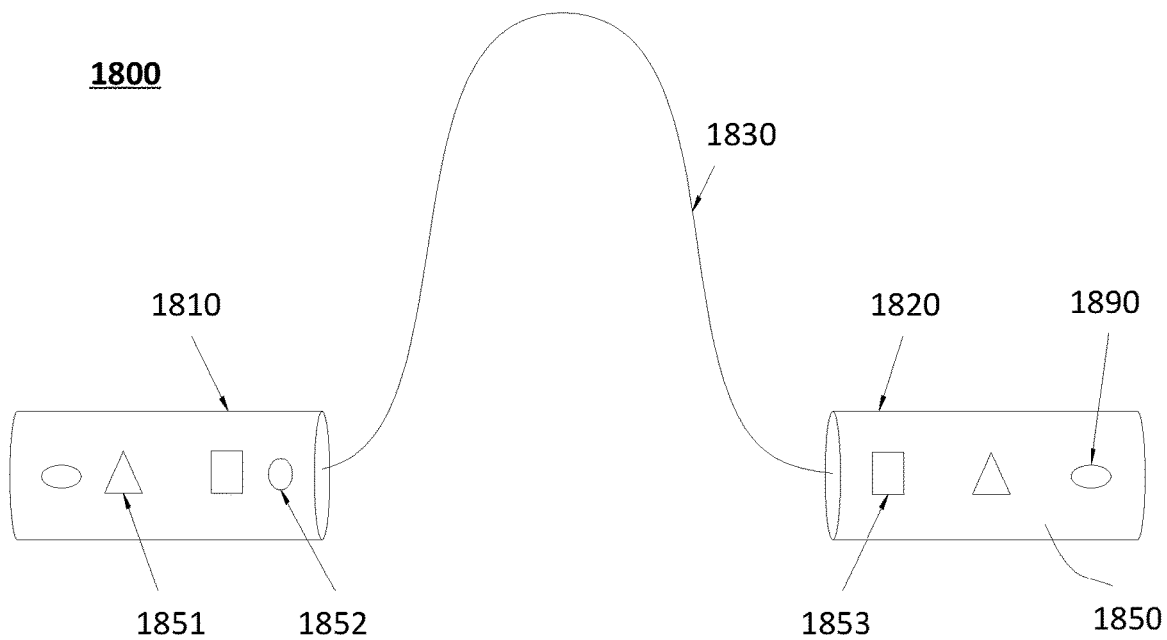
FIG. 18-B

1900
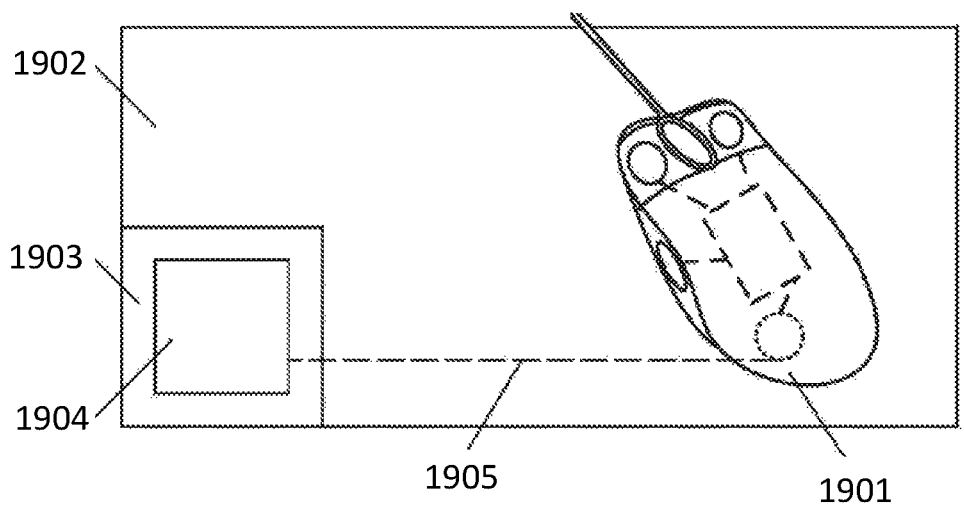
FIG. 19-A
1901
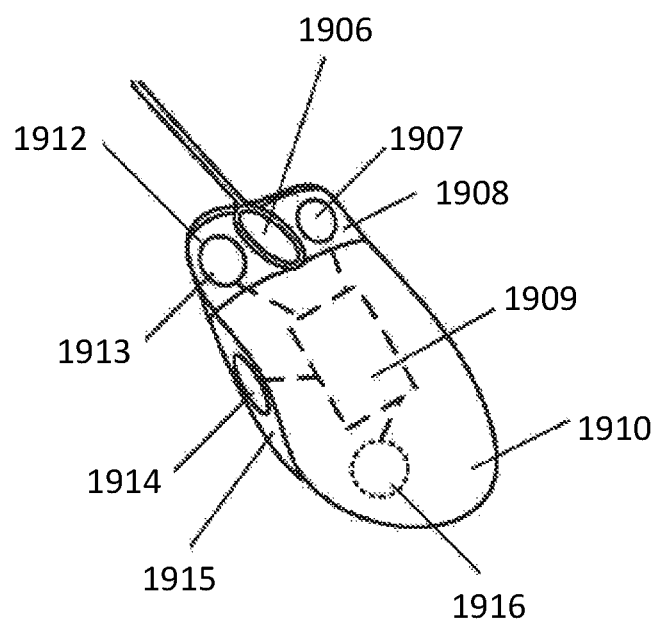
FIG. 19-B

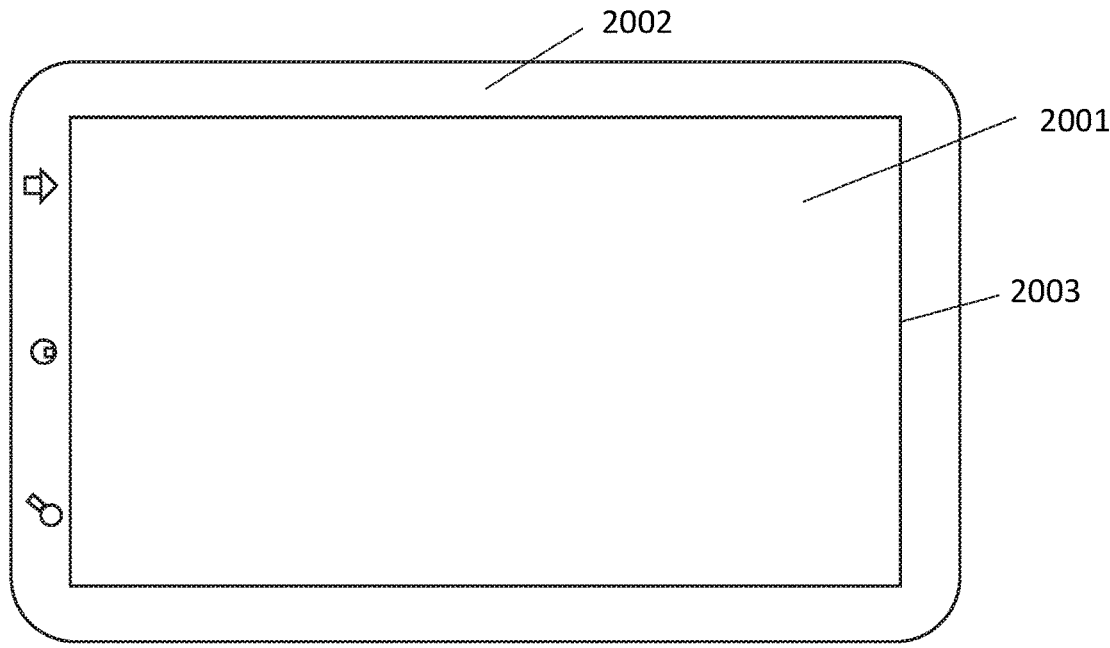
FIG. 20-A
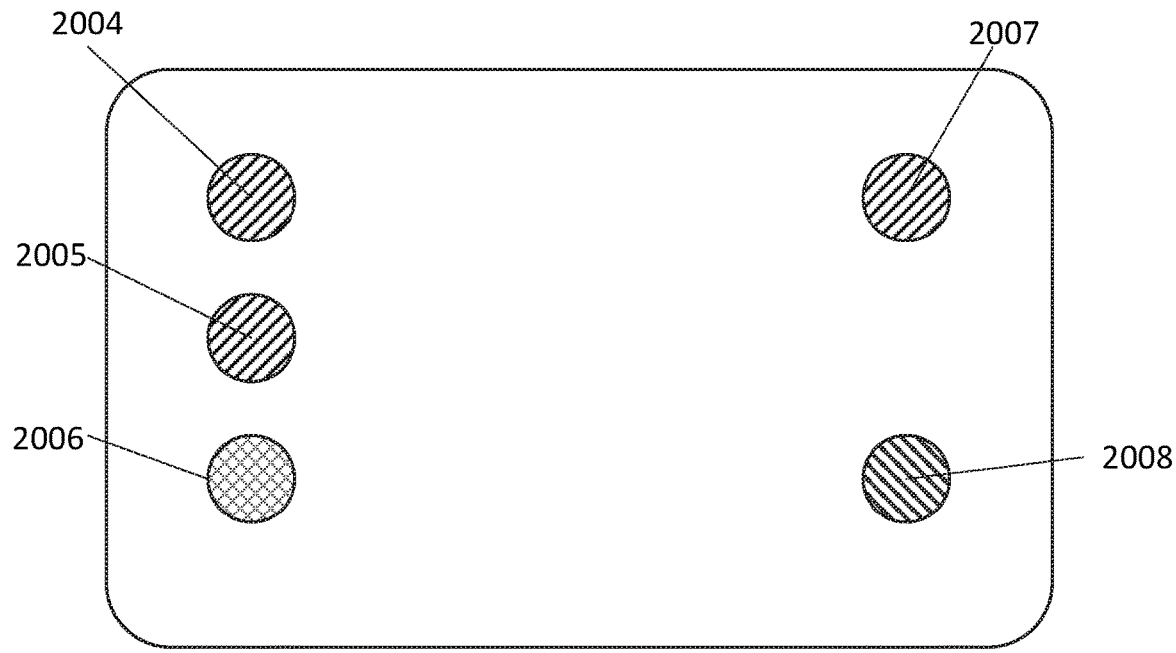
FIG. 20-B

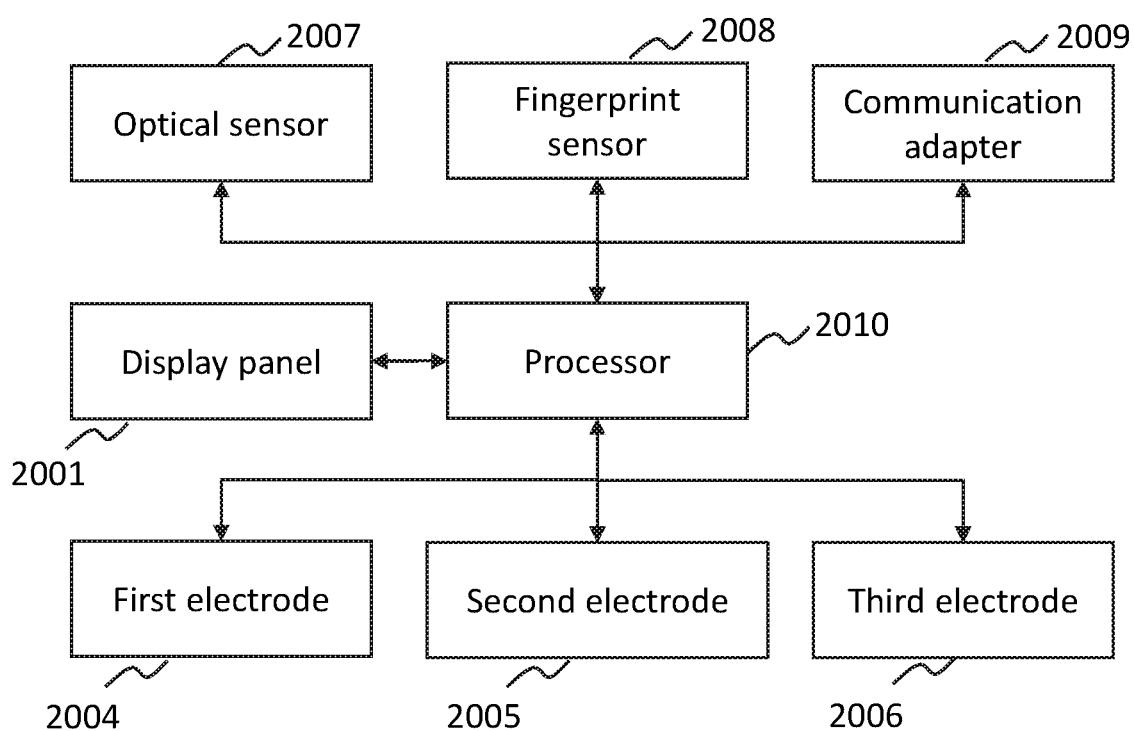
FIG. 20-C

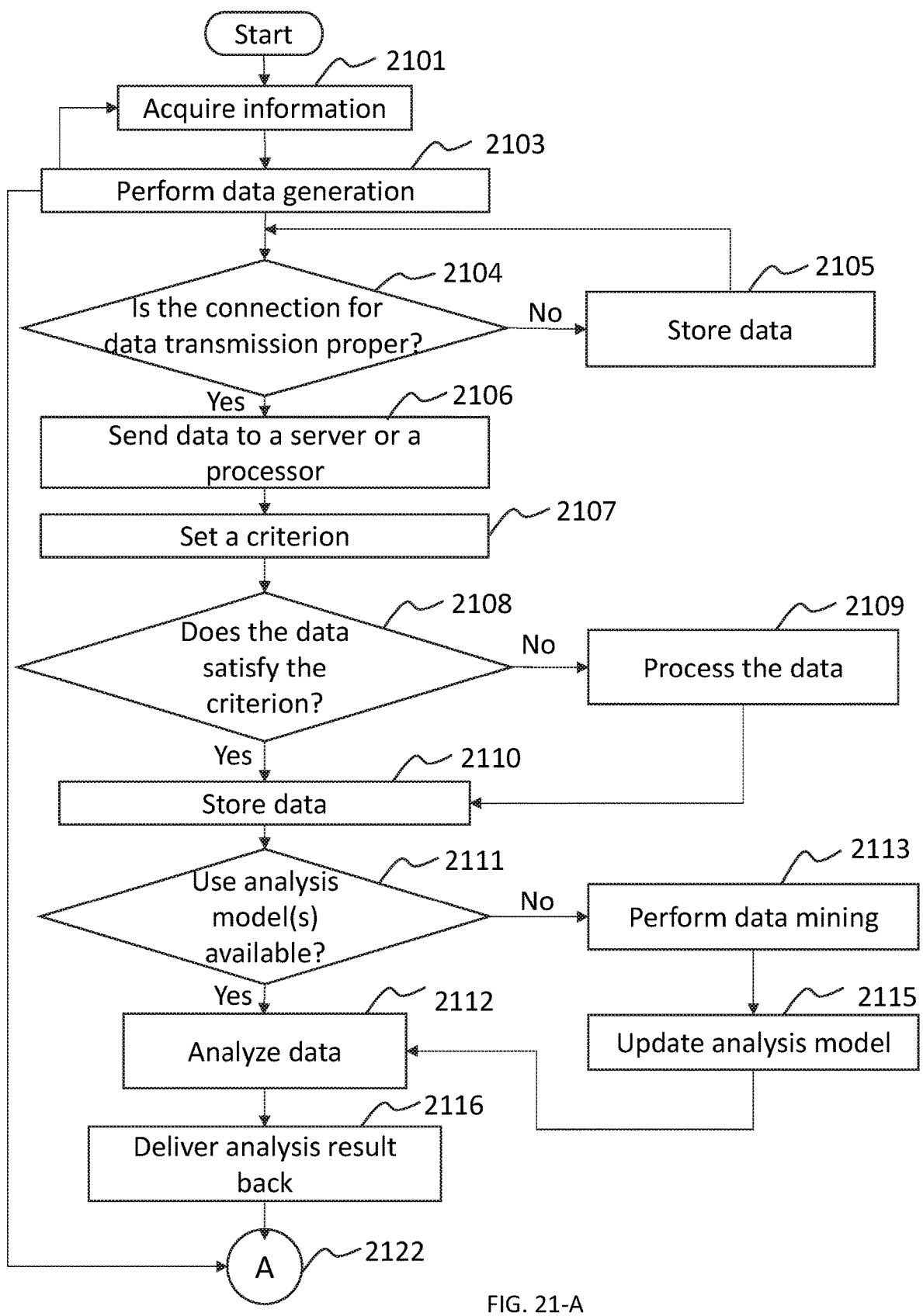
FIG. 21-A

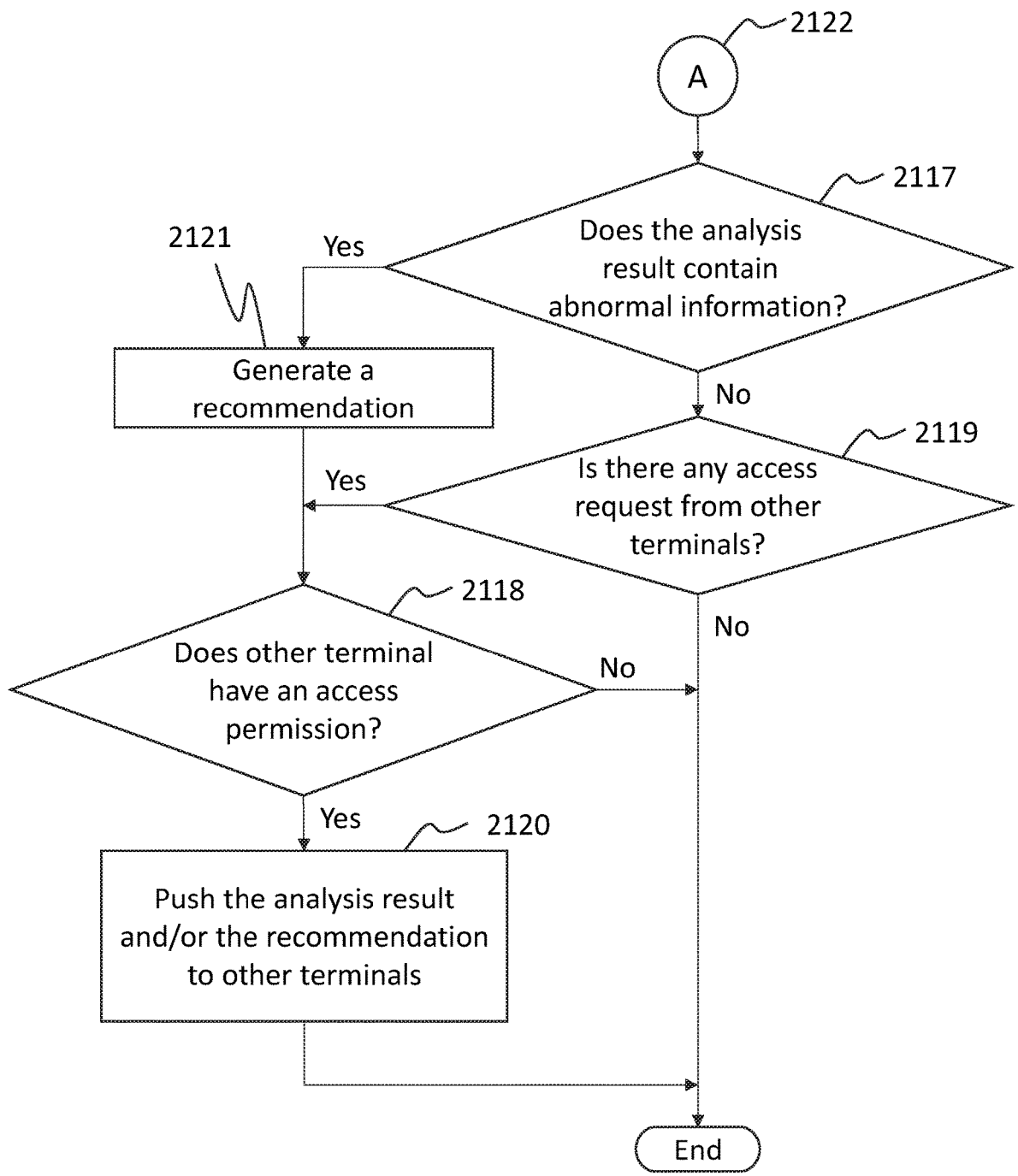
FIG. 21-B

SYSTEM AND METHOD FOR HEALTH MONITORING

CROSS-REFERENCE TO RELATED APPLICATIONS

This application is a continuation of U.S. application Ser. No. 15/537,377, field on Jun. 16, 2017, which is a U.S. national stage under 35 U.S.C. § 371 of International Application No. PCT/CN2016/070017, filed on Jan. 4, 2016, designating the United States of America and claims priority of International Application No. PCT/CN2015/083334 filed Jul. 3, 2015, and International Application No. PCT/CN2015/096498 filed Dec. 5, 2015, and Chinese Patent Application No. 201520188152.9 filed Mar. 31, 2015, and Chinese Patent Application No. 201510005387.4 filed Jan. 4, 2015, and Chinese Patent Application No. 201520188151.4 filed Mar. 31, 2015, and Chinese Patent Application No. 201520188130.2 filed Mar. 31, 2015, and Chinese Patent Application No. 201520188128.5 filed Mar. 31, 2015, and Chinese Patent Application No. 201520188127.0 filed Mar. 31, 2015, and Chinese Patent Application No. 201520242994.8 filed Apr. 21, 2015, and Chinese Patent Application No. 201520188308.3 filed Mar. 31, 2015, and Chinese Patent Application No. 201520192648.3 filed Apr. 1, 2015, and Chinese Patent Application No. 201520377166.5 filed Jun. 3, 2015, and Chinese Patent Application No. 201520188129.X filed Mar. 31, 2015, and Chinese Patent Application No. 201520186879.3 filed Mar. 31, 2015. The entire contents of the above applications are incorporated herein by reference.

TECHNICAL FIELD

The present disclosure generally relates to a system and method applicable in healthcare related areas. More particularly, the present disclosure relates to a system and method for health monitoring.

BACKGROUND

Health problems are important issues. However, it is difficult to monitor the health condition of a subject continuously and/or timely, especially for the aged, children, etc. Real-time monitoring of the health condition of a subject when he is in motion, driving, or operating a machine may provide valuable information for various reasons including, for example, safety concerns. There is a need for a system and method to monitor health condition of a subject continuously or in real time and/or share information relating to the health condition of the subject with another including, for example, a healthcare provide, a family member, or the like, or a combination thereof.

SUMMARY

Some embodiments of the present disclosure relates to a device including memory storing instructions, and at least one processor. The device may be used to estimate or monitor the health condition of a subject. When the at least one processor executing the instructions, the at least one process may perform one or more of the following operations. At least one physiological signal or information including a physiological signal of a subject may be received. At least one physiological parameter of interest may be generated based on the physiological signal. The physiological parameter of interest may be analyzed according to an analysis model. A physiological result may be generated. A recommendation may be provided based on the physiological analysis result.

Some embodiments of the present disclosure relates to a method implemented on at least one processor for estimating or monitoring the health condition of a subject. The method may include one or more of the following operations. At least one physiological signal or information including a physiological signal of a subject may be received. At least one physiological parameter of interest may be generated based on the physiological signal. The physiological parameter of interest may be analyzed according to an analysis model. A physiological result may be generated. A recommendation may be provided based on the physiological analysis result.

Some embodiments of the present disclosure relates to a system implemented on memory and at least one processor. The system may be used to estimate or monitoring the health condition of a subject. The system may include a measuring module, a generation unit, and an analysis unit. The measuring module may be configured to receive at least one physiological signal of a subject. The generation unit may be configured to generate at least one physiological parameter of interest based on the physiological signal. The analysis unit may be configured to analyze the physiological parameter of interest according to an analysis model; generate a physiological analysis result; provide a recommendation based on the physiological analysis result.

In some embodiments, the receiving at least one physiological signal comprising communicating with at least one physiological sensor located on at least one location on the body of the subject. The physiological sensor may be part of the device. The physiological sensor may include an electric sensor, an optical sensor, a temperature sensor, an acceleration sensor, or a pressure sensor. The location may include at least one location selected from the head, the neck, the chest, the abdomen, the upper arm, the wrist, the waist, the upper leg, the knee, or the ankle of the subject.

In some embodiments, the electric sensor may include an electrode. The electrode may include a flexible conductive layer, a gluing layer, and a button configured to connect the conductive layer and the gluing layer. The flexible conductive layer may include a first opening and the gluing layer comprising a second opening. The first opening may correspond to the second opening, the button may be fixed in the opening and contact with the flexible conductive layer.

In some embodiments, the physiological signal may include an ECG signal, a pulse related signal, or a temperature signal. In some embodiments, the physiological parameter of interest may include an ECG diagram, a heart rate, a heart rate variation, a pulse rate, a pulse rate variation, a blood oxygen level, a body temperature value, or a blood pressure. In some embodiments, the physiological analysis result may include a health condition evaluation. In some embodiments, the health condition evaluation may include a change of the physiological parameters of interest with time, a difference with statistical data, or abnormalities in the physiological parameter of interest. In some embodiments, the recommendation may include a health tip, or a medical guide.

In some embodiments, the at least one of the physiological signal, physiological parameter of interest, a physiological analysis result, a recommendation may be transmitted to a related member with the subject. The transmitting may include verifying an identify of the related member; and allowing an access privilege to the related member.

In some embodiments, the at least one processor may further receive information relating to the subject or a condition when the physiological signal are received. Exemplary information may include, e.g., age, body weight, the time (during the day) or the date the first signal or the second signal is acquired, the room temperature, the mood of the subject at the time, whether the subject has recently exercised, or the like, or a combination thereof. Such information may be taken into consideration when the blood pressure of the subject is calculated using the device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A and FIG. 1-B illustrate exemplary system configurations in which a system for health monitoring may be deployed in accordance with various embodiments of the present disclosure;

FIG. 4-A and FIG. 4-B are block diagrams illustrating the architecture of a terminal according to some embodiments of the present disclosure;

FIG. 4-C is a flowchart of an exemplary process for processing information according to some embodiments of the present disclosure;

FIG. 5-A and FIG. 5-B are block diagrams illustrating the architecture of a health information management engine according to some embodiments of the present disclosure;

FIG. 5-C is a flowchart of an exemplary process for analyzing data according to some embodiments of the present disclosure;

FIG. 8-A through FIG. 8-D show an exemplary smart watch according to some embodiments of the present disclosure;

FIG. 9-A and FIG. 9-B illustrate a top view and a bottom view of a smart watch according to some embodiments of the present disclosure;

FIG. 10-A through FIG. 10-C show an exemplary electrode which may be used to acquire an ECG signal according to some embodiments of the present disclosure;

FIG. 12-A and FIG. 12-B show an exemplary measuring device according to some embodiments of the present disclosure;

FIG. 14-A through FIG. 14-C show an exemplary neckband according to some embodiments of the present disclosure;

FIG. 15-A and FIG. 15-B show an exemplary wristband according to some embodiments of the present disclosure;

FIG. 17-A and FIG. 17-B show an exemplary steering wheel according to some embodiments of the present disclosure;

FIG. 18-A and FIG. 18-B show an exemplary jump rope according to some embodiments of the present disclosure;

FIG. 19-A and FIG. 19-B shown an exemplary mouse and mouse pad according to some embodiments of the present disclosure;

FIG. 20-A through FIG. 20-C show an exemplary tablet according to some embodiments of the present disclosure.

FIG. 21-A and FIG. 21-B show a flowchart diagram of an exemplary health monitoring process according to some embodiments of the present disclosure.

DETAILED DESCRIPTION

Figure 2:
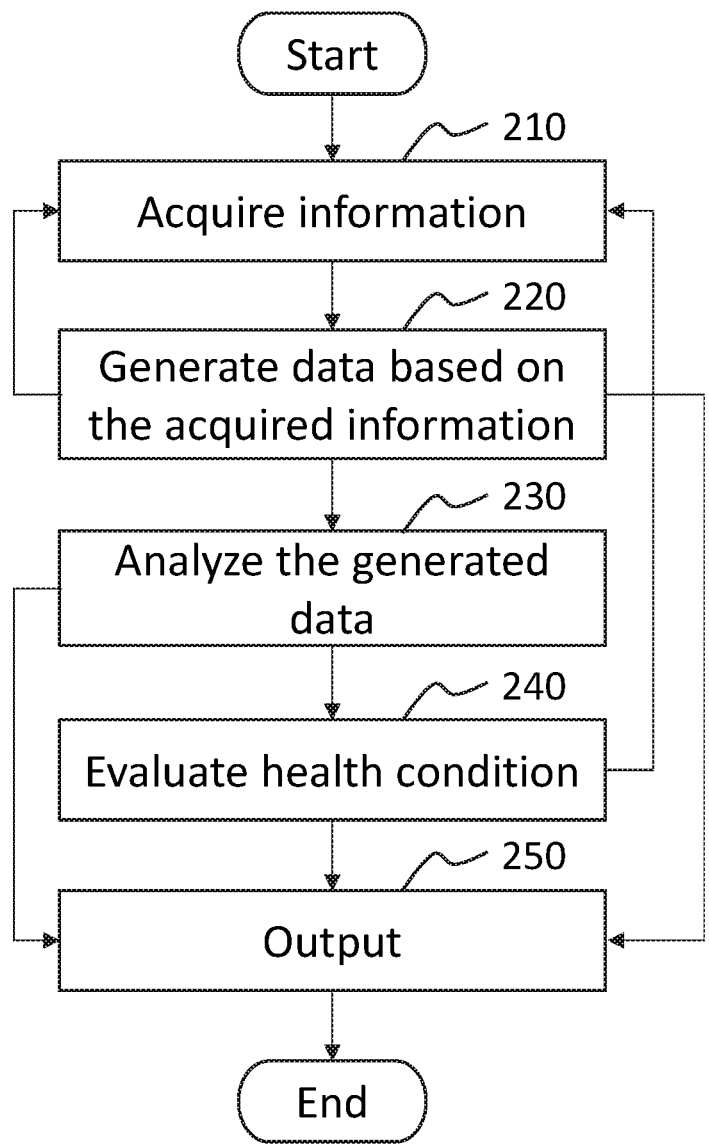
FIG. 2 is a flowchart of an exemplary process in which a method for health monitoring is deployed, according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure.

The present disclosure relates to system, method, and programming aspects of health monitoring. The health monitoring may involve acquiring a plurality of physiological signals, information and parameters. The system and method may involve improved sensor design and signal processing. The system and method as disclosed herein may perform health monitoring continuously in a non-invasive way, with improved accuracy. The system and method may acquire blood pressure, blood oxygen level, heart rate, heart rate variation, pulse rate, pulse rate variation, body fat, or the like, or a combination thereof. The following description is provided for illustration purposes, and is not intended to limit the scope of the present disclosure.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. As used in the specification and in the claims, the singular form of "a," "an," and "the" include plural referents unless the context clearly dictates otherwise.

The present disclosure generally relates to a system and method applicable in healthcare related areas. More particularly, the present disclosure relates to a system and method for health monitoring. In some embodiments, the system and/or various measuring devices may be used to perform real-time and/or continuously monitoring of one or more physiological parameters of interest of a subject in various situations including, for example, when the subject is in motion or operating a mobile vehicle or machine. Such measuring devices may be part of the system, or may communicate with the system. In some embodiments, the system may facilitate the sharing of the physiological parameter(s) of interest and/or relevant information relating to the subject with someone else including, for example, a healthcare provider, a family member, a guardian, a hospital, or the like, or a combination thereof. The information sharing may be performed real-time, with a delay, periodically, triggered by an event, or the like, or a combination thereof.

FIG. 1 illustrates an exemplary system configuration in which a system 100 may be deployed in accordance with some embodiments of the present disclosure. The system 100 may be configured to monitor a physiological parameter of interest. The system 100 may include a measuring device 110, a health information management engine 120, a terminal 130, a database 140, and a network 150. The measuring device 110 may be configured for acquiring a physiological signal, physiological information, or an environmental signal. The measuring device 110 may include a plurality of devices, such as 110-1, 110-2, 110-3, . . . , 110-N. The terminal 130 may include a plurality of terminals, such as, 130-1, 130-2, 130-3, . . . , 130-N. Various components of the system 100 may be connected to each other directly or indirectly via the network 150.

The measuring device 110 may be configured to measure a signal. The signal may be a physiological signal. The signal may relate to or be used to calculate or estimate a physiological parameter of interest. The measuring device 110 may include, for example, a clinical device, a household device, a portable device, a wearable device, a life tool, or the like, or a combination thereof. As used herein, a clinical device may be one that meets applicable requirements and specifications to be used in a clinical setting including, e.g., a hospital, a doctor's office, a nursing home, or the like. A clinical device may be used by or with the assistance of a healthcare provider. As used herein, a household device may be one that meets applicable requirements and specifications to be used at home or a nonclinical setting. A household device may be used by someone who is or is not a professional provider. A clinical device or a household device, or a portion thereof, may be portable or wearable. As used herein, a life tool may be one that may be used in daily life.

Exemplary clinical devices include an auscultatory device, an oscillometric device, an ECG monitor, a PPG monitor, or the like, or a combination thereof. Exemplary household devices include an oscillometric device, a household ECG monitor, a sphygmometer, or the like, or a combination thereof. Exemplary portable devices include an oscillometric device, a portable ECG monitor, a portable PPG monitor, or the like, or a combination thereof. Exemplary wearable devices include a smart watch (see FIG. 8-A through FIG. 8-D, and FIG. 9-A and FIG. 9-B), a pair of glasses (see FIG. 12-A and FIG. 12-B), a ring (see FIG. 13), a neckband (see FIG. 14-A and FIG. 14-B), a wristband (see FIG. 15-A and FIG. 15-B), a shoulder strap, an anklet, a thigh band, a chest belt, an armband, a necklet, or the like, or a combination thereof. A tool may be a device used in daily life, such as, a bicycle (see FIG. 16), a steering wheel (see FIG. 17-A and FIG. 17-B), a jump rope (see FIG. 18-A and FIG. 18-B), a mouse (see FIG. 19-A and FIG. 19-B), a tablet (see FIG. 20-A and FIG. 20-B), or the like, or a combination thereof. The above mentioned examples of measuring devices 110 are provided for illustration purposes, and not intended to limit the scope of the present disclosure. A measuring device 110 may be in other forms, such as a brassiere, an underwear, a chest band, some other life tools (e.g., an umbrella, a treadmill, or the like), or the like, or a combination thereof.

The measuring device 110 may be any combination of a clinical device, a house hold device, a wearable or portable device, and a tool. The measuring device 110 in combination may be configured for acquiring signals from multiple locations on the body of the subject. For example, the measuring device 110 may be a combination of a wearable device (e.g., a pair of glasses, see FIG. 12-A and FIG. 12-B) and a tool (e.g., a steering wheel, see FIG. 17-A and FIG. 17-B), sensors on the steering wheel and the pair of glasses may be coordinate to provide signals from multiple body locations. As another example, the measuring device 110 may be a combination of a wearable device (e.g., a pair of glasses, see FIG. 12-A and FIG. 12-B) and a tool (e.g., a mouse, see FIG. 19-A and FIG. 19-B), sensors on the pair of glasses and the mouse may be coordinate to provide signals from multiple body locations. More detailed descriptions regarding acquiring signals from multiple body locations may be found in International Application No. PCT/CN2015/096498 filed Dec. 5, 2015.

Merely by way of example, the measuring device 110 may be a wearable or portable device, or may be integrated in or combined with a tool, configured to measure one or more physiological signals. In some embodiments, the wearable or portable device may process at least some of the measured signals, estimate a physiological parameter of interest based on the measured signals, display a result including the physiological parameter of interest in the form of, e.g., an image, an audio alert, perform wired or wireless communication with a terminal 130 or the health information management engine 120, or the like, or a combination thereof. The terminal 130 or the health information management engine 120 may process and analyze at least some of the measured signals, generate a physiological result based on the measured signals or the estimated physiological parameters of interest, display or present a result including the physiological result. The result may be displayed or presented in the form of, e.g., an image, an audio alert, a video, a graph, text, a haptic alert, or the like, or a combination thereof.

In some embodiments, the operations of processing the measured signals, estimating a physiological parameter, displaying or presenting a result, or performing wired or wireless communication may be performed by an integrated device or by separate devices connected to or communicating with each other. Such an integrated device may be portable or wearable. In some embodiments, at least some of the separate devices may be portable or wearable, or located in the vicinity of a subject whose signal is measured or a physiological parameter of interest is estimated or monitored. Merely by way of example, the subject wears the measuring device 110 that is configured to measure one or more physiological signals; the measured one or more physiological signals are transmitted to a terminal 130-1

(e.g., a smart phone) that is configured to calculate or estimate a physiological parameter of interest based on the measured signals, and to analyze or process the signals of parameters. In some embodiments, at least some of the separate devices are located in a location remote from the subject. Merely by way of example, the subject wears the measuring device 110 that is configured to measure one or more signals; the measured one or more signals are transmitted to the health information management engine 120 or a processor that is configured to calculate or estimate multiple physiological parameters of interest based on the measured signals, and to analyze or process the measured signals and/or the calculated or estimated physiological parameters of interest; the acquired signals, calculated or estimated physiological parameters of interest, and/or the analysis results may be provided to the subject, or a user other than the subject (for example, a doctor, a care provider, a family member relating to the subject, or the like, or a combination thereof). In some embodiments, the acquired signals, calculated or estimated physiological parameters of interest, and/or the analysis results may be transmitted to another terminal 130-2.

The system 100 may include or communicate with a server, e.g., the health information management engine 120. The health information management engine 120 may be a local server, a remote server, or a cloud server. The health information management engine 120 may be configured for processing or analyzing the acquired signals, received information and/or retrieved data from the database 140. In some embodiments, the health information management engine 120 may be implemented in a cloud server that may provide storage capacity, computation capacity, or the like, or a combination thereof. The health information management engine 120 may be configured to collect or store data. The data may include personal data, non-personal data, or both. The data may include static data, dynamic data, or both. Exemplary static personal data may include various information regarding a subject including identity, contact information, birthday, a health history (for example, whether a subject has a history of smoking, information regarding a prior surgery, a food allergy, a drug allergy, a medical treatment history, a history of genetic disease, a family health history, or the like, or a combination thereof), the gender, the nationality, the height, the weight, the occupation, a habit (for example, a health-related habit such as an exercise habit), the education background, a hobby, the marital status, religious belief, or the like, or a combination thereof. Static data may change over time. For instance, a subject may move and his contact information may change. As another example, a subject may drop a habit or develop a new habit, or change his occupation. Exemplary personal dynamic data may include a current health condition of a subject, medications the subject is taking, a medical treatment the subject is undertaking, diet, physiological signals or parameters (for example, pulse transit time (PTT), systolic blood pressure (SBP), diastolic blood pressure (DBP), ECG, PPG, blood oxygen level, or the like) relating to the subject for multiple time points or over a period of time, or the like, or a combination thereof. In some embodiments, the data may be stored locally on the measuring device 110 or the terminal 130. Exemplary static non-personal data may include a history of a disease or health condition in an area, among a general population, among a sub-population sharing a characteristic, etc. Exemplary dynamic non-personal data may include the spreading of an epidemic disease in an area, among a general population, among a sub-population sharing a characteristic, etc.

The system 100 may include or communicate with one or more terminals 130. The terminal 130 may be configured for processing at least some of the measured signals, estimating a physiological parameter of interest based on the measured signals, displaying or presenting a result including the physiological parameter of interest, storing data, controlling access to the system 100 or a portion thereof (for example, access to the personal data stored in the system 100 or accessible from the system 100), managing input-output from or relating to a subject, or the like, or a combination thereof. The measured signals may include one or more physiological signals, one or more signals relating to environmental information, or the like, or a combination thereof. The result may be displayed or presented in the form of, for example, an image, an audio alert, a video, a graph, text, a haptic alert, or the like, or a combination thereof. The terminal 130 may include, for example, a mobile device (for example, a smart phone, a tablet, a laptop computer, or the like), a personal computer, or the like, or a combination thereof. The terminal 130 also may be a device that may work independently, or a processing unit or processing module assembled in another device (for example, an intelligent home terminal). Merely by way of example, the terminal 130 includes a CPU or a processor in the measuring device 110. In some embodiments, the terminal 130 and the measuring device 110 may be integrated in an independent device (e.g., see FIG. 20). The system 100 may include a plurality of terminals, e.g., 130-1, 130-2, . . . , 130-N. The plurality of terminals may be connected with or communicate with each other through the network 150.

The database 140 may be a database provided by a variety of organizations, systems, and devices, or the like, or a combination thereof. Exemplary organizations may include a medical institution, a research facility, or the like, or a combination thereof. Exemplary system or device may include a conventional device, a peripheral device, or the like, or a combination thereof. The medical institution or the research facility may provide, for example, personal medical records, clinical test results, experimental research results, theoretical or mathematical research results, algorithms suitable for processing data, or the like, or a combination thereof The conventional device may include a cardiovascular signal measuring device, such as a mercury sphygmomanometer. A peripheral device may be configured to monitor and/or detect one or more types of variables including, for example, temperature, humidity, user or subject input, or the like, or a combination thereof. The above mentioned examples of the database 140 and data types are provided for illustration purposes, and not intended to limit the scope of the present disclosure. For instance, the database 140 may include other sources and other types of data, such as genetic information relating to a subject or his family. Access to the database 140 may be controlled or gated. A subject or a user other than the subject may need an access privilege to visit the database 140. Different subjects or users other than the subjects may have different access privileges to different parts of the database 140.

The network 150 may be a single network or a combination of different networks. For example, the network 150 may be a local area network (LAN), a wide area network (WAN), a public network, a private network, a proprietary network, a Public Telephone Switched Network (PSTN), the Internet, a wireless network, a virtual network, or any combination thereof. The network 150 may also include various network access points, for example, wired or wireless access points such as base stations or Internet exchange points (not shown in FIG. 1), through which a data source or any component of the system 100 described above may connect to the network 150 in order to transmit information via the network 150.

Various components of or accessible from the system 100 may include a memory or electronic storage media. Such components may include, for example, the measuring device 110, the health information management engine 120, the terminal 130, the database 140, or the like, or a combination thereof. The memory or electronic storage media of any component of the system 100 may include one or both of a system storage (for example, a disk) that is provided integrally (i.e. substantially non-removable) with the component, and a removable storage that may be removably connected to the component via, for example, a port (for example, a USB port, a firewire port, etc.) or a drive (for example, a disk drive, etc.). The memory or electronic storage media of any component of the system 100 may include or be operationally connected with one or more virtual storage resources (for example, a cloud storage, a virtual private network, and/or other virtual storage resources).

The memory or electronic storage media of the system 100 may include a dynamic storage device configured to store information and instructions to be executed by the processor of a system-on-chip (SoC, for example, a chipset including a processor), other processors (or computing units), or the like, or a combination thereof. The memory or electronic storage media may also be used to store temporary variables or other intermediate information during execution of instructions by the processor(s). Part of or the entire memory or electronic storage media may be implemented as Dual In-line Memory Modules (DIMMs), and may be one or more of the following types of memory: static random access memory (SRAM), Burst SRAM or Synch Burst SRAM (BSRAM), dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDECSRAM, PCIOO SDRAM, Double Data Rate SDRAM (DDR SDRAM), Enhanced SDRAM (ESDRAM), Sync Link DRAM (SLDRAM), Direct Rambus DRAM (DRDRAM), Ferroelectric RAM (FRAM), or any other type of memory device. The memory or electronic storage media may also include read-only memory (ROM) and/or another static storage device configured to store static information and instructions for the processor of the SoC and/or other processors (or computing units). Further, the memory or electronic storage media may include a magnetic disk, optical disc or flash memory devices to store information and instructions.

In some embodiments, the SoC may be part of a core processing or computing unit of a component of or accessible from the system 100. The SoC may be configured to receive and process input data and instructions, provide output and/or control other components of the system. In some embodiments, the SoC may include a microprocessor, a memory controller, a memory, and a peripheral component. The microprocessor may further include a cache memory (for example, SRAM), which along with the memory of the SoC may be part of a memory hierarchy to store instructions and data. The microprocessor may also include one or more logic modules such as a field programmable gate array (FPGA) or other logic array. Communication between the microprocessor in the SoC and memory may be facilitated by the memory controller (or chipset), which may also facilitate in communicating with the peripheral component, such as a counter-timer, a real-time timer, a power-on reset generator, or the like, or a combination thereof. The SoC may also include other components including, for example, a timing source (for example, an oscillator, a phase-locked loop, or the like), a voltage regulator, a power management circuit, or the like, or a combination thereof.

Merely by way of example, the system 100 may include a wearable or portable device. The wearable or portable device may include a SoC. The wearable or portable device may include, connect to, or communicate with a plurality of sensors. Exemplary sensors may include a photoelectric sensor, a conductance sensor, or the like, or a combination thereof. The SoC may process signals acquired through at least some of the plurality of sensors. The acquired signals may be various physiological signals including, for example, photoplethysmograph (PPG), electrocardiograph (ECG), or the like, or a combination thereof. The SoC may calculate a physiological parameter of interest based on the acquired signals. Exemplary physiological parameters of interest may be blood pressure, blood oxygen level, ECG information, heart rate, or the like, or a combination thereof.

In some embodiments, the database 140 may receive data from the measuring device 110, the health information management engine 120, the terminal 130, or the like, or any combination by the network 150. Merely by way of example, the database 140 (for example, a medical institution, or a smart home system, or the like) may receive information relating to a subject (for example, location information, data from the cloud sever or a terminal, or the like, or a combination thereof) based on the data received from the measuring devices 110 or the terminal 130. In some embodiments, the measuring device 110 may receive data from the health information management engine 120, the database 130, or the like, or any combination via the network 150. Merely by way of example, the measuring device 110 may receive information relating to a subject (for example, a current/historical health condition of a subject, medications the subject is taking, medical treatment the subject is undertaking, current/historical diets, current emotion status, historical physiological parameters (for example, PTT, SBP, DBP) relating to the subject, or the like, or a combination thereof). Furthermore, the terminal 130 may receive data from the measuring device 110, the health information management engine 120, the database 140, or the like, or a combination thereof.

FIG. 1-B illustrates a similar system configuration as what is shown in FIG. 1-A except that the database 140 may be configured to connect to the network 150 via the health information management engine 120. Access to the database 140 may be controlled or gated. A subject or a user other than the subject may need an access privilege to visit the database 140. Different subjects or users other than the subjects may have different access privileges to different parts of the database 140.

FIG. 1-A and FIG. 1-B are examples of the system 100 in a networked environment.

The configuration of the system 100 are not limited to that illustrated in FIG. 1-A or FIG. 1-B. For example, a health information management engine 120 may be omitted, migrating all of its functions to a terminal 130. In another example, a health information management engine 120 and a terminal 130 may both be omitted, migrating all of their functions to a measuring device 110. In a further example, a database 140 may be omitted, migrating all of its functions to the health information management engine 120.

In one example, the system may include, connect to or communicate with a wearable or portable device and a mobile device (for example, a smart phone, a tablet, a laptop computer, or the like). The wearable or portable device may be used to acquire physiological signals, environmental information, or the like, or a combination thereof. The mobile device may be used to receive the signals or information acquired by the wearable or portable device. The mobile device may calculate one or more physiological parameters of interest based on the acquired signals or information, as well as relevant data retrieved from another source (for example, from a server, a memory incorporated in the wearable or portable device, a memory incorporated in the mobile device, etc.). The retrieved relevant data may include, for example, current/historical information stored on the server. The mobile device may analyze the acquired signals, and/or the calculated physiological parameters of interest. Exemplary current/historical information may include a current/historical health condition of a subject, current/historical medications the subject is/was taking, current/historical medical treatment the subject is/was undertaking, current/historical diets, current/historical emotion status, current/historical physiological parameters (for example, PTT, SBP, DBP, ECG information, heart rate, blood oxygen level) relating to the subject, or the like, or a combination thereof. More detailed descriptions may be found in International Application Nos. PCT/CN2015/083334 filed Jul. 3, 2015 and PCT/CN2015/096498 filed Dec. 5, 2015. The wearable or portable device, or the mobile device may display, present, or report, or store at least some of the acquired signals, information, the retrieved relevant data, the calculated one or more physiological parameters of interest, the analysis results, or the like, or a combination thereof. The display, presentation, or report may be provided to a subject, a user other than the subject, a third party, the server, or other terminals.

In another example, the system may include, connect to, or communicate with a wearable or portable device that may be configured to perform functions including: acquiring physiological signals or environmental information, retrieving relevant data from another source (for example, from a server, a memory incorporated in the wearable or portable device, etc.), calculating one or more physiological parameters of interest based on the acquired signals, information, or the retrieved relevant data, analyzing the acquired signals and/or the calculated physiological parameters of interest, and displaying, presenting, reporting, or storing at least some of the acquired signals, information, the retrieved relevant data, the calculated one or more physiological parameters of interest, the analysis results, or the like, or a combination thereof. The display, presentation, or report may be provided to a subject, a user other than the subject, a third party, the server, or another device.

In a further example, the system may include, connect to, or communicate with a wearable or portable device that may be configured to perform functions including: acquiring physiological signals and environmental information, communicating with a server to transmit at least some of the acquired signals or information to the server such that the server may calculate one or more physiological parameters of interest and analyze the acquired signals and/or the calculated physiological parameters of interest, receiving the calculated one or more physiological parameters of interest and the analysis results from the server, displaying, presenting, reporting, or storing at least some of the acquired signals, information, the calculated one or more physiological parameters of interest, or the like, or a combination thereof. The display, presentation, or report may be provided to a subject, a user other than the subject, a third party, the server, or another device. In some embodiments, the communication between the wearable or portable device and the server may be achieved by way of the wearable or portable device being connected to a network (for example, the network 150). In some embodiments, the communication between the wearable or portable device and the server may be achieved via a communication device (for example, a mobile device such as a smart phone, a tablet, a laptop computer, or the like) that communicates with both the wearable or portable device and the server. A health information management engine 120 may be implemented on the server. The health information management engine 120 may perform the calculation of one or more physiological parameters of interest and/or the analysis of the acquired signals and/or the calculated physiological parameters of interest.

In still a further example, the system may include, connect to, or communicate with a wearable or portable device, a mobile device (for example, a smart phone, a tablet, a laptop computer, or the like), and a server. The wearable or portable device may be used to acquire physiological signals, environmental information, or the like, or a combination thereof. The mobile device may be used to receive the signals or information acquired by the wearable or portable device, may calculate one or more physiological parameters of interest based on the received signals and/or information retrieved from the wearable or portable device, as well as relevant data retrieved from, for example, a server, a memory incorporated in the wearable or portable device or incorporated in the mobile device, and analyze the acquired signals and/or the calculated physiological parameters of interest. The mobile device may display, present, report, or store at least some of the acquired signals, information, the retrieved relevant data, the calculated one or more physiological parameters of interest, or the like, or a combination thereof. The display, presentation, or report may be provided to a subject, a user other than the subject, a third party, the server, or another device. A health information management engine 120 may be implemented on the server. The health information management engine 120 may perform the calculation of one or more physiological parameters of interest and/or the analysis of the acquired signals and/or the calculated physiological parameters of interest.

In a still a further example, the system may include a wearable or a portable device, a mobile device ((for example, a smart phone, a tablet, a laptop computer, or the like), and a server. The wearable or portable device may be used to acquire physiological signals, environmental information, or the like, or a combination thereof. The mobile device may be used to receive the signals or information acquired by the wearable or portable device, may calculate one or more physiological parameters of interest based on the received signals and/or information retrieved from the wearable or portable device, as well as relevant data retrieved from, for example, a server, a memory incorporated in the wearable or portable device or incorporated in the mobile device. The server may receive the signals or information acquired by the wearable or portable device and the physiological parameters of interest calculated by the mobile device, analyze the received signals, information and physiological parameters of interest, and transmit the analysis results to the mobile device. A health information management engine 120 may be implemented on the server. The health information management engine 120 may perform the calculation of one or more physiological parameters of interest and/or the analysis of the acquired signals and/or the calculated physiological parameters of interest. In the exemplary embodiment, some of the calculation or analysis may be performed by the mobile device, some of the calculation or analysis may be performed by the health information management engine 120 implemented on the server. The mobile device may display, present, report, or store at least some of the acquired signals, information, the retrieved relevant data, the calculated one or more physiological parameters of interest, the analysis results, or the like, or a combination thereof. The display, presentation, or report may be provided to a subject, a user other than the subject, a third party, the server, or another device.

In another example, the system may include a measuring device 110 integrated in a tool used in daily life (such as a bicycle configured to monitor one or more physiological signals or parameters of the subject during a bike riding), and a mobile device and/or a server. A measuring device integrated in the tool may be used to acquire one or more physiological signals, environmental information, or the like, or a combination thereof. In some embodiments, the tool may include a processor, for example, a SoC, configured to calculate one or more physiological parameters of interest based on the acquired signals or information; analyze the acquired signals, information and the calculated physiological parameters of interest; display, present, report, or store at least some of the acquired signals, information, the retrieved relevant data, the calculated one or more physiological parameters of interest, the analysis results, or the like, or a combination thereof. The display or report may be provided to a subject, a user other than the subject, a third party, the server, or another device. A health information management engine 120 may be implemented on the server. In some embodiments, some of the operations mentioned above may be performed by the mobile device or the server. For instance, the mobile device or the server may perform one or more operations including the calculation, the analysis, the communication (for receiving or transmitting the acquired signals or results) between the tool or any components integrated therein, the server, and the mobile device, another terminal, the subject, a user other than the subject, etc.

In some embodiments, the system may be configured to provide a user interface to allow a subject, a user other than the subject, or an entity to exchange information (including input into or output from the system) with the system as disclosed herein. The user interface may be implemented or presented on a terminal device including, for example, a mobile device, a computer, or the like, or a combination thereof. The user interface may be presented on, e.g., a display device of the system.

The access to the system, or a portion thereof (for example, the database 140, the health information management engine 120), may be allowed to one who has an appropriate access privilege. An access privilege may include, for example, a privilege to read some or all information relating to a subject, update some or all information relating to a subject, or the like, or a combination thereof. The access privilege may be associated with or linked to a set of login credentials. Merely by way of example, the system may provide three tiers of access privileges. A first tier may include a full access privilege regarding information relating to a subject, allowing both receiving and updating information relating to a subject. A second tier may include a partial access privilege regarding information relating to a subject, allowing receiving and updating part of information relating to a subject. A third tier may include a minimal access privilege regarding information relating to a subject, allowing receiving part of or all information relating to a subject. Different login credentials may be associated with different access privileges to the information relating to a subject in the system. As used herein, updating may include providing information that does not exist in the system, or modifying pre-existing information with new information.

Merely by way of example, the system may receive information relating to a subject provided via the user interface. The information relating to a subject may include basic information and optional information. Exemplary basic information may include the height, the weight, the age (or the date of birth), the gender, the arm length, the nationality, the occupation, a habit (for example, a health-related habit such as an exercise habit), the education background, a hobby, the marital status, religious belief, a health-related history (for example, whether a subject has a history of smoking, a food allergy, a drug allergy, a medical treatment history, a family health history, a history of genetic disease, information regarding a prior surgery, or the like, or a combination thereof), contact information, emergency contact, or the like, or a combination thereof. Exemplary optional information may include, current health condition of the subject, medications the subject is taking, a medical treatment the subject is undertaking, diet. The system may receive, via the user interface, information relating to a specific measurement of, for example, a physiological parameter of interest. Examples of such information may include the motion state of the subject at or around the acquisition time (defined elsewhere in the present disclosure), the emotional state at or around the acquisition time, the stress level at or around the acquisition time, or the like, or a combination thereof. As used herein, the acquisition time may refer to a time point or a time period when information relating to the subject, e.g., physiological information of the subject, is acquired using, for example, a measuring device. The system may receive, via the user interface, one or more options or instructions. In some embodiments, the options or instructions may be provided by a subject or a user other than the subject answering questions or making selections in response to questions or prompts by the system. In one example, the options or instructions may include a measurement frequency (for example, once a week, once a month, twice a week, twice a month, once a day, twice a day, or the like), a preferred format of the presentation of information to the subject or a user other than the subject (for example, email, a voice message, a text message, an audio alert, a video presentation, haptic feedback, or the like, or a combination thereof). In another example, the options or instructions may include information relating to calculating parameters of interest, for example, rules regarding how to select a model, a function, calibration data, or the like, or a combination thereof.

In some embodiments, the system may provide, via the user interface, information to a subject, or a user other than the subject. Exemplary information may include an alert, a recommendation, a reminder, or the like, or a combination thereof. In one example, an alert may be provided or displayed to the subject or a user other than the subject if a triggering event occurs. Exemplary triggering events may be that at least some of the acquired information or a physiological parameter of interest exceeds a threshold. Merely by way of example, a triggering event may be that the acquired heart rate exceeds a threshold (for example, higher than 150 beats per minute, lower than 40 beats per minute, or the like). As another example, a triggering event may be that the physiological parameter of interest, for example, an estimated blood pressure, exceeds a threshold. In another example, a recommendation may be provided or displayed to the subject or a user other than the subject. Exemplary recommendations may be a request to input specific data (for example, basic information, optional information, updated parameters of interest, updated models, updated functions, updated options and instructions, or the like, or a combination thereof). A reminder may be provided or displayed to the subject or a user other than the subject. Exemplary reminders may include a reminder to take a prescription medication, take a rest, take a measurement of a physiological parameter of interest, or the like, or a combination thereof.

In some embodiments, the system may communicate with the subject, a user other than the subject, and/or a third party through the user interface. Exemplary third parties may be a doctor, a healthcare worker, a medical institution, a research facility, a peripheral device of the subject or a user well-connected to the subject, or the like. Exemplary communications may relate to the health conditions of the subject, a dietary habit, an exercise habit, a prescription medication, instructions or steps to conduct a measurement, or the like, or a combination thereof. In some embodiments, a user interface accessible to or by a third party may be the same as, or different from a user interface accessible to or by a subject. In one example, an output or data may be transmitted to a third party (for example, a computer, a terminal at a doctor's office, a hospital where a health care provider is located and the health condition of the subject is being monitored, or the like, or a combination thereof). The third party may provide feedback information or instructions related to the output information via the user interface. Merely by way of example, a third party may receive information regarding one or more physiological parameters of interest relating to a subject, and accordingly provide a recommendation of actions to be taken by the subject (for example, to take a prescription medication, to take a rest, to contact or visit the third party, or the like, or a combination thereof); the system may relay the recommendation to the subject.

FIG. 2 is a flowchart of an exemplary process in which a method for health monitoring is deployed, according to some embodiments of the present disclosure. Information regarding a subject may be acquired in step 210. The information acquisition may be performed by the measuring device 110 or may be inputted by the subject or a user other than the subject (e.g., a related family member, a doctor, or the like). The acquisition process may be performed automatically in real time or at a certain time interval (e.g., twice a day), based on instructions by the subject (e.g., a start instruction), or triggered by a triggering event (e.g., while the measuring device is in contact with the body of the subject). The acquired information may include physiological information of the subject, basic information of the subject (e.g., age, gender, illness history, or the like), and/or environmental information relating to the ambient surrounding the subject Merely by way of example, the acquired information may include a PPG signal, ECG signal, body temperature signal, the height, weight, age, gender, arm length, illness history, room temperature, humidity, air pressure, air flow rate, ambient light intensity, or the like, or a combination thereof.

In step 220, data may be generated based on the acquire information. Merely by way of example, a physiological parameter of interest may be calculated based on the physiological signals acquired in step 210. During the generation process, at least some of the acquired information may be pretreated, recognized, calculated, and calibrated. The operations may be performed by the measuring device 110, the health information management engine 120, or the terminal 130. In this step, various data may be generated, including, for example, a heart rate value based on ECG signals, a pulse rate value and a blood oxygen saturation level based on PPG signals, a body temperature value based on temperature signal, a blood pressure value based on ECG signals and PPG signals, or the like, or a combination thereof. The generated data may be analyzed in step 230. It should be noted that, in some embodiments, after the generation process or during the generation process, a new acquisition may be performed in step 210. In some embodiments, the generated data may be outputted in step 250.

The generated data may be analyzed in step 230. The analysis may be performed by the measuring device 110, the health information management engine 120 or the terminal 130. During the analysis process, some analysis models (e.g., a predefined analysis model), or some calculation algorithms (e.g., statistical analysis, threshold method) may be used. Via the analysis, various analysis results may be generated including, for example, new constructed analysis models, statistical analysis results regarding subject's health condition, abnormalities in the information or the generated data, or the like, or a combination thereof.

A health condition of the subject may be evaluated in step 240 based on the analysis results. A health condition evaluation may be generated. The evaluation may be presented in the form of an image, a text report, an audio information, video, a graph, a haptic effect, or the like, or a combination thereof. In some embodiments, the evaluation may indicate whether a health issue may be present or possibly present (see FIG. 22). In some embodiments, a recommendation may be generated based on the evaluation (e.g., health tips, a contraindication regarding a specific medicine or a treatment, or the like, or a combination thereof). The health condition evaluation may be carried out by the health information management engine 120 or the terminal 130. In some embodiments, the generation process (step 220), the analysis process (step 230) and the evaluation process (step 240) may be performed sequentially or simultaneously. In some embodiments, after the evaluation process or during the evaluation process, a new acquisition process may be performed in step 210.

Some information or data may be outputted in step 250. The outputted information or data may include, for example, physiological information including hear rate, blood pressure, blood oxygen saturation information, body temperature, or the like; analysis results generated in step 230; health condition evaluation information generated in step 240, or the like, or a combination thereof. The information or data may be outputted to a terminal 130, a local or a remote server (e.g., the health information management engine 120), or an external device (e.g., a medical device). In some embodiments, the analysis process may be carried out in a terminal 130-1, and a portion of or all of the information or data may be outputted to a related terminal 130-2 (e.g., a terminal having an access privilege). In some embodiments, an identity verification may be carried out before the output process.

This description is intended to be illustrative, and not to limit the scope of the present disclosure. Many alternatives, modifications, and variations will be apparent to those skilled in the art. The features, methods, and other characteristics of the exemplary embodiments described herein may be combined in various ways to obtain additional and/or alternative exemplary embodiments. For example, a pretreatment step may be added before step 220. In the pretreatment step, the acquired signals may be pre-treated, in order to reduce or remove noise or interferences in the signals originally acquired. Another pretreatment step may be added before step 230, e.g., data integration, data checking or data cleaning. One or more other optional steps may be added in the exemplary process illustrated in FIG. 2. Examples of such steps may include storing or retrieving the acquired information, generated data, analyzed data, and health condition.

Figure 3:
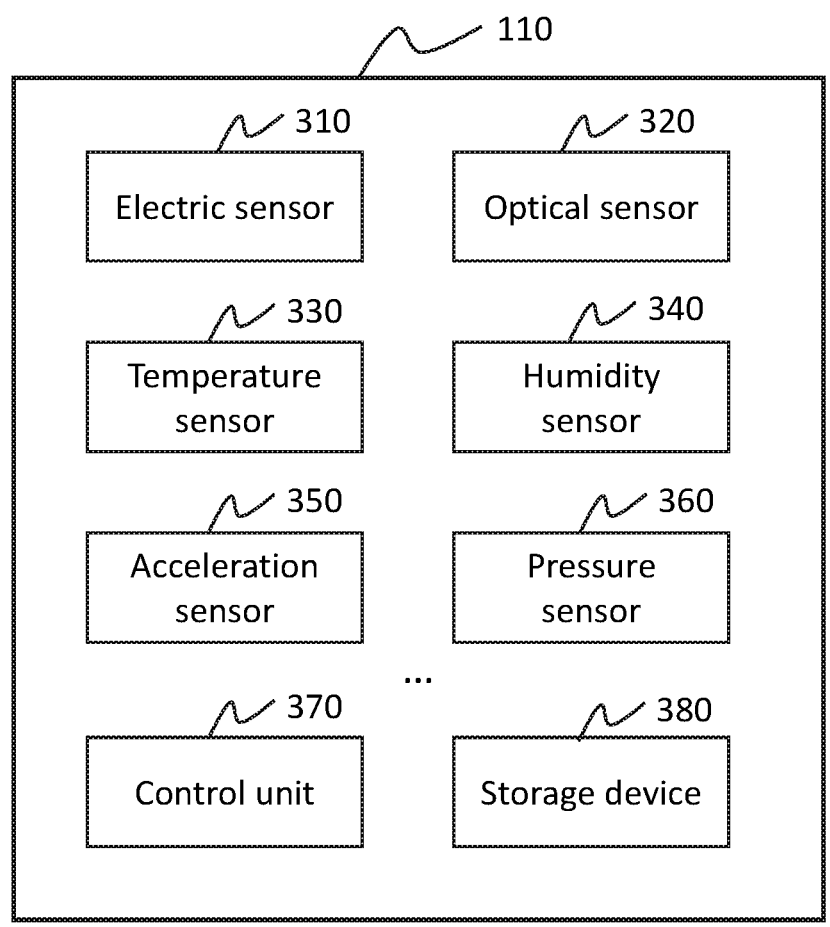
FIG. 3 depicts an exemplary block diagram of a measuring device according to some embodiments of the present disclosure.

FIG. 3 is a block diagram illustrating an architecture of a measuring device 110 according to some embodiments of the present disclosure. As illustrated in FIG. 3, the measuring device 110 may include a plurality of sensors of various types, for example, an electric sensor 310, an optical sensor 320, a temperature sensor 330, a humidity sensor 340, an acceleration sensor 350, a pressure sensor 360, or the like. The measuring device 110 may further include a control unit 370 and a storage device 380. The signal acquired by a measuring device 110 may be transmitted to and/or stored in the storage device 380, the terminal 130, the database 140, or the health information management engine 120.

The measuring device 110 may be configured to monitor, detect, and/or acquire one or more physiological signals, information of the subject, and/or one or more environmental signals or information. Exemplary physiological signals may include an ECG signal, a PPG signal, a heart rate, a heart rate variation (HRV), a pulse rate, a pulse rate variation, a blood pressure, a blood oxygen level, body fat, respiration, or the like, or a combination thereof. Exemplary information of the subject may include personal data of a subject, dynamic information relating to the subject, environmental information, or the like, or a combination thereof. The personal data may include static personal data and dynamic personal data described elsewhere in the present disclosure. Dynamic information may include information relating to the subject at or around the acquisition time. Exemplary dynamic information may include motion speed, motion path, or the like, or a combination thereof. Exemplary environmental information may include surrounding temperature, humidity, ultraviolet intensity, or the like, or a combination thereof.

Merely by way of example, the electric sensor 310 may be configured for acquiring an ECG signal of the subject. The electric sensor 310 may include a plurality of electrodes located on different locations on the body of the subject. The electrodes may be made of, e.g., a metal. The electrodes may be arranged in an electrocardiographic lead placement. For example, the electrodes may be arranged in a 12-lead form, a 5-lead form, a 3-lead form, or the like. The electrodes may constitute some leads measuring the electrical potential differences between pairs of body points, then an overall magnitude of the heart's electrical potential may be measured. The acquired ECG signal may be transmitted to and/or stored in the storage device 380, the terminal 130, the database 140, or the health information management engine 120.

Merely by way of example, the optical sensor 320 may be configured for acquiring a PPG signal or a pulse related signal of the subject. The optical sensor 320 may include an emitting end for emitting a light and a receiving end used for acquiring a signal resulting from the emitted light. The acquired signal may be used to derive or provided a PPG value. For brevity, a PPG signal, as used herein, may refer to the derived PPG value, or the acquired signal used to derive the PPG value. The light may be a light of a suitable wavelength including, for example, red, green, blue, infrared, purple, yellow, orange, ultraviolet, or the like, or a combination thereof. The spectrum of the light may include visible spectrum, infrared spectrum, far-infrared spectrum, ultraviolet spectrum, or the like, or a combination thereof. The receiving end may be a detector that may detect the quantity of the received signals and/or a change thereof, and/or provide a corresponding output (for example, an electrical signal or an optical signal). The signal acquired by the optical sensor 320 may be transmitted to and/or stored in the storage device 380, the terminal 130, the database 140, or the health information management engine 120.

Merely by way of example, the temperature sensor 330 may be configured for sensing the body temperature of the subject or the surrounding temperature. The temperature sensor 330 may be placed on a plurality of body locations of the subject. The temperature sensor 330 may be used for sensing a real time temperature change of the subject and the surrounding environment. Merely by way of example, the humidity sensor 340 may be configured for sensing the humidity of or around the subject or the surrounding environment. Similarly, the humidity sensor 380 may be placed on a plurality of body locations of the subject and may detect a real time change of the humidity of or around the subject and the surrounding environment. The acquired temperature signals and humidity signals may be transmitted to and/or stored in the storage device 380, the terminal 130, the database 140, or the health information management engine 120.

Merely by way of example, the acceleration sensor 350 may be configured for detecting an acceleration or a speed of the subject while under motion. In some embodiments, the detected acceleration or speed information may be transmitted to the control unit 370. The control unit 370 may analyze and process the information to generate one or more motion related information. The motion related information may include a real time speed, path, steps, time, or the like, or a combination thereof. In some embodiments, the acceleration sensor 350 may be used as a pedometer. The pedometer may be used to monitor the walking steps of the subject in real time. The signal acquired by the acceleration sensor 350 may be transmitted to and/or stored in the storage device 380, the terminal 130, the database 140, or the health information management engine 120.

Merely by way of example, the pressure sensor 360 may be configured for detecting a pressure change while the subject is contact with an object (e.g., ground, wall, or the like). The pressure sensor 360 may be located on a plurality of locations on the body of the subject. Merely by way of example, the pressure sensor 360 may be placed on the bottom of the foot, while the subject is in contact with the ground, a pressure signal may be generated and transmitted to the control unit 370, or the terminal 130, or the health information management engine 120. In some embodiment, a pressure change via time may be generated during motion of the subject. The signal acquired by the pressure sensor 360 may be transmitted to and/or stored in the storage device 380, the terminal 130, the database 140, or the health information management engine 120.

The control unit 370 may be configured for controlling one or more parameters regarding the operations of the sensors. Merely by way of example, a certain time interval may be set by the control unit 370 according to which a signal may be detected. In another example, different sensitivities may be set under different situations (e.g., motion or not). In a further example, a further signal may be generated by the control unit 370 based on the detected signals. In a still further example, the control unit 370 may control the transmitting of the signals from the measuring device 110 to the terminal 130 or the health information management engine 120. The storage device 380 may be configured for storing the detected signals. The storage device 380 may be any storage disclosed anywhere in the present disclosure. In some embodiments, the storage device 380 is unnecessary, the measuring device 110 may share a common storage with the system and other modules or units in the system.

The measuring device 110 may further may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured for connecting the measuring device 110 with any related external device, e.g., a charging device, a display device, a data exchange or storage device, or the like, or a combination thereof.

FIG. 4-A shows an exemplary block diagram illustrating a terminal 130 according to some embodiments of the present disclosure. As described in FIG. 1-A and FIG. 1-B, the system 100 may include a plurality of terminals (e.g., 130-1, 130-2, 130-3, . . . , 130-N). The terminal 130 may include an interaction unit 410, an identity verification unit 402, and a data generation unit 403. The data generation unit 403 may include a pretreatment unit 4031, a recognition unit 4032, a calculation unit 4033, and a calibration unit 4034. It should be noted that the units of the terminal 130 may be partially integrated in one or more independent modules or units.

The interaction unit 410 may be configured for receiving information from the measuring device 110, the health information management engine 120, the database 140, other terminals, other devices, or the like, or transmitting data or information to the measuring device 110, the health information management engine 120, the database 140, other terminals, other devices, or the like. In some embodiments, the interaction unit 410 may include a transceiver (not shown in FIG. 4-A) configured for receiving or transmitting information. In some embodiments, the interaction unit 410 may be configured to check whether the connections among the measuring device 110, the health information management engine 120, the database 140, or other terminals are fine. If the connections are fine, the receiving or transmitting described above may be performed; otherwise, the interaction unit 410 may provide an alert to the receiving device and/or the transmitting device, or set up a reminder to receive or transmit information later. In some embodiments, the interaction unit 410 may be configured to display or present the received information or the data generated by the terminal. In some embodiments, the interaction unit 410 may provide an interactive interface to register a user account or to establish a relationship with other user accounts. For example, the subject may log into an existing account and add an access privilege to the account for, e.g., a family member, a healthcare provider, a care provider, or the like, or a combination thereof. Different account user and their respective access privileges may be classified by labeling them as different classes or tiers of account users. For instance, different account users and their access privileges may be labeled as a family member, a healthcare provider, a care provider, etc. In some embodiments, the labeled accounts information may be stored in the identity verification unit 402, a storage in the terminal 130, the database 140, the health information management engine 120, or the like, or a combination thereof.

In some embodiments, a specific account user may have a specific access privilege. An access privilege may include, for example, a privilege to read some or all information relating to the subject, to update some or all information relating to a subject, or the like, or a combination thereof. The access privilege may be associated with or linked to a set of login credentials. Merely by way of example, the system may provide three tiers of access privileges. A first tier may include a full access privilege regarding information relating to a subject, allowing both receiving and updating information relating to a subject. A second tier may include a partial access privilege regarding information relating to a subject, allowing receiving and updating part of information relating to a subject. A third tier may include a minimal access privilege regarding information relating to a subject, allowing receiving part of or all information relating to a subject. Different login credentials may be associated with different access privileges to the information relating to a subject in the system. As used herein, updating may include providing information that does not exist in the system, or modifying pre-existing information with new information.

The identity verification unit 402 may be configured to determine whether a user other than the subject is allowed to visit the system or the terminal 130, or access information thereof relating to the subject. For example, if the terminal 130 receives a request to visit the terminal from a user other than the subject, the identity verification unit 402 may check whether and/or how the user account is labeled. If the user account is labeled, the identity verification unit 402 may give a specific permission according to its label. Otherwise, if the user account is not labeled, the identity verification unit 402 may deny the access request, push a notification to the user regarding the denial, provide a suggestion to the user to seek an access privilege, push a notification to the subject via the interaction unit 410 to report the access request by the user, remind the subject to add a label or to give a specific permission, or the like, or a combination thereof. In some embodiments, a user who has an appropriate access privilege may be allowed to visit the terminal freely at any time or semi freely with a limited access.

The data generation unit 403 may be configured to receive and process the information acquired from the measuring device 110. In some embodiments, the data generation unit 403 may include a pretreatment unit 4301, a recognition unit 4302, a calculation unit 4303, and a calibration unit 4304. The pretreatment unit 4031 may be configured to pretreat the acquired information. The pretreatment may be performed to reduce and remove noise or interferences in the original signals entering the terminal. The recognition unit 4032 may be configured to analyze the acquired information to recognize or identify a feature. Exemplary features of the acquired information may include waveform, characteristic points, peak points, valley points, amplitude, time intervals, phase, frequencies, cycles, or the like, or any combination thereof. The calculation unit 4303 may be configured to perform various calculations to determine, a physiological parameter of interest, a physiological condition, or the like, or a combination thereof, based on the features recognized by the recognition unit 4302. The calibration unit 4304 may be configured to perform a calibration. More detailed descriptions regarding the data generation process may be found in International Application No. PCT/CN2015/083334 filed Jul. 3, 2015.

As illustrated in FIG. 4-B, the terminal 130 may include a data storage 401, a processor 405, and a communication unit 406. One or more of the interaction unit 410, the identity verification unit 402, and the data generation unit 403 may be implemented on the processor 405 and the data storage 401 of the terminal 130. The information into and from the terminal (for example, measured signals, calculated data, analysis results, login information associated with or identifying an access privilege, etc.) may be communicated via the communication unit 406. The processor 405 may be configured to control a parameter regarding operations performed by the units or modules in the terminal 130. The parameter may include an ON/OFF condition, a switching frequency of ON or OFF, a time interval between ON and OFF, a time interval for data generation, a time interval for receiving data or transmitting data, or the like, or a combination thereof. In some embodiments, the data storage 401 may be configured for storing the received information via the interaction unit 410, the data generated by the data generation unit 403, an intermediate result generated during any operation of the units. In some embodiments, the processor 405 may be configured for coordinating the communication and/or operations of the interaction unit 410, the identity verification unit 402, and the data generation unit 403.

This description about the terminal is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, in some embodiments, the terminal and a measuring device may be integrated in an independent device. The independent device may be configured to receive and process the measured signals, estimate a physiological parameter of interest based on the measured physiological signals, display or present a result including the physiological parameter of interest.

FIG. 4-C shows an exemplary process for processing information by or on the terminal 130 according to some embodiments of the present disclosure. Beginning in step 411, information may be received. The information may be received from the measuring device 110, the health information management engine 120, or the database 140. The receiving may be performed by the interaction unit 410. The received information may include the physiological information of a subject, environmental information relating to the ambient surrounding the subject at or around the acquisition time of at least some of the physiological information of a subject, information provided by the subject or a user other than the subject. The information may include a PPG signal, an ECG signal, a pulse rate, a heart rate, a heart rate variation, blood oxygen saturation, respiration, muscle state, skeleton state, a brainwave, a blood lipid level, a blood sugar level, the height, the weight, the age, gender, the body temperature, the arm length, an illness history, the room temperature, humidity, air pressure, an air flow rate, the ambient light intensity, or the like, or a combination thereof.

Data may be generated in step 412 based on at least some of the received information. The data generation process may be performed by the data generation unit 403. The generated data may include physiological parameters of interest of the subject, including, a blood pressure, a pulse rate, a pulse rate variation, a heart rate, a heart rate variation, blood oxygen saturation, or the like, or a combination thereof. In some embodiments, the data generation process may include operations, including pretreating the received information, recognizing features of the acquired information, calculating a physiological parameter based on the recognized features, and performing a calibration. In some embodiments, a parameter of the generation process may be controlled in step 413. The parameter may include a time interval for data generation, a pretreatment method, a calculation model, a set of calibration data, or the like, or a combination thereof. The control process may be performed by the processor 405.

The generated data may be stored in step 414. The data may be stored in the data storage 406 in the terminal 130, the database 140, or any storage device disclosed anywhere in the present disclosure. The data may be visited or reviewed by other terminals and/or other modules or units. In some embodiments, if a user (for example, the subject, or someone other than the subject) requests to access the terminal 130 or information stored thereon or accessible therefrom (for example, information relating to the subject that is store in the database 140 and accessible from the terminal 130), an identity verification process may be performed in step 415. The identity verification may be performed by the identity verification unit 402. It may determine whether the user has an access privilege (see FIG. 4-A). For example, if a user other than the subject, e.g., a user having a family relationship, or a doctor-patient relationship with the subject, may need to access the information relating to the subject to review the health condition of the subject, and his/her identify may be verified, and thus he may access the information via the interaction unit 410. More detailed descriptions regarding the identity verification may be found in FIG. 21. In step 416, the data may be transmitted to the health information management engine 120, or a related terminal (e.g., the terminal 130-2).

It should be noted that the above description about the processing information of a terminal is merely an example, not intended to be limiting. Obviously, to those skilled in the art, after understanding the basic principles of processing information, the process may be modified or varied without departing from the principles. The modifications and variations are still within the scope of the current disclosure described above. For example, in some embodiments, the order of performing the steps may be changed, in some embodiments, some steps may be omitted. In some embodiments, the intermediate results and the final results of each step may be stored. For example, the received information in step 411 may be stored for further use. In some embodiments, the identity verification may be performed before receiving information, for example, the subject may first need to log into the system, and then the terminal 130 may receive information.

FIG. 5-A is a block diagram illustrating an architecture of the health information management engine 120 according to some embodiments of the present disclosure. The health information management engine 120 may include a data management unit 502, a data analysis unit 503, and a data mining unit 504. The health information management engine 120 may be connected with or otherwise communicate with, e.g., the measuring device 110, the terminal 130, the database 140 through the network 150. The health information management engine 120 may be configured to receive, store, manage, analyze, and/or deliver data.

The data management unit 502 may be configured for managing the received data. The data management may include collection, classification, organization, translation, indexing, encoding, decoding, encryption, decryption, or the like, or a combination thereof. Merely by way of example, when the received data is from a newly registered terminal, the data management unit 502 may create a new data sheet for the terminal, or integrate the new data into an existing data sheet. In another example, when a terminal deregisters from the health information management engine 120, the data management unit 502 may perform a data change, a data backup or deletion in respect to the terminal. In some embodiments, the data management unit 502 may be configured for managing real-time and concurrent access of data from one or more terminals 130, or various components, units, or modules of the system 100. For example, if a plurality of terminals, modules or units (e.g., the terminal 130, a server (e.g., the health information management engine 120), the data analysis unit 503, or the like) simultaneously request to access a same set of data, the data management unit 502 may function so that the data may be accessed orderly. In some embodiments, the data management unit 502 may include a pretreatment unit (not shown). The pretreatment unit may be configured to pretreat the received data. The pretreatment may be performed to remove obvious flaws, correct inaccurate records, delete insignificant outliers, selectively remove identification information, or the like, or a combination thereof. As used herein, "selectively remove" may indicate that some identification information may be removed before the associated data are stored or analyzed. For instance, some or all identification information of a subject (for example, name, birthday, social security number, national identification number, home address, contact information, etc.) may be removed before a physiological parameter of interest and/or associated physiological signals or other information relating to the subject is pooled for analysis for a sub-population to which the subject is considered belonging; some identification information may be reserved (for example, age, gender, health history, etc.) in such an analysis relating to the sub-population; all identification information may be reversed for the record of the subject for his personal use or use by a user other than the subject including, for example, a healthcare provider, a care provider, a family member.

The data analysis unit 503 may be configured for analyzing the received data. The data analysis unit 503 may be connected with or otherwise communicate with the data management unit 520 and/or the data mining unit 504. The data analysis unit 503 may include an internal structure similar to the data generation unit 403 as illustrated in FIG. 4-A and described elsewhere in the present disclosure.

In some embodiments, the analysis performed by the data analysis unit 503 may include calculating a parameter based on the received data, extracting a feature of the data, refining useful information from a batch of data, generating a relationship among the received data, or the like, or a combination thereof. Exemplary methods may include statistical analysis methods, (e.g., regression analysis, factor analysis, clustering, recognition analysis, or the like, or a combination thereof) and intelligent analysis methods (e.g., neural network, a genetic algorithm, a rough set, or the like, or a combination thereof). In an exemplary context of a big data analytics, exemplary analysis methods may also include a bloom filter, hashing, indexing, a trie tree, parallel computing, or the like, or a combination thereof. In some embodiments, the received data may have been pre-treated before it is analyzed in the data analysis unit 503. In some embodiments, the pre-treatment may be performed by the data analysis unit 503. In some embodiments, the pre-treatment may be performed by the data management unit 502. In some embodiments, some pre-treatment may be performed by the data management unit 502, and some pre-treatment may be performed by the data analysis unit 503.

The data analysis may be performed based on an analysis model. As used herein, an analysis model may refer to a function of a dependent variable (e.g., health condition, a prediction, a recommendation) and an independent variable (e.g., measured physiological signals, information of a subject, health related information, environmental information, history data, statistical information, or the like) (see, for example, Equation 1). For example, a probability of hypertension for a subject may be estimated according to a statistical model based on the subject's historical blood pressure values. As another example, a risk of gastric cancer for a subject may be evaluated based on an association rule that may indicate the relationship between gastric cancer and a dietary history. In some embodiments, the analysis model may be a predefined model pre-stored in the health information management engine 120 or the database 140, or a predefined model obtained from an external data source (e.g., a server). In some embodiments, the analysis model may be a newly generated model according to data obtained by the data mining unit 504. The model may be set, modified, and updated by the health information management engine 120.

The data analysis may be performed at an individual level, a group level, or both. As used herein, the individual level may refer to that the analysis may be performed focusing on an individual subject. The group level may refer to that the analysis may be performed focusing on a plurality of subjects and related information including group classification, division of susceptible population, or the like, may be taken into account. In some embodiments, during an individual level analysis, some information from a group level analysis may be used.

An analysis result may be generated after the analysis process. The analysis result may include, health related information including health condition of the subject, prediction of potential risks of sub-health, disease information, obesity or not, or the like; a health related recommendation including, e.g., health tips about daily life, alerts regarding an acute health problem, or the like, or a combination thereof. Merely by way of example, while an abnormal condition occurs, an alert may be generated and transmitted to a related member (e.g., a member having a family relationship, a relative relationship or a doctor-patient relationship with the subject, or a healthcare provider, a hospital, an a police department, a surveillance company, or the like, or a combination thereof). As used herein, an abnormal condition may be that at least some of the received data or a physiological parameter of interest exceeds a threshold. As used herein, "exceed" may be larger than or lower than a threshold. Merely by way of example, if the received blood pressure exceeds a threshold (e.g., the value of SBP is higher than 140 mmHg, the value of DBP is lower than 60 mmHg), an alert may be generated and transmitted to a related member.

The analysis, or some operations of the analysis, may be performed in real time, i.e. at or around the acquisition time. The analysis, or some operations of the analysis, may be performed after a delay since the data is received. In some embodiments, the received data is stored for analysis after a delay. In some embodiments, the received data is pre-treated and stored for further analysis after a delay. The delay may be in the order of seconds, or minutes, or hours, or days, or longer. After the delay, the analysis may be triggered by an instruction from a subject or a user other than the subject (e.g., a doctor, a health-care provider, a family member relating to the subject, or the like, or a combination thereof), an instruction stored in the system 100, or the like, or a combination thereof. Merely by way of example, the instruction stored in the system 100 may specify the duration of the delay, the time the analysis is to be performed, the frequency the analysis is to be performed, or the like, or a combination thereof.

The data mining unit 504 may be configured for extracting information and knowledge from a data source. The data source may be the database 140, a remote server, a paid database, or the like, or a combination thereof. The data mining process may include acquiring a plurality of data, constructing an analysis model based on the acquired data, modifying an available analysis model, or the like, or a combination thereof. Merely by way of example, an analysis model regarding a relationship between lung cancer and air quality may be constructed based on a plurality of data including outdoor time, rest time, respiratory state, or the like, or a combination thereof. The extracted data, or the constructed analysis model may be transmitted to the health information management engine 120, the terminal 130, and/or the database 140.

As illustrated in FIG. 5-B, the health information management engine 120 may include a data storage 501, a processor 505, and a communication unit 506. One or more of the data management unit 502, the data analysis unit 503, and the data mining unit 504 may be implemented on the processor 505 and the data storage 501 of the terminal 130. The information into and from the health information management engine 120 may be communicated via the communication unit 506.

The data storage 501 may be configured for storing data, analysis models, parameters or factors of the analysis models, or the like. The storing may be performed in real time or after a time delay. In some embodiments, the data storage 501 may include one or both of a system storage (for example, a disk) that is provided integrally (i.e. substantially non-removable) with the server, and a removable storage that is removably connectable to the server via, for example, a port (for example, a USB port, a firewire port, etc.) or a drive (for example, a disk drive, etc.). The data storage 501 may include or be connectively operational with one or more virtual storage resources (for example, cloud storage, a virtual private network, and/or other virtual storage resources). The data storage 501 may include a hard disk, a floppy disk, selectron storage, RAM, DRAM, SRAM bubble memory, thin film memory, magnetic plated wire memory, phase change memory, flash memory, cloud disk, or the like, or a combination thereof. The data storage 501 may be any storage device disclosed anywhere in the present disclosure. In some embodiments, the data storage 501 may further include an access interface through which the data may be searched and/or analyzed.

The processor 505 may be configured for executing computer programs, computations, analyzing data or information, controlling a parameter regarding any operation performed by the modules or units of the health information management engine 120. In some embodiments, the computations may include concurrent computation, parallel computation, distributed computation, centralized computation, or the like, or a combination thereof. One or more modules or units of the health information management engine 120. In some embodiments, the health information management engine 120 may share a processor with another module or unit of the system 100. See relevant descriptions regarding a processor elsewhere in the present disclosure.

The communication unit 506 may be configured for receiving or transmitting data, information, signals, requests, or instructions between the health information management engine 120, the terminal 130, the database 140, or an external data source, or a combination thereof. The receiving and transmitting procedure may be performed simultaneously or asynchronously. The communication unit 506 may include a connection check unit (not shown) used for detecting whether the connection is working properly, and/or an identity verification unit (not shown) used to ensure the legitimacy and security of communication. Merely by way of example, while the transmitting is prepared, the connection check unit (not shown) may check whether the connection between the health information management engine 120 and a receiver (e.g., the terminal 130) is working properly, or whether the receiver (e.g., the terminal 130) is available to receive data or information. In some embodiments, the identity verification unit may further verify the identity information; if the identity verification is not satisfied, or the identity information is outdated or not recognized, the communication request may be denied. A notification may be generated based on an authorized or successful communication, or a denied or unsuccessful communication. See relevant description elsewhere in the present disclosure.

This description is intended to be illustrative, and not to limit the scope of the present disclosure. Many alternatives, modifications, and variations will be apparent to those skilled in the art. The methods, algorithms, features, and other characteristics of the exemplary embodiments described herein may be combined in various ways to obtain additional and/or alternative exemplary embodiments. For example, the data mining unit 504 may be integrated into the data analysis unit 503. Similarly, any unit may be integrated in any other unit. Operations performed by any unit may be performed by any other unit. In some embodiments, any unit may include one or more sub-units in which other methods or algorithms may be applied. The methods or algorithms applied in different unit may be different, partially different, or the same.

FIG. 5-B is a flowchart of an exemplary process for analyzing data in the health information management engine 120 configured as shown in FIG. 5-A, according to some embodiments of the present disclosure. Beginning in step 507, data may be received from the measuring device 110, the terminal 130, the database 140 (see FIG. 1-A and FIG. 1-B), and an external data source. The data transmission may be achieved via the communication unit 506. In some embodiments, an identity verification may be performed before data transmission. If the identity verification is satisfactory, the data transmission may be executed. The received data may include physiological signals (e.g., ECG signals, PPG signals, temperature signals, or the like), physiological parameters of interest of the subject (e.g., blood pressure, blood oxygen saturation, or the like), basic information of the subject (e.g., age, gender, height, or the like), environmental signals (temperature, humidity, atmospheric pressure, etc.), or the like, or a combination thereof.

In step 508, the received data may be stored. The data may be stored in the storage 501, the database 140, or any storage device disclosed anywhere in the present disclosure. In step 509, the received data may be managed. The data management may be performed by the data management unit 502. The data management may include collection, classification, organization, translation, indexing, encoding, decoding, encryption, decryption, or the like, or a combination thereof. In some embodiments, the data management may be performed according to a criterion. The criterion may include a rule regarding data combination, data classification, or the like, and/or a standard regarding data array, data format, data structure, or the like. The criterion may further include a standard regarding data storage, data processing, and/or data analysis. The criterion may be set according to a default setting of the system (e.g., an industrial standard, etc.), or may be customized by the subject (e.g., classified by time, combined by physiological parameter category, screened by data type, or the like). The criterion may be set by an institution or user that has the authority to manage the data relating to the subject. Exemplary institutions or users may include a hospital, a research institute, a healthcare provider, a care provider, etc.

After the data management is performed, the process may proceed to step 510 in which a determination may be made as to whether a data mining is to be performed. In some embodiments, the determination may be made by the system default, or based on instructions by the subject or a user other than subject. Merely by way of example, the data mining may performed in a predetermined time interval (e.g., 30 minutes, 1 hours, 5 hours, 10 hours, 12 hours, 24 hours, or the like). In another example, the data mining may be performed at a particular time point of a day (e.g., 6:00, 12:00, 21:00, 0:00, or the like). As a further example, the data mining may be performed automatically while the system is in an idle state or during an off-peak time. In a further example, the determination may be made based on the requests (if any) received in step 507. In still a further example, if there is no proper analysis model available (see, for example, relevant description regarding FIG. 5-A), a data mining process may be needed.

If a determination is made not to perform a data mining, the process may proceed to step 511. In step 511, the data may be analyzed. The data analysis may be performed by the data analysis unit 503 based on an analysis model. As used herein, an analysis model may refer to a function of a dependent variable (e.g., health condition, a prediction, a recommendation) and an independent variable (e.g., measured physiological signals, information of a subject, health related information, environmental information, history data, statistical information, or the like) (see, for example, Equation 1). The analysis model may be stored in the health information management engine 120 or acquired from an external data source. The model used for analysis may be chosen based on the requests (if any) received in step 507. For example, when the requests indicate an evaluation of the blood pressure, a blood pressure evaluation model may be used. During the analysis process, partial or all of the data analysis operations may be performed by other devices. Merely by way of example, the data may be transmitted to another device or system (e.g., a remote server, a remote database, a terminal, etc.) to perform external calculation or analysis, and the analysis results or intermediate results may be sent back to the health information management engine 120 for further analysis.

If a determination is made to perform a data mining, the process may proceed to step 512. In step 512, a data mining process may be performed. The data mining process may be performed by the data mining unit 504. The data mining process may include acquiring a plurality of data, constructing an analysis model based on the acquired data, modifying an available analysis model, or the like, or a combination thereof. For example, during a data mining process, the data may be processed in combination with other data (e.g., data acquired from an external data source (e.g., a local or remote server, a local or remote database, or the like)). In some embodiments, the data may be pretreated before the data mining process, e.g., data integration, data checking and data cleaning.

In step 513, the analysis results may be provided to one or more terminals 130. This procedure may be performed by the communication unit 506. The analysis result may include, health related information including health condition of the subject, a prediction regarding a potential risk of sub-health, disease information, obesity or not, a recommendation regarding health (e.g., health tips about daily life, an alert regarding an acute health problem, etc.), or the like, or a combination thereof. In some embodiments, the connection between the health information management engine 120 and terminal 130 may be checked before transmitting the analysis results. In some embodiments, the analysis results may be transmitted simultaneously or sequentially to a plurality of terminals 130 according to the verified identities.

While the foregoing has described what are considered to constitute the present disclosure and/or other examples, it is understood that various modifications may be made thereto and that the subject matter disclosed herein may be implemented in various forms and examples, and that the disclosure may be applied in numerous applications, only some of which have been described herein. Those skilled in the art will recognize that present disclosure are amenable to a variety of modifications and/or enhancements. For example, the data mining process may be unnecessary, or it may be executed in the data analysis step 511. The data mining process and data analysis process may be performed simultaneously or concurrently. The data may be partially processed through the data analysis step 511, and partially processed through the data mining step 512. Additionally, the analysis results may be partially provided to terminals 130 in real time, and the rest of the analysis results may be provided with a time delay, as the data mining process may be time consuming.

Figure 6:
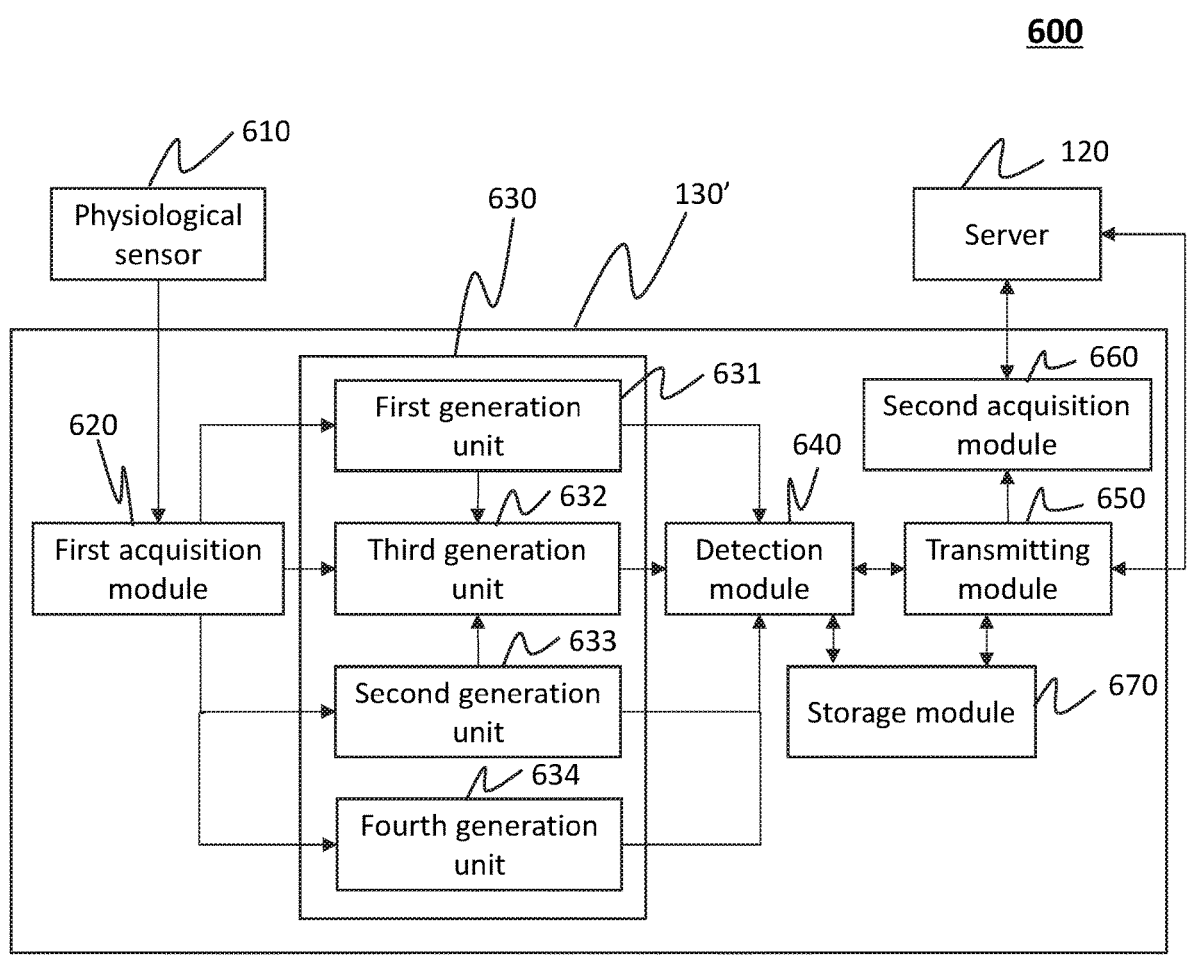
FIG. 6 is a block diagram illustrating the architecture of an exemplary system for health monitoring according to some embodiments of the present disclosure.

FIG. 6 is a block diagram of an architecture of an exemplary system 600 according to some embodiments of the present disclosure. The system 600 is an illustrative embodiment of the system 100 described in FIG. 1. The system 600 may include a physiological sensor 610, a terminal 130', and a health information management engine 120.

The physiological sensor 610 may be configured for acquiring a plurality of physiological signals or information of the subject. The physiological sensor 610 may be an integrated sensor that may measure multiple signals, or a plurality of separate sensors including, such as, an electric sensor, an optical sensor, a temperature sensor, or the like, or a combination thereof. As illustrated in FIG. 3, a plurality of sensors of various types may be integrated or include in the physiological sensor 610. In some embodiments, the physiological sensor 610 may be integrated in the terminal 130'. In some embodiments, the physiological sensor 610 may be an external monitor, such as a clinical or a household device.

The terminal 130' is an illustrative embodiment of the terminal 130 described in FIG. 1. The terminal 130' may be a smart phone, a tablet, a personal computer, or the like, or a combination thereof. The terminal 130' may include a first acquisition module 620, a generation module 630, a detection module 640, a transmitting module 650, a second acquisition module 660, and a storage module 670. The modules may be connected or communicate with each other via a wired connection or wirelessly. Two or more of the modules may be integrated into an independent component that may achieve more than one function or operation. In some embodiments, anyone of the modules may be integrated into a component other than the terminal 130'.

The first acquisition module 620 may receive one or more physiological signals or information from the physiological sensor 610. In some embodiments, the first acquisition module 620 may be a cache device. The received signals or information may be cached in the first acquisition module 620 and be retrieved if needed. The generation module 630 may be configured for generating one or more physiological parameters of interest of the subject. The generation module 630 may include a first generation unit 631, a second generation unit 632, a third generation unit 633, and a fourth generation unit 634. The four generation units are provided only for illustration purposes, the number of the generation units may be fewer or more, such as, one, two, five, six, or the like.

In some embodiments, the first generation unit 631 may be used for generating an ECG signal, a heart rate, a heart rate variation (HRV), or the like, or a combination thereof. The second generation unit 632 may be used for generating a pulse rate value, a PPG signal, a pulse rate variation, a blood oxygen level, or the like, or a combination thereof. The third generation unit 633 may be used for generating a blood pressure information based on the results generated by the first generation unit 631 and the second generation unit 632. More detailed descriptions regarding the estimation or calculation of blood pressure may be found in International Application No. PCT/CN2015/083334 filed Jul. 3, 2015. The fourth generation unit 634 may be used for generating a temperature value of the subject. In some embodiments, other physiological parameters of interest may be generated including, e.g., myoelectricity information, respiratory, body fat, blood viscosity, arterial stiffness, or the like, or a combination thereof. In some embodiments, a health related status of the subject may be generated based on the detected signals or information, e.g., stress level, emotional state, fatigue level, or the like, or a combination thereof.

The detection module 640 may be configured to detect whether the connection or the network status is fine. The detection operation may be performed in real time, or may start automatically based on instructions from the system or provided by the subject. In some embodiments, if the connection is fine, the generated physiological parameters of interest or physiological information may be transmitted, via the transmitting module 650, to the health information management engine 120 or the second acquisition module 660. In some embodiments, if the connection is bad or limited, the generated physiological parameters of interest or physiological information may be stored in the storage module 670, and may be transmitted after the connection restores or is established.

The transmitting module 650 may be configured to transmit the generated physiological parameters of interest or physiological information to the health information management engine 120 to be processed or analyzed; to the second acquisition module 660 to be visited or loaded by other terminals. In some embodiments, the transmitting module 650 may be a transceiver used to transmit and receive data. In some embodiments, the transmitting module 650 may be integrated in any module or unit of the terminal 130'. In some embodiments, the terminal 130' may share a transmitting device with the system 600.

The second acquisition module 660 may be configured for receiving data or information from the health information management engine 120 and/or the transmitting module 650. The second acquisition module 660 may communicate with the health information management engine 120 in real time. In some embodiments, other terminals with proper access privileges may access the terminal 130'. The data or information to be accessed may be stored in the second acquisition module 660.

The terminal 130' may be connected to or communicate with other terminals via a wired connection or a wireless connection. In some embodiments, the terminal 130' and other terminals may be part of a network. Members with an access privilege in the network may access data of other members. The form of the access privilege may be invitation code, pass word, access privilege, identity authentication, user validation, or the like, or a combination thereof. Merely by way of example, a member in the network may have a user account. A member having a family relationship, a relative relationship, or a doctor-patient relationship with the subject may obtain an access privilege to access the information stored in the user account of the subject. In some embodiments, the member may access the information of the subject at any time based on his/her instructions (e.g., the member may log in his/her user account at any time). In some embodiments, for example, during an urgent situation, an alert or a reminder may be transmitted to one or more of a family member, a healthcare provider automatically. Merely by way of example, if the subject experiences a sudden change of a physiological parameter of interest, an alert may be generated and transmitted to a family member or a healthcare provider of the subject. In some embodiments, if the health condition of the subject is not good, a reminder or a recommendation (e.g., a reminder or recommendation regarding taking medicine, rest, adjusting a working schedule, or the like, or a combination thereof.) may be generated and transmitted to the members.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the first acquisition module 620 and the second acquisition module 660 may be integrated in an independent module. The storage module 670 is not necessary while any storage device in the system or an external storage may be used. The detection module 640 is not necessary while the detection may be performed by the subject manually.

Figure 7:
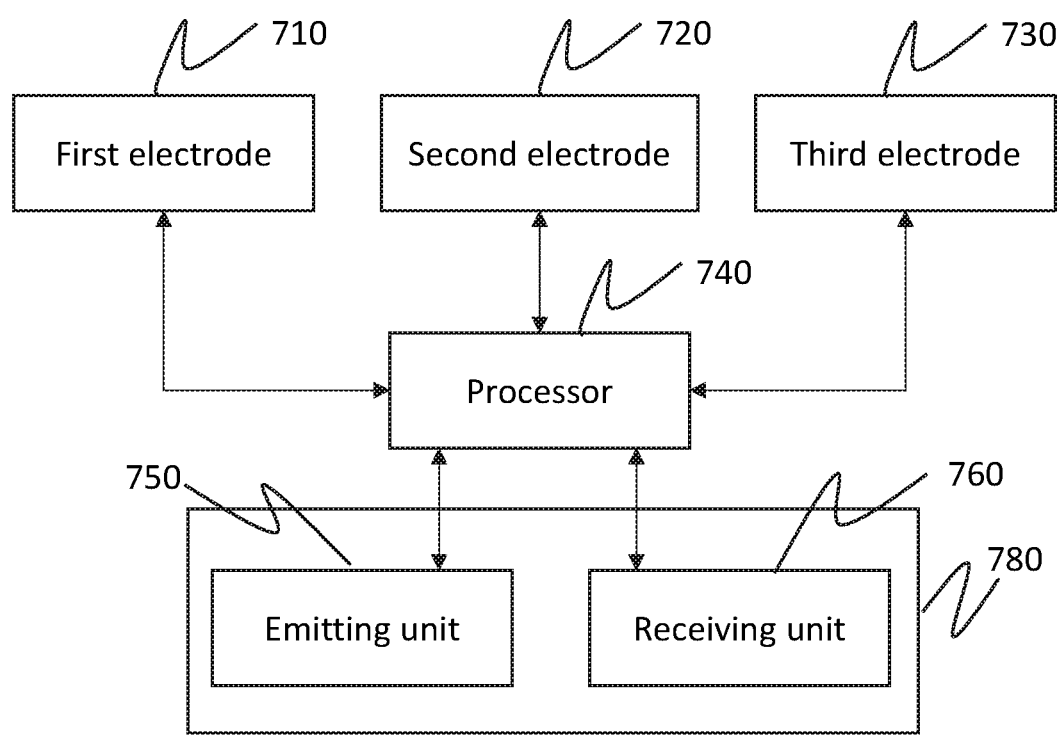
FIG. 7 shows an exemplary block diagram illustrating the architecture of a measuring device according to some embodiments of the present disclosure.

FIG. 7 shows an exemplary block diagram illustrating an architecture of a measuring device according to some embodiments of the present disclosure. As illustrated, the measuring device may include a first electrode 710, a second electrode 720, a third electrode 730, a processor 740 and an optical sensor 780. The optical sensor 780 may include an emitting unit 750 and a receiving unit 760. The three electrodes may be configured for acquiring an ECG signal of the subject, and the optical sensor 780 may be configured for acquiring a pulse related signal. The first electrode 710, the second electrode 720, the third electrode 730, and the optical sensor 780 may be connected with the processor 740 via a wired connection or a wireless connection.

The first electrode 710, the second electrode 720, and the third electrode 730 may be used to acquire physiological signals of the subject, e.g., an ECG signal, or physiological information including, for example, an ECG signal. In some embodiments, the first electrode 710, the second electrode 720, and the third electrode 730 may include a metal, an alloy, an electro-textile, a silver chloride, or the like, or a combination thereof. The electrodes may be placed on a plurality of locations on the body of the subject. The location may include the head, the neck, the chest, the abdomen, the upper arm, the wrist, the waist, the upper leg, the knee, the ankle, or the like, or a combination thereof. The electrodes may constitute a plurality of leads to detect potential differences between a pair of points on the body of the subject. An ECG signal may be acquired based on the potential differences. In some embodiments, more than three electrodes may be used, e.g., 10 electrodes may be configured to constitute a 12-lead measuring form to acquire ECG signals.

The optical sensor 780 may be used to acquire physiological signals of the subject, including, a pulse related signal (e.g., a PPG signal). The optical sensor 780 may include an emitting unit 750 and a receiving unit 760. The emitting unit 750 may emit radiation of wavelengths of, e.g., the visible spectrum, the infrared region, an ultraviolet spectrum, or the like, or a combination thereof. The receiving unit 760 may be used for receiving radiation reflected by the blood vessel of a subject based on the emitted radiation. In some embodiments, the emitting unit 750 is unnecessary, while an external light source may be used.

The acquired physiological signals of the subject may be processed and analyzed by the processor 740 to determine a physiological parameter of the subject including, for example, a blood pressure, a heart rate variation (HRV), level of fatigue, psychological pressure, stress tolerance of the subject, or the like, or a combination thereof. The determined physiological parameters of interest may be transmitted to the health information management engine 120 to be further processed and/or analyzed (refer back to FIG. 5 to see details). In some embodiments, the processor 740 may be configured for controlling a parameter of the acquisition process of the signals, e.g., sampling frequency, sampling time interval, or the like, or a combination thereof. In some embodiments, the processor 740 may include a memory used for storing the acquired signals and the estimated or calculated data. The processor 740 may be any processor or module that may perform these functions or operations disclosed elsewhere in the present disclosure.

It should be noted that the above description about the measuring device is merely an example, not intended to be limiting. Apparently for persons having ordinary skills in the art, numerous variations and modifications may be conducted under the teaching of the present disclosure. However, those variations and modifications may not depart the protecting scope of the present disclosure. For example, in some embodiments, the measuring device may include other modules or units, e.g., a positioning unit (for example, a GPS receiver or location sensor) that may be used to position the subject who wears the ring 1300, or help the subject navigate. The location information may be transmitted to, for example, one or more terminals 130 and/or the health information management engine 120, a user other than the subject (for example, a family member, a healthcare provider, a care provider, etc.), or the like, or a combination thereof. The transmission may be performed in real time, after a delay, periodically, triggered by a triggering event (for example, the subject leaves a pre-defined area), or the like, or a combination thereof.

FIG. 8-A through FIG. 8-D show an exemplary smart watch which is an exemplary measuring device illustrated in FIG. 7, according to some embodiments of the present disclosure. As illustrated in FIG. 8-A, the smart watch may include a watch header 810, one or more watch straps 820 together with the first electrode 710, the second electrode 720 and the third electrode 730 (not shown in FIGS. 8-A through 8-D; see FIG. 7). The processor 740 may be integrated in the watch header 810.

As shown in FIG. 8-B, the first electrode 710 may be connected or communicate with the processor 740 via an electric wire 830. The electric wire 830 may be flexible and deformable, so that it may bend to accommodate the curvature of the wrist of the subject. The electric wire 830 may be laid in the watch strap 820. Similarly the second electrode 720 also may be connected or communicate with the processor 740 via the electric wire 830. The electric wire 830 may include a metal wire, e.g., a copper wire, an aluminum wire, a gold wire, a silver wire, or the like, or a combination thereof. The first electrode 710 and the second electrode 720 may be placed on the watch strap 820 as shown in FIG. 8-A. The material of the watch strap 820 may be metallic or nonmetallic. Exemplary nonmetallic material may include silica gel, plastic, leather, fabric, or the like, or a combination thereof. In some embodiments, the first electrode 710 and the second electrode 720 may be placed on the interior surface or the exterior surface of the watch strap 820. As used herein, the interior surface of the watch strap 820 may refer to the surface that may contact with the wrist of a subject, and the exterior surface of the watch strap 820 may refer to the side of the watch strap 820 opposite to the interior surface of the watch strap 820.

As shown in FIG. 8-D, there may be a hole 890 in the watch strap 820. The first electrode 710 may be placed in the hole 890. The hole 890 may be a through hole or not. Many ways may be used to fix the first electrode 710 in the watch strap 820. In some embodiments, as illustrated in FIG. 8-D, there may be a groove 891 on the side wall of the hole 890. The groove 891 may be a ring groove along the perimeter of the hole 890. As shown in FIG. 8-B and FIG. 8-D, there may be a cantilever 840 around the first electrode 710, and the side wall of the electrode 710 may be L-shaped. The cantilever 840 may fit the groove 891 of the hole 890, and therefore, the first electrode 710 may be fixed in the watch strap 820. In some embodiments, the cantilever 840 may include several pinholes 850 within it. In some embodiments, the second electrode 720 may be placed in another hole on the watch strap 820, and surrounded by another cantilever with the same structure with the cantilever 840. In some embodiments, the first electrode 710 and the second electrode 720 may be on the same side of the surface of the watch strap 820, both on the interior surface or both on the exterior surface. In some embodiments, the first electrode 710 and the second electrode 720 may be on the opposite sides of the surface of the watch strap 820 (e.g., the first electrode 710 is on the interior surface and the second electrode 720 is on the exterior surface, see FIG. 8-C).

In some embodiments, the smart watch may include two watch straps 820. One end of the watch straps 820 may be movably connected with the watch header 810. The connection may be rotatable or otherwise moveable with respect to the watch header 810 such that the watch straps 820 may rotate or move to accommodate the curvature of a wrist of the subject, or to facilitate the wearing or removing of the smart watch from the subject. The connection may include a hinged connection, a plug, an interlock, or the like, or a combination thereof. The other end of the watch straps 820 may be connected together by using an openable buckle (not shown in FIG. 8). The locking position may be adjustable by the subject according to size of the wrist. In some embodiments, the watch straps 820 may be made of an elastic material. In some embodiments, the watch straps 820 may be made of an elastic material and does not include an openable buckle.

In some embodiments, the watch strap 820 may be formed by using a mold. While casting, the first electrode 710 may be placed in the mold. The watch strap 820 may be formed by pouring a material including, for example, silica gel, plastic, or the like, or a combination thereof. The hole 890 and the groove 891 may be formed at the same time with the watch strap 820. Because of the pinholes 850 in the cantilever 840, there may be the same number of pillars 880 in the groove 891. The upper surface of the pillars 880 and the lower surface of the pillars 880 may contact the upper surface and the lower surface of the groove 891, respectively, as shown in FIG. 8-D. In some embodiments, as shown in FIG. 8-C and FIG. 8-D, there may be filled with an insulating component 860 between the first electrode 710 and the second electrode 720. The insulting component 860 may be used to prevent the first electrode 710 from conducting electricity with the second electrode 720. While casting the watch strap 820, the insulating component 860 also may be placed in the mold. Because of the pillars 880, there may be several gaps 870 in the insulting component 860. The gaps 870 may be used to hold the pillars 880.

In some embodiments, the first electrode 710 or the second electrode 720 may be fixed on the watch strap 820 by, for example, suturing. A suture line may be used to pass through the pinholes 850 in the cantilever 840 and the watch strap 820 in turn. In some embodiments, the first electrode 710 and the second electrode 720 may be fixed on the watch strap 820 using a glue. In some embodiments, the first electrode 710 and the second electrode 720 may be fixed on the watch strap 820 by pouring a material including, for example, silica gel, plastic, etc., when the watch strap 820 is formed. The second electrode 720 may be fixed on the watch strap 820 using, for example, a same method or a different method. Some other ways to fix also may be used, e.g., by clamping, by a magnetic method, or the like, or a combination thereof.

In some embodiments, the first electrode 710 and the second electrode 720 may be two-tier structures. In some embodiments, the first electrode 710 and the second electrode 720 may be made of one or more flexible materials to follow the curvature of the wrist of a subject. The first tier may be a conductive material including, for example, a metal, an alloy of a metal, or the like, or a combination thereof. The second tier lying on the first tier may be a material having a suitable characteristic including, for example, conductivity, resistance to corrosion, or the like, or a combination thereof. The second tier may contact the body or skin of a subject. Merely by way of example, the first tier may be copper, and the second tier may be gold-plated or silver chloride-plated.

In some embodiments, the smart watch may further include an optical sensor 780 (not shown in 8-A through 8-D; see FIG. 7). The optical sensor 780 may be configured to detect a pulse related signal of the subject. The optical sensor 780 may include an emitting end used for emitting a light exposed and facing the skin of the subject and a receiving end used for acquiring a signal resulting from the emitted light. The light may be a light of any suitable wavelength, e.g., red, green, blue, infrared, purple, yellow, orange, ultraviolet, or the like, or a combination thereof, and The optical sensor 780 may be located on the bottom of the watch header 810 and may be connected with the processor 740. As used herein, the bottom may refer to the surface that may contact the body or skin of a subject when the subject wears the smart watch as instructed.

In some embodiments, when a subject wears the smart watch on one hand, the third electrode 730 and the electrode placed on the interior surface (e.g., the first electrode 710) of the watch strap 820 may contact the body of the subject. When the subject puts the other hand on the electrode placed on the exterior surface (e.g., the second electrode 720) of the watch strap 820, the first electrode 710, the second electrode 720, the third electrode 730, and the subject body may form electrocardiographic leads or electrocardiographic circuits for acquiring an ECG signal. The optical sensor 740 may emit a light to the body or skin of the subject, and a pulse related signal may be acquired. The processor 740 may process the ECG signal to provide an ECG diagraph, and process the pulse related signal to provide a pulse signal diagraph. In some embodiments, the processor 740 may calculate a physiological parameter of interest, e.g., a blood pressure, a heart rate variation (HRV), a pulse rate, a pulse rate variation, or the like, or a combination thereof, based on the detected ECG signals and/or the pulse related signals. More detailed descriptions regarding the calculation of a physiological parameter of interest may be found in International Application No. PCT/CN2015/083334 filed Jul. 3, 2015.

The smart watch may further may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured for connecting the smart watch with any related external device, e.g., a charging device, a display device, a data exchange or storage device, or the like, or a combination thereof. For example, the data generated by the processor 740 may be transmit to other devices via the connection interface. The interface may include several ports, including, for example, 4 ports, 6 ports, or the like.

It should be noted that the description about the smart watch is merely an example, not intended to limit the scope of the present disclosure. Apparently for persons having ordinary skills in the art, numerous variations and modifications may be conducted under the teaching of the present disclosure. However, those variations and modifications may not depart the protecting scope of the present disclosure. For example, the smart watch may further include a positioning unit, an instant messaging unit, or the like, or a combination thereof. A subject wearing the smart watch may communicate with other related members at any time via the instant messaging unit. The subject may be located by others based on signals from the positioning unit. Similarly, other related members may visit or review the signals or information with an access privilege.

FIG. 9-A and FIG. 9-B illustrate a top view and a bottom view of a smart watch which is another exemplary measuring device illustrated in FIG. 7, according to some embodiments of the present disclosure. The smart watch may be a wrist watch. As illustrated in FIG. 9-A, the smart watch may include a watch header 910 (may be same with the header 810 in FIGS. 8-A through 8-D or not), together with the first electrode 710, the second electrode 720, the third electrode 730, the processor 740 and one or more watch straps.

The watch header 910 may include a watch frame 920. The watch frame 920 may include a side wall and a bottom. In some embodiments, the side wall of the watch frame 920 may be made of metal (including but not limited to, golden, silver, copper, stainless steel, iron, or the like), and the bottom of the watch frame 920 may be made of metalloids. In some embodiments, the side wall and the bottom of the watch frame 920 may both be made of metal including a same kind of metal or a different kinds of metals. In some embodiments, the side wall and the bottom of the watch frame 920 may be made of a metalloids including, for example, ceramic, plastic, or the like, or any combination thereof.

It may be seen that the first electrode 710 and the second electrode 720 are placed on the two sides of the smart watch and the third electrode 730 is placed on the back side of the watch header 910. In some embodiments, the first electrode 710 and the second electrode 720 may be placed on any location of the exterior surface of the watch frame 920. Merely by way of example, for a smart watch with an essentially square or rectangular watch header, the first electrode 710 and the second electrode 720 may be placed on the opposite sides of the watch header where the watch header 910 may connect with the watch strap as shown in FIG. 9-A. In some embodiments, the first electrode 710 and the second electrode 720 may be placed on the left side and the right side of the watch header 910. In some embodiments, the first electrode 710 and the second electrode 720 may be placed on the same side of the watch header 910. In some embodiments, the first electrode 710 and the second electrode 720 may be placed on two adjacent sides of the watch header 910. In some embodiments, the first electrode 710 and the second electrode 720 may be placed on the interior surface or exterior surface of the watch strap.

Similarly, the third electrode 730 may be placed on any side of the watch header 910 (on the back side only for illustration purposes in FIG. 9-B). Merely by way of example, the third electrode 730 may be placed on the exterior surface of the bottom of the watch frame 920, e.g., in the center of the exterior surface of the bottom, at an edge position of the exterior surface of the bottom, or the like. In another example, there may be a groove in the exterior surface of the bottom of the watch frame 920, and the third electrode 730 may be placed in the groove. The top surface of the third electrode 730, facing the wrist, may be on the same (or almost the same) plane as the opening of the groove. In some embodiments, the third electrode 730 may be placed on the interior surface or exterior surface of the watch strap.

In some embodiments, the first electrode 710, the second electrode 720, and the third electrode 730 may be made of a conductive material including, for example, a metal including stainless steel, iron, silver, copper, gold, or the like, or a combination thereof, an alloy of a metal, or the like, or a combination thereof. Besides, the first electrode 710, the second electrode 720, and the third electrode 730 may be made of a material that may be harmless to a subject when it is used as instructed or under normal conditions. In some embodiments, the first electrode 710, the second electrode 720, and the third electrode 730 may be made of a flexible material to accommodate the curvature of the wrist of a subject. Merely by way of example, the first electrode 710, the second electrode 720, and the third electrode 730 may be made of gold-plated copper or silver chloride-plated copper. In some embodiments, the materials of the first electrode 710, the second electrode 720 and the third electrode 730 may be the same as or different from each other.

In some embodiments, the thickness of the first electrode 710, the second electrode 720, and the third electrode 730 may be the same with or different from each other. In some embodiments, the thickness of the first electrode 710, the second electrode 720, and the third electrode 730 may be not smaller than 0.1 millimeter.

In some embodiments, the watch frame 920 may be made of a metal, for example, stainless steel, iron, silver, copper, gold, or the like, or a combination thereof, and there may be filled with an insulating material between the electrodes and the watch frame 920 when the first electrode 710, the second electrode 720, and the third electrode 730 may be placed on the watch frame 920. Merely for example, a first insulating gel may be filled between the first electrode 710 and the watch frame 920; a second insulating gel may be filled between the second electrode 720 and the watch frame 920. The first insulating gel may be the same as or different from the second insulating gel.

The first electrode 710, the second electrode 720, and the third electrode 730 may be connected with the processor 740 via one or more electric wires. The wires may be configured to connect electrodes to the processor 740. One end of the first electric wire may be connected to the first electrode 710, and the other end of the first electric wire may be connected to the processor 740. Similarly the second electrode 720 and the third electrode 730 may be connected with the processor 740 via a second electric wire and a third electric wire. If there are gaps between the wires and the watch frame 920, water or sweat may enter the watch header 910 along the electrodes and the watch header 910 may be damaged. In some embodiments, the gaps between the electric wires and the watch frame 920 may be filled with a waterproof material to prevent liquid from entering the watch header 910.

As shown in FIG. 9-A and FIG. 9-B, when a subject wears the smart watch on one wrist, the third electrode 730 may contact the body of the subject. The subject may place one or more fingers on both of the first electrode 720 and the second electrode 720, electrocardiographic leads or electrocardiographic circuits may be formed, and the ECG related signals acquired by the first electrode 710, the second electrode 720, and the third electrode 730 may be used to obtain an ECG diagraph. Other physiological parameters of interest, including, for example, a heart rate, a heart variation may be obtained. The smart watch may be used to generate continuous physiological data of the subject. The continuous physiological data may be used to monitor the physical condition of the subject.

In some embodiments, the smart watch may further include an optical sensor 780 (as illustrated in FIG. 7). As shown in FIG. 9-B, the optical sensor 780 may be placed on the exterior surface of the bottom of the watch frame 920. There may be a hole at the center of the third electrode 730. The optical sensor 780 may be placed in the hole. The top surface of the optical sensor 930, facing the wrist, may be on the same (or almost the same) plane with the opening of the hole. There may be an insulation space to prevent the third electrode 730 conducting electricity with the optical sensor 930. The insulation space may include a lens. The lens may be made of a light-transparent material including, for example, glass, silica gel, or the like, or a combination thereof. The optical sensor 780 may be connected with the processor 740. When a subject wears the smart watch, the optical sensor 780 may detect a pulse related signal of the subject (e.g., a PPG signal). The processor 740 may calculate a physiological parameter of interest, e.g., a pulse rate, a pulse rate variation, a blood oxygen level, or the like, or a combination thereof. Further, the processor 740 may generate an instruction to synchronize the measurement of the ECG signal and a PPG signal so that a blood pressure value may be derived from the measured signals (More detailed descriptions may be found in International Application No. PCT/CN2015/083334 filed Jul. 3, 2015). The instruction may be generated when the subject places one or more fingers on the first electrode 710 and the second electrode 720.

It should be noted that the arrangement of the optical sensor 780 is merely an example, not to be limiting. Apparently for persons having ordinary skills in the art, numerous variations and modifications may be conducted under the teaching of the present disclosure. However, those variations and modifications may not depart the protecting scope of the present disclosure. In some embodiments, the optical sensor 780 may be on the bottom of the exterior surface of the watch frame 920, but not the same place with the third electrode 730. In some embodiments, the optical sensor 780 may be on the interior surface of the watch strap.

In some embodiments, the smart watch may further include a user interface device 940. The user interface device may include a touch screen, or a screen connected or communicating with an input device through which a subject or a user other than the subject may input information. In some embodiments, the user interface device 940 may be placed on the exterior surface of the bottom of the watch frame 920. The user interface device 940 may include several ports, e.g., six ports, as shown in FIG. 9-B. The user interface device 940 may include a charging interface, a communication interface, or the like, or a combination thereof. An interface may be shown or presented on the user interface device. In some embodiments, there may be a waterproof material in the user interface device 940 to prevent liquid from entering the watch header 910. In some embodiments, the interface 940 may be used to display or present the acquired signals or information (including an ECG waveform, a PPG waveform, a blood pressure value, or blood oxygen level, or the like, or a combination thereof). The smart watch may present information in the form of, for example, an image, text, an audio message, a video, a haptic effect, or the like, or a combination thereof. In some embodiments, the smart watch may communicate with other devices or terminals via, including, Bluetooth, WiFi, infrared communication, or the like, or a combination thereof.

FIG. 10-A through FIG. 10-C show an exemplary electrode that may be used to acquire an ECG signal, according to some embodiments of the present disclosure. As illustrated in FIG. 10-C, the electrode may include a flexible conductive layer 1010, a gluing layer 1020, and a button 1030. The electrode may be flexible and adjustable, and may be placed on a body location of a subject, e.g., the wrist, the upper arm, the leg, the neck, the ankle or the like.

In some embodiments, the flexible conductive layer 1010 may include a first opening (not shown), and the gluing layer 1020 may include a second opening (not shown). The first opening may correspond to the second opening. The button 1030 may be placed in the opening thus the flexible conductive layer 1010 may be connected and fixed with the gluing layer 1020. In some embodiments, the button 1030 may be made of metal or an alloy of a metal, e.g., stainless steel, iron, silver, copper, gold, or the like, or a combination thereof. In some embodiments, the gluing layer 1020 may include one or more first portions 1021 and one or more second portions 1022. The first portion 1021 and the second portion 1022 may be stuck together to fix the electrode along a body location of the subject (e.g., the wrist). In some embodiments, a second portion 1022 may be placed between any two of the first portions 1021 (as illustrated in FIG. 10-B). In some embodiments, a first portion 1021 may be placed between any two of the second portions 1022. In some embodiments, the first portion 1021 and the second portion 1022 may be arranged in any form. In some embodiments, the length of the first portion 1021 or the second portion 1022 may be adjustable according to the body size of the subject (e.g., the size of the wrist). Merely by way of example, the length of the second portion 1022 may be set as 60 mm.

In some embodiments, the electrode may further include a middle layer (not shown) between the flexible conductive layer 1010 and the gluing layer 1020. The middle layer may be used to support the integral structure. The middle layer may provide a thickness for housing the electrode so that the flexible conductive layer 1010 and the gluing layer 1020 may be flat or smooth. In some embodiments, the middle layer may be made of, e.g., polyurethane.

In some embodiments, the electrode may further include an edge sealing 1050, a circle 1060, and a silicone tube 1070. The edge sealing 1050 may be configured for packing the edge of the electrode. The circle 1060 may be placed on one end of the gluing layer 1020 and the silicone 1070 may be placed on the other end of the gluing layer 1020. While the subject wears the electrode, one end of the gluing layer 1020 may pass through the circle 1060 and fix with the other end of the gluing layer 1020. The silicone 1070 is placed protruded from the surface of the gluing layer 1020, thus the silicone 1070 may be configured to secure the electrode not falling off. In some embodiments, the circle 1060 may be made of a conductive material including, a metal or an alloy of a metal, e.g., stainless steel, iron, silver, copper, gold, or the like, or a combination thereof. In some embodiments, the electrode may be connected with a plurality of wires used for transmitting electric signals detected by the electrode. In some embodiments, the electrode may be connected with a processor (not shown) via, for example, one or more wires. The processor may be configured for processing the detected electric signals to generate an ECG signal of the subject. The processor may be integrated in any layer of the electrode, or may be an external processor. In some embodiments, the electrode may be connected with the processor via a wireless connection, e.g., Bluetooth, WiFi, or the like.

Figure 11:
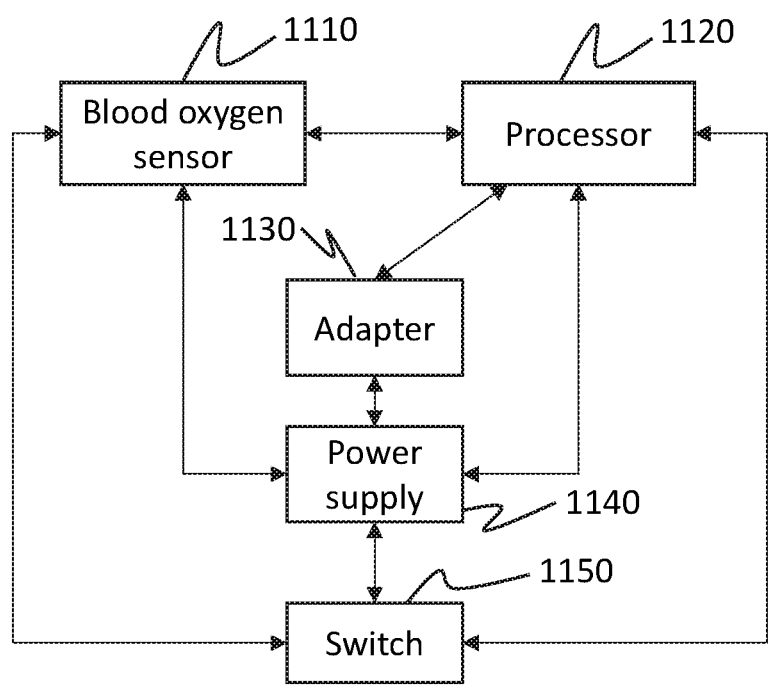
FIG. 11 shows an exemplary block diagram illustrating the architecture of a measuring device according to some embodiments of the present disclosure.

FIG. 11 is a block diagram illustrating an architecture of a measuring device according to some embodiments of the present disclosure. As illustrated in FIG. 11, the measuring device 110 (see FIG. 1) may include a blood oxygen sensor 1110, a processor 1120, an adapter 1130, a power supply 1140 and a switch 1150. The blood oxygen sensor (also referred to as a pulse oximeter) 1110 may be configured for acquiring one or more pulse related signals of the subject. The processor 1120 may be configured for controlling or coordinating an acquisition process; estimating or calculating a blood oxygen level. The adapter 1130 may be configured for enabling information transmission among the components of the device. The power supply 1140 may be configured for providing power for the device. The switch 1150 may be configured for turning the device or a component of the device on or off.

The blood oxygen sensor 1110 may be an optical sensor including one or more emitting ends used for emitting lights of suitable wavelengths and one or more receiving ends used for receiving signals resulted from the emitted lights. In some embodiments, the blood oxygen sensor 1110 may be configured to acquire one or more PPG signals. Merely by way of example, the blood oxygen sensor 1110 may acquire two PPG signals resulted from two different emitted lights (e.g., a PPG signal resulted from a red light and a PPG signal resulted from an infrared light). The two PPG signals may be used to estimate or calculate a blood oxygen level.

The processor 1120 may be connected directly or indirectly with the blood oxygen sensor 1110 via a wired or a wireless connection. In some embodiments, the processor 1120 may be configured for estimating or calculating a physiological parameter of interest, e.g., a pulse rate, a pulse rate variation, a blood oxygen level, or the like, or a combination thereof, based on the acquired signals by the blood oxygen sensor 1110. The estimation or calculation may be performed in real time or after a time delay from the acquisition of the signals. In some embodiments, the estimation or calculation may be performed by the blood oxygen sensor 1110. In some embodiments, the processor 1120 may be configured for controlling a parameter of the acquisition process of the signals, e.g., sampling frequency, sampling time interval, or the like, or a combination thereof. In some embodiments, the processor 1120 may include a memory used for storing the acquired signals and the estimated or calculated physiological parameters of interest.

The adapter 1130 may be configured for transmitting the acquired signals or the physiological parameters of interest among the components of the device, or to the health information management engine 120 or one or more terminals 130. In some embodiments, the adapter 1130 may include a WiFi adapter, a 2G wireless network adapter, a 3G wireless network adapter, a 4G wireless network adapter, or the like, or a combination thereof. In some embodiments, the transmission may be real-time, or may be performed after a delay, the delay may be in the order of seconds, or minutes, or hours, or days, or longer.

The power supply 1140 may be configured to supply power for one or more components of the device. In some embodiments, the power supply 1140 may include a battery, e.g., a lithium battery, a lead acid storage battery, a nickel-cadmium battery, a nickel metal hydride battery, or the like, or a combination thereof. In some embodiments, the power supply 1140 may include an external power source, e.g., a household power supply, an industrial power supply, or the like, or a combination thereof. In some embodiments, the power supply 1140 may include one or more charging apparatuses. The power supply 1140 may provide direct current (DC) power, or alternating current (AC) power. The power supply 1140 may further include one or more other internal components, e.g., a converter, a charge/discharge interface, or the like, or a combination thereof.

The switch 1150 may be integrated into any component of the device, or the switch 1150 may be connected with any component of the device. The switch 1150 may be used for turning a connected component on or off. In some embodiments, the switch 1150 may be a hand switch. In some embodiments, the switch 1150 may be controlled by a remote control. In some embodiments, the switch 1150 may be an automatic switch, it may turns ON and OFF automatically based on instructions provided by the processor 1120 or inputted by the subject or a user other than the subject. Exemplary instructions may include turning the device on periodically, or upon occurrence of a triggering event, or the like, or a combination thereof. In some embodiments, the switch may be a sensor control switch that may be controlled by a signal acquired by the sensor. Merely by way of example, the sensor control switch may include a sensor, such as, for example, a thermometer, a light sensor, a motion sensor, or the like, or a combination thereof. The sensor control switch may be turned on or off when a signal acquired by the sensor exceeds a threshold. As described elsewhere in the present disclosure, as used here, the term "exceed" may indicate that a signal is above a threshold or below a threshold.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the adapter 1130 may be integrated in the processor 1120. The device may include a storage used for storing signals, data, information, or the like. The processor 1120 may be local or remote. For example, the health information management engine 120, a terminal 130 (see FIG. 1-A and FIG. 1-B), or the like, or a portion thereof, may be used for achieving the functions or operations of the processor 1120.

FIG. 12-A and FIG. 12-B show an exemplary measuring device according to some embodiments of the present disclosure. As illustrated, the measuring device may be a pair of glasses 1200. The pair of glasses 1200 may be used to detect a blood oxygen level. As shown in FIG. 12-A, the pair of glasses 1200 may include a bracket 1201, two nose pads 1211, a frame 1212, together with the blood oxygen sensor 1110, the processor 1120, the adapter 1130, the power supply 1140, and the switch 1150 (see FIG. 11).

In some embodiments, the blood oxygen sensor 1110 may be fixed on a nose pad 1211 through a first opening 1202, and connected with the processor 1120. The processor 1120 may be mounted onto or fixed inside of the bracket 1201. In some embodiments, the blood oxygen sensor 1110 may be fixed on the bracket 1201 together with the processor 1120. The pair of glasses 1200 may be used to detect the subject's physiological signals and monitor physiological parameters of interest in real time and/or continuously.

Merely by way of example, while a subject wears the pair of glasses 1200, the blood oxygen sensor 1110 may detect the subject's pulse related signals (e.g., PPG signals) from the nose of the subject. There are a plurality of blood vessels, including capillaries, on the nose. The acquired signals may be transmitted to the processor 1120 and a physiological parameter of interest may be estimated or calculated, including, for example, a pulse rate, a pulse rate variation, a blood oxygen level, or the like, or a combination thereof. In some embodiments, the physiological parameters of interest may be generated directly by the blood oxygen sensor 1110. The shape of the first opening 1202 may be circular, oval, rectangular, or the like. The nose pads 1211 may be mounted or fixed on the bracket 1201.

As shown in FIG. 12-B, the pair of glasses 1200 may further include a flexible clamp 1214. In some embodiments, the flexible clamp 1214 may be device structure that may be used to touch the earlobe of a subject. Exemplary structures of this type may include, for example, an ear cuff, a headset, or the like. The flexible clamp 1214 may include a second opening 1216. The shape of second opening may be circular, oval, rectangular, or the like. In some embodiments, the blood oxygen sensor 1110 may be located on the flexible clamp 1214. One or more pulse related signals may be detected from the earlobe of the subject. There are a plurality of blood vessels, including capillaries, on an earlobe. In some embodiments, the flexible clamp 1214 may be connected with the end of the frame 1212, and thus the flexible clamp 1214 may communicate with the processor 1120 through the adapter 1130. In some embodiments, the flexible clamp 1214 may communicate with the processor 1120 via a wireless connection (e.g., WiFi, Bluetooth, infrared transmission, or the like, or a combination thereof). In some embodiments, the pair of glasses 1200 may further include a groove 1215 where the flexible clamp 1214 may be stored while not in use.

The pair of glasses 1200 may further may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured for connecting the pair of glasses 1200 with any related external device, e.g., a charging device, a display device, a data exchange or storage device, or the like, or a combination thereof.

The pair of glasses 1200 may be connected with a terminal 130, for example, a mobile phone, or the health information management engine 120, or a portion thereof, via a wired or a wireless connection. Merely by way of example, the acquired signals or calculated physiological parameters of interest may be transmitted to the mobile phone in real time, after a delay, periodically, or triggered by a triggering event described elsewhere in the present disclosure. The pair of glasses 1200 may further include additional elements or components, e.g., a positioning unit (for example, a GPS receiver, etc.) used to position the subject who wears the glasses 1200, or help the subject navigate. The location information may be transmitted to, for example, one or more terminals 130 and/or the health information management engine 120, a user other than the subject (for example, a family member, a healthcare provider, a care provider, etc.), or the like, or a combination thereof. The transmission may be performed in real time, after a delay, periodically, triggered by a triggering event (for example, the subject leaves a pre-defined area), or the like, or a combination thereof.

Figure 13:
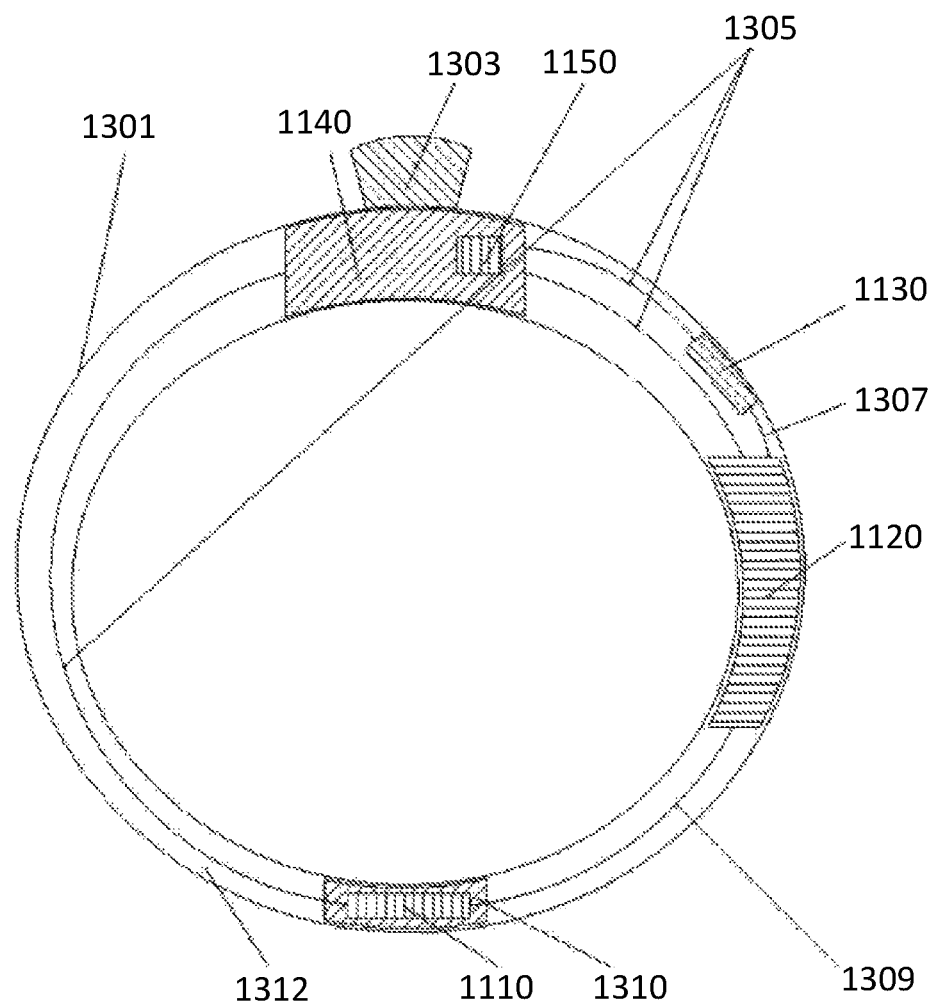
FIG. 13 shows another exemplary measuring device according to some embodiments of the present disclosure.

FIG. 13 shows another exemplary measuring device according to some embodiments of the present disclosure. As illustrated, the measuring device may be a ring 1300. The ring 1300 may include a ring body 1301, a groove 1310, a hoop 1312, together with the blood oxygen sensor 1110, the processor 1120, the adapter 1130, the power supply 1140 and the switch 1150 (see FIG. 11).

The blood oxygen sensor 1110 may be fixed on the internal surface of the ring body 1301, and the processor 1120 may be fixed inside of the ring body 1301. The blood oxygen sensor 1110 may be connected with the processor 1120 via a first electric wire 1309. The ring 1300 may be used to detect the subject's physiological signals and/or monitor physiological parameters of interest in real time and/or continuously.

Merely by way of example, while a subject wears the ring 1300, the blood oxygen sensor 1110 may detect the subject's pulse related signals (e.g., PPG signals) from a finger of the subject. There are a plurality of blood vessels, including capillaries, on a finger. The acquired signals may be transmitted to the processor 1120, and a physiological parameter of interest may be estimated or calculated, including a pulse rate, a pulse rate variation, a blood oxygen level, or the like, or a combination thereof. In some embodiments, the physiological parameters of interest may be generated directly by the blood oxygen sensor 1110.

The ring 1300 may also include a second electric wire 1305 and a third electric wire 1307. The electric wires may be used to electrically connect various components of the ring 1300. In some embodiments, the blood oxygen sensor 1110 may be fixed in the groove 1310 on the ring body 1301, and the topside of the blood oxygen sensor 1110 may be parallel with the upper opening of the groove 1310 contacting the finger or skin of the subject wearing the ring 1300, so that the blood oxygen sensor 1110 does not extrude from the ring body 1301 and the subject does not feel uncomfortable while wearing the ring 1300.

The ring 1300 may further may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured for connecting the ring 1300 with any related external device, e.g., a charging device, a display device, a data exchange or storage device, or the like, or a combination thereof.

The ring 1300 may be connected with or otherwise communicate with one or more terminals 130 and/or the health information management engine 120. The acquired signals and the calculated physiological parameters of interest may be transmitted to one or more terminals 130 and/or the health information management engine 120. The ring 1300 may further include other components, such as a positioning unit (for example, a GPS receiver, etc.) that may be used to position the subject who wears the ring 1300, or help the subject navigate. The location information may be transmitted to, for example, one or more terminals 130 and/or the health information management engine 120, a user other than the subject (for example, a family member, a healthcare provider, a care provider, etc.), or the like, or a combination thereof. The transmission may be performed in real time, after a delay, periodically, triggered by a triggering event (for example, the subject leaves a pre-defined area), or the like, or a combination thereof Merely by way of example, a related member may monitor the physiological status and location information of a subject with senile dementia.

FIG. 14-A through FIG. 14-C show a neckband that includes or is an exemplary measuring device according to some embodiments of the present disclosure. As shown in FIG. 14-A, the neckband may include a first distal part 1410, a second distal part 1420, a first middle part 1430, a second middle part 1440, and a cavity 1450.

As illustrated in FIG. 14-A, a first ECG probe 1412 may be fixed on the first distal part 1410 by a first fixture 1411, a second ECG probe 1431 may be fixed on the first middle part 1430, and a third ECG probe 1441 may be fixed on the second middle part 1440. A blood oxygen sensor 1422 may be fixed on the second distal part 1420 by a second fixture 1421. In some embodiments, as shown in FIG. 14-C, the first fixture 1411 or the second fixture 1421 may include an earphone that may be plugged into an ear of the subject. The surface of the earphone may include a conductive structure 1413 including, for example, a metal, an alloy of a metal, a conductive polymer, or the like, or a combination thereof. In some embodiments, the first fixture 1411 or the second fixture 1421 may include a flexible clamp that may be used to clamp to an earlobe of the subject. In some embodiments, the first middle part 1430 and the second middle part 1440 may include a first contacting part (not shown) (e.g., a stickup layer) and a second contacting part (not shown) respectively. The two middle parts 1430 and 1440 may be attached onto the chest of the subject by the two contacting parts (not shown). The three ECG probes may be used to detect an ECG signal of the subject, and the blood oxygen sensor 1422 may be used to detect a pulse related signal of the subject.

Merely by way of example, while a subject wears the neckband, the first ECG probe 1412 may be put in contact with an ear, the second ECG probe 1431 and the third ECG probe 1441 may be fixed on the chest, an ECG lead or an ECG circuit may be formed and an ECG signal may be acquired. The blood oxygen probe 1422 may be put in contact with an earlobe or an ear so that one or more pulse related signals may be acquired. The acquired signals may be transmitted to a processor (not shown) for estimating or calculating a physiological parameter of interest including a heart rate, a heart rate variation, a pulse rate, a pulse rate variation, a blood oxygen level, a blood pressure, or the like, or a combination thereof.

The neckband may further include a power supply (not shown) and a controller (not shown). In some embodiments, the controller may be configured to control a parameter of the acquisition process of the signals, e.g., sampling frequency, sampling time internal, or the like, or a combination thereof. In some embodiments, the controller may be configured to transmit relevant information (for example, acquired signals, calculated physiological parameters, etc.) to other terminals or the health information management engine 120, or a portion thereof including, e.g., the database 140, a mobile phone, or the like, or a combination thereof.

In some embodiments, the cavity 1450 as illustrated in FIG. 14-A and FIG. 14-B may be configured for housing the power supply (not shown), the controller (not shown), the ECG probes, the blood oxygen probe, and other components. In some embodiments, as illustrated in FIG. 14-A, the cavity 1450 may be located within the neckband 1400 and connected with various components via a wired or a wireless connection. In some embodiments, as illustrated in FIG. 4-B, the containing cavity 1450 may be located away from the neckband 1400 (e.g., may be placed in a pocket of a coat, a backpack, etc.) and communicate with the neckband via a wire 1451 or via a wireless connection. The cavity 1450 may be in one of various shapes including, e.g., rectangle, oval, irregular shape, or the like.

In some embodiments, the neckband 1400 may include, be connected to, or communicate with a user interface device (not shown). The user interface device may include a touch screen, or a screen connected or communicating with an input device through which a subject or a user other than the subject may input information. The user interface device may be implemented on an external surface of the cavity 1450. An interface may be shown or presented on the user interface device.

In some embodiments, the neckband 1400 may be connected with a mobile phone via, for example, Bluetooth, a near field communication (NFC) protocol, or the like, or a combination thereof. The acquired signals or physiological parameters of interest may be transmitted and displayed or presented on or by the mobile phone. An interface may be implemented on the mobile phone so that information exchange with the neckband 1400 may be achieved.

Information may be exchanged with the neckband 1400 via an interface. For instance, via the interface, the subject or a user other than the subject may set measuring mode or measuring parameters, setting a control mode, or the like, or a combination thereof. At least some of the signals or physiological parameters of interest acquired by the neckband 1400 may be transmitted to a terminal 130, the database 140, the health information management engine 120, or a portion thereof, via the mobile phone, a wireless adapter, or a wired connection.

FIG. 15-A and FIG. 15-B show a wristband 1500 that includes or is an exemplary measuring device according to some embodiments of the present disclosure. As illustrated, a stereogram and a sectional view are provided in FIG. 15-A and FIG. 15-B, respectively. It may be seen that the wristband 1500 may include a wristband body 1502 with a plurality of components including, for example, a first electrode 1503, a second electrode 1504, a third electrode 1501, an optical sensor 1506, and a processor 1509.

The first electrode 1503, the second electrode 1504, and the third electrode 1501 may be configured for acquiring an ECG signal of the subject. Description regarding an ECG electrode may be found elsewhere in the present disclosure (e.g., the electrode may be a flexible electrode, see FIG. 10). The first electrode 1503 and the second electrode 1504 may be fixed (e.g., by suturing) in/on the interior surface of the wristband body 1502. The third electrode 1501 may be fixed (e.g., by suturing) in/on the exterior surface of the wristband body 1502. It should be noted that there may be other ways to fix the first electrode 1503, the second electrode 1504, and the third electrode 1501 in the wristband body 1502 including, for example, using a glue, by a threaded connection, or the like, or a combination thereof.

In some embodiments, the first electrode 1503 and the second electrode 1504 may be located apart from each other and may not be electrically connected. A subject may wear the wristband 1500 on one hand, when he puts the other hand on the third electrode 1501, the first electrode 1503, the second electrode 1504, the third electrode 1501, and the subject may form a plurality of electrocardiographic leads used to detect potential differences between a pair of points on the body of the subject. An ECG signal may be acquired based on the potential differences.

The optical sensor 1506 may be configured for acquiring a pulse related signal of the subject. In some embodiments, the wristband body 1502 may include a first hole 1505. The optical sensor 1506 may be housed or secured in the first hole 1505, by way of, e.g., using a glue, using a fixture or a fastening structure, suturing, or the like, or a combination thereof. Further, the top surface of the optical sensor 1506, facing or contacting the wrist, may be on the same (or almost the same) plane with the top of the hole 1505, so that the optical sensor 1506 does not protrude beyond the interior surface of the wristband body 1502.

The processor 1509 may be configured for calculating a physiological parameter of interest based on the acquired ECG signal and the pulse related signal including, for example, a heart rate, a heart rate variation, a pulse rate, a pulse rate variation, a blood pressure, a blood oxygen level, or the like, or a combination thereof. In some embodiments, the processor 1509 may be configured for controlling a parameter of the acquisition, including, sampling frequency, sampling time interval, or the like, or a combination thereof. In some embodiments, the processor 1509 may further include a storage device (not shown) used for storing the acquired signals, and the calculated physiological parameters of interest.

In some embodiments, as illustrated in FIG. 15-B, the wristband 1500 may further include a first electric wire 1513, a second electric wire 1511, a third electric wire 1512, and a fourth electric wire 1510. One end of the electric wires 1510-1513 may be connected with the processor 1509, and the other end of the electric wires 1510-1513 may be connected with the electrodes or the optical sensor 1506, respectively. The acquired ECG signals and pulse related signals may be transmitted to the processor 1509 via the electric wires 1510-1513. For example, the first electric wire 1513 may be connected with the optical sensor 1506 and the processor 1509. It should be noted that the electric wires and the electrodes may be flexible and deformable, so that they may bend to accommodate the curvature of the wrist of a subject, and therefore the first electrode 1503, the second electrode 1504, and the third electrode 1501 may fit the wrist closely.

In some embodiments, the wristband 1500 may include a temperature sensor 1508 configured for acquiring a body temperature signal. The temperature sensor 1508 may be fixed (e.g., by suturing) in/on any location of the interior surface of the wristband body 1502. The temperature sensor 1508 may be connected with the processor 1509 via the fifth electric wire 1514 in the wristband body 1502. In some embodiments, the wristband body 1502 may include a second hole 1507. The temperature sensor 1508 may be housed or secured in the second hole 1507, by way of, e.g., using a glue, using a fixture or a fastening structure, suturing, or the like, or a combination thereof. Similarly, the top surface of the temperature sensor 1508 may be on the same (or almost the same) plane with the top of the second hole 1507, so that the temperature sensor 1507 does not protrude beyond the interior surface of the wristband body 1502.

In some embodiments, the three electrodes, the optical sensor 1506, and the temperature sensor 1508 may be arranged in any form and at various locations. For example, the optical sensor 1506 may be placed between the first electrode 1503 and the second electrode 1504. In some embodiments, the wristband 1500 may further include an adapter (not shown in FIG. 15-A or FIG. 15-B). The adapter may be fixed in the wristband body 1502, and be connected with the processor 1509. The processor 1509 may be transmitted, via the adapter, the acquired signals and the calculated physiological parameters of interest to, for example, a terminal 130, the database 140, the health information management engine 120, or a portion thereof, or the like, or a combination thereof. The adapter may be wireless or wired. The wireless adapter may include a WIFI communication adapter, a 2G wireless network adapter, a 3G wireless network adapter, a 4G wireless network adapter, or the like, or a combination thereof. In some embodiments, the terminal 130 and/or the health information management engine 120 may further process or analyze the signals or data to generate a plurality of additional information including, for example, disease information, the health condition, information relating a population including the subject, or the like, or a combination thereof.

The wristband 1500 may further may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured for connecting the wristband 1500 with any related external device, e.g., a charging device, a display device, a data exchange or storage device, or the like, or a combination thereof.

Figure 16:
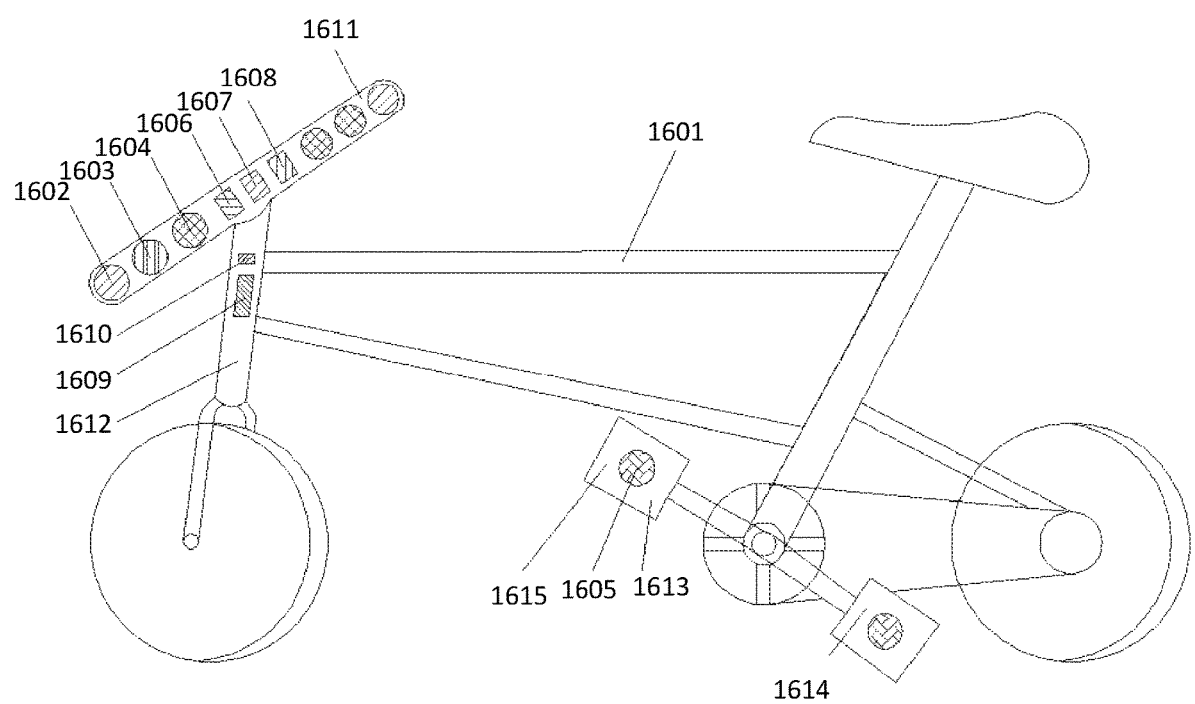
FIG. 16 shows an exemplary bicycle with an exemplary measuring device according to some embodiments of the present disclosure.

FIG. 16 is a sectional view illustrating a bicycle 1600 that includes or is an exemplary measuring device according to some embodiments of the present disclosure. The bicycle 1600 may include a bicycle body 1601, a handlebar 1611, a frame 1612, a pedal 1613, with a plurality of components including, for example, a physiological sensing module (not shown), a processor 1606, a positioning device 1607, an adapter 1608, a power supply 1609, and a switch 1610.

The physiological sensing module may include a body fat sensor 1602, a blood oxygen sensor 1603, an ECG sensor 1604, a pressure sensors 1605, or the like, or a combination thereof. In some embodiments, the bicycle 1600 may be used to monitor a subject's physiological condition including, for example, a plurality of physiological signals and/or physiological information. Merely by way of example, when a subject (e.g., a rider) is riding on the bicycle 1600, the physiological sensing module may be configured or used to detect and collect a plurality of physiological signals of the rider. The processor 1606 may be configured for analyzing the acquired signals, calculating a physiological parameter of the subject based on the signals, and/or analyzing the acquired signals or calculated physiological parameter.

As illustrated, the body fat sensor 1602, the blood oxygen sensor 1602 and the ECG sensor 1604 may be fixed on the handlebar 1611. In some embodiments, the body fat sensor 1602 may be configured for acquiring body fat information of the subject. Merely by way of example, when a rider is riding on the bicycle 1600 with his or her hand grasping the body fat sensor 1602 fixed on the handlebar 11, body fat information of the rider may be detected and a body fat related physiological parameter may be obtained by the processor 1606. In some embodiments, the blood oxygen sensor 1603 may be configured to acquire a plurality of pulse related signals (e.g., PPG signals), and a blood oxygen level of the rider may be determined by the blood oxygen sensor 1603 or by the processor 1606. In some embodiments, the ECG sensor 1604 may be configured to acquire an ECG signal. Cardiac information including, for example, heart rate, heart rate variation, or the like, may be generated based on the acquired ECG signal by the processor 1606. In some embodiments, the number of the physiological sensors may be adjustable by the subject, e.g., two, three, five, ten, or the like. For example, two body fat sensors 1602 may be placed on two sides of the handlebar 1611.

In some embodiments, the pressure sensor 1605 may be fixed on the pedal 1613. In some embodiment, the pedal 1613 may include a left pedal 1614 and a right pedal 1615, and a pressure sensor 1605 may be located on the left pedal 1614, and a pressure sensor 1605 may be located on the right pedal 1615. When the rider is riding on the bicycle 1600 putting his/her feet on the pressure sensors 1605, pressure related information may be detected. Then calories consumed by the rider may be estimated by the processor 1606 based on the pressure related information.

In some embodiments, the positioning device 1607 is fixed on the bicycle body 1601 and connected with the processor 1606. The positioning device 1607 may be configured or used to monitor the position related information of the bicycle 1600. The position related information may include location, a real time road condition, traffic control, speed, time, direction, or the like, or a combination thereof. In some embodiments, the bicycle 1600 may further include an alert unit including, for example, a display, a speaker, or a haptic generator (not shown) connected with the processor 1606. An alert may be generated and provided by the alert unit (not shown) under certain conditions. Exemplary conditions may include that the speed exceeds a threshold value, the location is beyond a predefined area, a physiological signal or parameter exceeds a threshold, or the like, or a combination thereof. The conditions may be set by the subject or a user other than the subject, or set by the system default, or may be loaded from the positioning device 1607 (e.g., the positioning device 1607 may monitor whether speed-limit information is present). In some embodiments, the pressure related information and the position related information may be taken into account and the physiological parameters of interest may be calculated with an improved accuracy.

The bicycle 1600 may further include an adapter 1608 configured for transmitting the acquired signal or information, the physiological parameter of interest, or the like, or the combination thereof to one or more terminals 130, the database 140, and/or the health information management engine 120, or the like, or a combination thereof. See relevant descriptions regarding the adapter elsewhere in the present disclosure (see, e.g., FIG. 12 and the description thereof). In some embodiments, the adapter 1608 may be fixed to the handlebar 1611 and connected with the processor 1606 to transmit information processed by the processor 1606 to one or more terminals 130, the database 140, and/or the health information management engine 120, or the like, or a combination thereof. In some embodiments, the adapter 1608 may be a wired adapter, a WiFi adapter, a 2G wireless adapter, a 3G wireless adapter or a 4G wireless adapter, or the like, or a combination thereof.

The bicycle 1600 may further include a power supply 1609 used for providing power for one or more components of the bicycle and a switch 1610 used for turning a component of the bicycle 1600 on or off. In some embodiments, the bicycle 1600 may further include a display including, for example, a touchscreen. An interface (not shown) may be shown on the display. The display may be fixed on the handlebar 1611 and may be connected with the processor 1606. The bicycle 1600 may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured to connect the bicycle 1600 with any related external device, e.g., a charging device, a display device, a data exchange or storage device, or the like, or a combination thereof.

FIG. 17-A and FIG. 17-B illustrate a steering wheel 1700 that includes or is an exemplary measuring device according to some embodiments of the present disclosure. FIG. 17-A and FIG. 17-B provide a top view and a bottom view of the steering wheel 1700, respectively. The steering wheel 1700 may include a steering body 1710, a connection rod 1720, a steering skeleton 1730, with a plurality of components located, including, a blood oxygen sensor 1750, a first electrode 1780, a second electrode 1760, a third electrode 1770 and a processor (not shown).

As illustrated in FIG. 17-A, the connection rod 1720 may include a left connection rod 1721, a right connection rod 1722, and a lower connection rod 1723. The connection between the steering body 1710, and the steering skeleton 1730 may be enhanced by the three connection rods 1721, 1722 and 1723. As shown the steering skeleton 1730 may be set in the circle center of the steering body 1710 and fixed thereto through the connection rod 1720. For example, two ends of the left connection rod 1721 may be fixed to the left side of the steering body 1710 and the left side of the steering skeleton 1730, respectively. Likewise, two ends of the right connection rod 1722 may be fixed to the right side of the steering body 1710 and the right side of the steering skeleton 1730, respectively.

As illustrated in FIG. 17-B, the blood oxygen sensor 1750, the first electrode 1780, the second electrode 1760, and the third electrode 1770 may be fixed on any locations of the steering body 1710. For example, the first electrode 1780 may be placed adjacent to the second electrode 1760, and the third electrode 1770 may be placed opposite to the first electrode 1780 and the second electrode 1760. In some embodiments, a processor may be mounted onto or inside the steering body 1710, the connection rod 1720, or the steering skeleton 1730. In some embodiments, the processor may be located in another location in the vehicle in which the steering wheel 1700 is installed. The processor may be connected with the blood oxygen sensor 1750, the first electrode 1780, the second electrode 1760, and/or the third electrode 1770.

The blood oxygen sensor 1750 may be configured for acquiring a blood oxygen related signal (e.g., a PPG signal). In some embodiments, the blood oxygen sensor 1750 may be an optical sensor. The first electrode 1780, the second electrode 1760, and the third electrode 1770 may be configured to acquire an ECG signal. The processor (not shown) may be configured to analyze or process the acquired signals, calculate or estimate a physiological parameter of interest, or the like, or a combination thereof.

Merely by way of example, when a subject (e.g., a driver) is driving with his hand(s) holding the steering wheel 1700, the blood oxygen sensor 1750 may be configured or used to detect and collect a plurality of blood oxygen related signals of the driver, based on which blood oxygen related information may be generated, including blood oxygen satura-tion, blood viscosity, or the like. As another example, the driver's two fingers of one hand are in contact with the first electrode 1780 and the second electrode 1760, one or more fingers of the other hand are in contact with the third electrode 1770. An ECG lead or an ECG circuit is formed by the first electrode 1780, the second electrode 1760, the third electrode 1770, and the body of the driver. ECG signals of the driver may be detected. The detected ECG signals may be used to analyze the driver's heart rate, heart rate variation, or the like, or a combination thereof. As a further example, the fatigue status (e.g., a fatigue level) of the driver may be estimated based on the acquired blood oxygen related signals, the ECG signals, the generated blood oxygen related information, the heart rate, the heart rate variation, blood pressure, or the like, or a combination thereof.

In some embodiments, the acquired signals may be transmitted to a terminal 130, the database 140, and/or the health information management engine 120, or a portion thereof, or the like, or a combination thereof. The blood oxygen related information or some other health related information may be generated by the terminal 130 or the health information management engine 120, or a portion thereof. The generated information may be transmitted to a terminal 130, the subject, a user other than the subject, in real time, after a delay, periodically, or triggered by a triggering event, or the like, or a combination thereof. In some embodiments, while an abnormal change is identified in the generated information, an alert may be generated and provided to the driver, and/or transmitted to one or more terminals, or a user other than the subject (see relevant descriptions regarding the alert elsewhere in the present disclosure).

The steering wheel 1700 may further include an alert unit 1740, a fingerprint sensor (not shown), and an adapter (not shown), one or more of which may be fixed on the steering body 1710, the connection rod 1720, or the steering skeleton 1730, and connected with the processor (not shown). The alert unit 1740 may be configured to generate or providing an alert while an abnormal condition is identified. Merely by way of example, when the fatigue level of the driver exceeds a preset threshold value. In some embodiments, the alert unit 1740 may provide an audio alert, a video alert, a haptic alert, etc. The alert may be provided in various ways as disclosed elsewhere in the present disclosure. The adapter (not shown) may be used to transmit the acquired signals and/or the calculated physiological parameters of interest to the health information management engine 120, the database 140, or one or more terminals 130, which may be configured to monitor the driver's physiological status real time or not. The fingerprint sensor (not shown) may be configured to recognize fingerprint-related signals which may be utilized to unlock the steering wheel 1700, or be used to keep user's privacy by locking up the acquired signals and the calculated physiological parameters of interest.

The steering wheel 1700 may further may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured for connecting the steering wheel 1700 with any related external device, e.g., a charging device, a display device, a data exchange or storage device, or the like, or a combination thereof.

The steering wheel 1700 may further include additional elements or components. For instance, the steering wheel 1700 may include a positioning unit (for example, a GPS receiver, a location sensor, etc.). The positioning unit may allow the driver to find his own position, or to navigate, or the like, or a combination thereof. The positioning unit may also allow another user to find the location of the driver, or the vehicle. The location information may be transmitted to, for example, one or more terminals 130 and/or the health information management engine 120, a user other than the subject (for example, a family member, a healthcare provider, a care provider, etc.), or the like, or a combination thereof. The transmission may be performed in real time, after a delay, periodically, triggered by a triggering event (for example, the subject leaves a pre-defined area), or the like, or a combination thereof.

FIG. 18-A and FIG. 18-B illustrate a jump rope 1800 that includes or is an exemplary measuring device according to some embodiments of the present disclosure. As illustrated, the jump rope 1800 may include a left handle 1810, a right handle 1820, and a line 1830 that interlink the two handles, with a plurality of components located, including, a sensor 1850, a central processor 1880, a battery 1860, an electric generator 1870 and an electrode 1890.

As illustrated in FIG. 18-B, the sensor 1850 configured for detecting a physiological signal of the subject may be placed on the outside surface of the left handle 1810 and the right handle 1820. The sensor 1850 may include an ECG sensor 1851 used to detect an ECG signal, a blood oxygen sensor 1852 used to acquire a blood oxygen related signal (e.g., a PPG signal), and a body fat sensor 1853 used to acquire a body fat information. The sensor 1850 may be connected with the central processor 1880 via a wired or a wireless connection (e.g., an electric wire integrated in the line 1830). The number of the sensors 1850 may be, e.g., two, three, five, or the like. For example, one blood oxygen sensor 1852 may be placed on either the left handle 1810 or the right handle 1820, and two ECG sensors 1851 may be placed on the left handle 1810 and the right handle 1820, respectively. Likewise, two body fat sensors 1853 may be placed on the left handle 1810 and the right handle 1820, respectively.

The central processor 1880 may be configured or used to store and analyze the acquired signals (including, for example, ECG signals, PPG signals, body fat information, or the like, or a combination thereof), calculating or estimating a physiological parameter of interest (including, for example, a heart rate, a heart rate variation, a pulse rate, a pulse rate variation, a blood pressure, a blood oxygen level, a body fat level, or the like, or a combination thereof), or the like, or a combination thereof. Further in some embodiments, the central processor 1880 may be connected with a terminal 130 (for example, a mobile phone, a tablet, etc.), a local server (e.g. a computer or a mobile) or a remote server (e.g., a cloud server) via a wire connection or a wireless connection, which may be configured to model and analyze the physiological parameters and/or generate a health condition related information. The information may be provided to the subject for his reference. In some embodiments, statistical data or data acquired by a data mining may be used to analyze the health condition of the subject. Further, in some embodiments, the central processor 1880 may be connected with a terminal and may send the physiological information to the terminal (e.g., a mobile phone app).

Merely by way of example, when a subject is skipping rope with his hands holding the left handle 1810 and the right handle 1820, one hand (e.g., the left hand) may contact with one ECG sensor 1851 and the body fat sensor 1853, the other hand (e.g., the right hand) may contact another ECG sensor 1851 and the blood oxygen sensor 1852. When the power is on, the sensors may detect and collect the subject's physiological signals including, ECG signals, PPG signals, body fat signals, bio-impedance signals, or the like. The detection may be performed real time, periodically, or triggered by a triggering event. A physiological parameter of interest may be calculated including, for example, heart rate, heart rate variation, pulse rate, pulse rate variation, body fat information, blood pressure, bio-impedance information, or the like, or a combination thereof. More detailed descriptions regarding the calculation of a physiological parameter of interest may be found in International Application No. PCT/CN2015/083334 filed Jul. 3, 2015.

In some embodiments, both the left handle 1810 and the right handle 1820 may include a chamber 1840. The chamber 1840 may house a battery 1860 used for providing power for the sensor 1850 and/or the central processor 1880. One or both of the left handle 1810 and the right handle 1820 may include an electric generator 1870 used for generating electricity based on, for example, the motion of the jump rope. The electric generator 1870 may be housed in the chamber 1840. In some embodiments, the electric generator 1870 may be connected with the battery 1860 that may be chargeable. The electric generator 1870 may include a rotor 1871 that may be driven by the line 1870 to guarantee a persistent power for the jump rope. Merely by way of example, when a subject (e.g., an exerciser) is skipping rope, the rotor 1871 may be driven to rotate and to generate electricity by the rotation of the line 1830. The generated electricity may be used to charge the battery 1860, or directly power the sensor 1850 and/or the central processor 1880.

In some embodiments, as illustrated in FIG. 18-B, both the left handle 1810 and the right handle 1820 may include an electrode 1890 thereon to measure the bio-impedance of the subject, based on which the body composition parameters including, body fat ratio, body water ratio, body muscle ratio, bone mass, or the like, may be acquired. For example, while the subject's hands are contact with the electrode, a safe voltage (for example, a voltage no larger than 36 V) may be provided by the battery 1860, while the bio-impedance may be measured by detecting a safe current. In some embodiments, the jump rope 1800 may further include a counter (not shown) placed on a connection part of the line 1830 with the left handle 1810 or the right handle 1820, configured to count or estimate, for example, the rotation number, the consumed calories, or the like, or a combination thereof.

The jump rope 1800 may further may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured for connecting the jump rope 1800 with any related external device, e.g., a charging device, a display device, a data exchange or storage device, or the like, or a combination thereof.

FIG. 19-A and FIG. 19-B shown an exemplary device 1900 including a mouse 1901 and a mouse pad 1902 that includes or is an exemplary measuring device according to some embodiments of the present disclosure. As illustrated, the device may include a mouse 1901 and a mouse pad 1902. The mouse 1901 may be wired or wireless. As shown in FIG. 19-B, the mouse 1901 may include a mouse body 1910, a left button 1912, a right button 1908, and a middle button 1906. In some embodiments, the middle button 1906 may be a mouse wheel. As illustrated in FIG. 19-A, the mouse pad 1902 may include a detecting area 1903 and a conductive portion 1905.

The device 1900 may include a first electrode 1913 placed on the left button 1912, a second electrode 1907 placed on the right button 1908, a third electrode 1904 placed on any location (e.g., the detecting area 1903) on the mouse pad 1902, an optical sensor 1914 placed on any location of the device 1900 (e.g., a left side of the smart mouse 1901), and a processor 1909 placed inside the smart mouse 1901. The electrodes and the optical sensor 1914 may be connected with the processor 1909 via a wired connection or a wireless connection. The first electrode 1913, the second electrode 1907, and the third electrode 1904 may be configured for acquiring an ECG signal. The optical sensor 1914 may be configured to acquire a pulse related signal (e.g., a PPG signal). The processor 1909 may be configured to analyze the acquired signals (including, for example, an ECG signal, a PPG signal, body fat information, or the like, or a combination thereof), calculate or estimate a physiological parameter of interest (including, for example, a heart rate, a heart rate variation, a pulse rate, a pulse rate variation, a blood pressure, a blood oxygen level, a body fat level, or the like, or a combination thereof), or the like, or a combination thereof. More detailed descriptions regarding the calculation of a physiological parameter of interest may be found in International Application No. PCT/CN2015/083334 filed Jul. 3, 2015.

As illustrated in FIG. 19-A, the third electrode 1904 may be placed on the detecting area 1903 on the mouse pad 1902. In some embodiments, corresponding to the detecting area 1903, the mouse body 1910 may include a contact portion 1916 (illustrated in FIG. 19-B). The third electrode 1904 may connect or communicate with the contact portion 1916 via the conductive portion 1905. The conductive portion 1905 may be placed inside of the mouse pad 1902. For example, the conductive portion 1905 may include a plurality of electric wires. The wires may be laid flat within the mouse pad 1902. The wired may be placed in parallel with each other. In some embodiments, the conductive portion 1905 may include a first inserting part (not shown) and a second inserting part (not shown) at two ends of the portion. The third electrode 1904 may include a first magnetic portion (not shown). The first inserting part (not shown) may include a second magnetic portion (not shown). The third electrode 1904 may be connected with the first inserting part (not shown) via the first magnetic portion (not shown) and the second magnetic portion (not shown). Similarly, the contact portion 1916 may include a third magnetic portion (not shown) and the second inserting part (not shown) may include a fourth magnetic portion (not shown). The contact portion 1916 may be connected with the second inserting part (not shown) via the third magnetic portion (not shown) and the fourth magnetic portion (not shown). In some embodiments, the third electrode 1904 may include a first magnetic portion (not shown). In some embodiments, the mouse pad 1902 may be conductive, for example, the mouse pad 1902 may be made of a conductive fabric. Thus the mouse pad 1902 may be used to connecting the third electrode 1904 and the contact portion 1916.

Merely by way of example, when a subject uses the mouse, one hand of the subject contacts the first electrode 1912 and the second electrode 1907, the other hand may contact the third electrode 1904. The three electrodes and the subject's body may form ECG leads or an ECG circuit used to acquire ECG signals. The processor 1909 may process the ECG signals to calculate or estimate a physiological parameter of interest including, for example, a heart rate, a heart rate variation, or the like, or a combination thereof. While the thumb of the subject may contact with the optical sensor 1914 and pulse related signals (e.g., PPG signals) may be acquired. The processor 1909 may process and analyze the acquired signals to calculate or estimate a physiological parameter of interest including, for example, a pulse rate, a pulse rate variation, a blood oxygen saturation, or a blood pressure, or the like, or a combination thereof. More detailed descriptions regarding the calculation of a physiological parameter of interest may be found in International Application No. PCT/CN2015/083334 filed Jul. 3, 2015. While the subject or the user uses the mouse continuously, signals may be detected in real time, continuously, periodically, or triggered by a triggering event. The health condition of the subject may be monitored in real time and/or continuously, or periodically.

It should be noted that when the mouse 1901 moves on the mouse pad 1902, the mouse 1901 should not enter the detecting area 1903. The size of the mouse pad 1902 and the location of the detecting area 1903 (or the location of the third electrode 1903) may be chosen accordingly. In some embodiment, the shape of the mouse pad 1902 may be rectangle, square, trapezoid, circular, ellipse, irregular shape, or the like, or a combination thereof. For example, the shape of the mouse pad 1902 may be rectangle. The length of a long side of the rectangle may be an arbitrary value, e.g., any value within an interval expressed as (m, n). The value of m and n may be adjusted based on factors including, for example, the size of the hand of the subject, the size of the mouse 1901, or the like, or a combination thereof. Merely by way of example, the length of a long side of the rectangular mouth pad 1902 may be approximately 18 cm. Similarly, the length of a short side of the mouse pad 1902 may be an arbitrary value, e.g., any value within an interval expressed as (t, s). The ratio of the length of the long side and that of the short side may be an arbitrary value, e.g., 100%, 110%, 120%, 130%, 140%, 150%, 160%, 170%, 180%, 190%, 200%, 210%, 220%, 230%, 240%, 250%, 260%, or the like. In some embodiments, the ratio may not be less than 200%. In some embodiments, the location of the third electrode 1904 may be at an arbitrary position of the mouse pad 1902. For a rectangular mouse pad 1902, the third electrode 1904 may be along a left short side, along a right short side, along a top long side, along a lower long side, in the lower-left corner, in the lower-right corner, in the top-left corner, in the top-right corner, or any other location of the mouse pad 1902. Merely by way of example, if a subject prefers to hold the mouse 1901 by his right hand, the third electrode 1904 may be placed in the lower-left corner of the mouse pad 1902. If a subject prefers to hold the mouse 1901 by his left hand, the third electrode 1904 may be placed in the lower-right corner of the mouse pad 1902.

In some embodiments, the device may further include a user interface device (not shown in FIG. 19-A or FIG. 19-B). The user interface device may include a touch screen, or a screen connected or communicating with an input device through which a subject or a user other than the subject may input information. In some embodiments, the mouse 1901 and/or the mouse pad 1902 may constituent the input device. An interface may be shown or presented on the user interface device. The user interface device may be placed on the right side, the left side, or the upper surface of the mouse body 1910, or may be located on the mouse pad 1902. The user interface device may be connected or communicate with the processor 1909. A subject or a user may set some parameters and/or a measuring way via the user interface device. In some embodiments, a control method may be set or provided via the user interface device. In some embodiments, the mouse 1901 may be controlled to connect with a mobile phone via Bluetooth.

In some embodiments, the device may connect or communicate with a terminal (e.g., a mobile phone or a computer). The connection may be wired or wireless. The wireless connection may include Bluetooth communication, infrared communication, or the like, or a combination thereof. In some embodiments, the acquired signals and the calculated physiological parameters of interest may be transmitted to a remote server or a cloud server to be managed conveniently. If some parameters exceed a threshold set by the subject or a user other than the subject, or some parameters exceed a normal range, an alert, a recommendation, a reminder, or the like, or a combination thereof, may be generated. For example, if the blood pressure generated exceeds a value, the terminal may provide an alert, or a reminder that the subject may need to take some blood pressure medication.

This description is intended to be illustrative, and not to limit the scope of the present disclosure. Many alternatives, modifications, and variations will be apparent to those skilled in the art. The features, methods, and other characteristics of the exemplary embodiments described herein may be combined in various ways to obtain additional and/or alternative exemplary embodiments. For example, the device 1900 may share a common processor with a computer connected with the mouse. As another example, the acquired signals and/or calculated physiological parameters of interest may be transmitted and stored in the computer.

FIG. 20-A through FIG. 20-C show a tablet 2000 that includes or is an exemplary measuring device according to some embodiments of the present disclosure. FIG. 20-A and FIG. 20-B provide a top view and a bottom view of the tablet 2000, respectively. As illustrated in FIG. 20-A, the tablet 2000 may include a display panel 2001 and a shell 2002. The top surface of the shell 2002 may include an opening 2003 to hold the display panel 2001. As illustrated in FIG. 20-B, the tablet 2000 may include a first electrode 2004, a second electrode 2005, a third electrode 2006, and an optical sensor 2007. The three electrodes may be configured to acquire an ECG signal of a subject. The optical sensor 2007 may be configured to acquire a pulse related signal (e.g., a PPG signal). The tablet 2000 may also include a processor 2010 placed inside of the shell 2002.

The three electrodes may be located on any locations of the top surface or the bottom surface of the shell 2002. As used herein, the top surface of the shell 2002 may include a display; the bottom surface of the shell 2002 may refer to the opposite surface relative to the top surface of the shell 2002. In some embodiments, the three electrodes may be located in a line arrangement as illustrated in FIG. 20-B. The line arrangement may be in any arbitrary position of the bottom surface of the shell 2002. Merely by way of example, the line arrangement may be parallel to a long side of the shell 2002, a short side of the shell 2002, or a diagonal of the shell 2002. In some embodiments, the three electrodes may be located as a triangle arrangement. For example, one or two sides of the triangle may be parallel to a side of the shell 2002. In some embodiments, the three electrodes may be located in any arrangement of various irregular shapes. For example, the first electrode 2004 and the second electrode 2005 may be placed parallel to a long side or a short side of the shell 2002, and the third electrode 2006 may be placed near to the other short side of the shell 2002. The distance between the electrodes and the edge of the shell 2002 may be arbitrary, e.g., 1 cm, 2 cm, 5 cm, 10 cm, 15 cm, or the like. The optical sensor 2007 may be in an arbitrary location of the shell 2002 including, for example, the top surface of the shell 2002 or the bottom surface of the shell 2002. Merely by way of example, the optical sensor 2007 may be located near a corner of the shell 2002.

In some embodiments, the first electrode 2004, the second electrode 2005, and the third electrode 2006 may be a two-layer structure. The first tier may include a conductive material including, for example, a metal, an alloy of a metal, a conductive polymer, or the like, or a combination thereof. The second tier lying on the first tier may include a material having a desirable characteristic including, for example, conductivity, resistance to corrosion, or the like, or a combination thereof. The second layer may be harmless to a subject. Merely by way of example, the first layer may be copper, and the second layer may be gold plated beryllium copper or silver chloride-plated.

In some embodiments, as illustrated in FIG. 20-B, the tablet 2000 may further include a fingerprint sensor 2008 configured to acquire the fingerprint of a subject. In some embodiments, the fingerprint acquired may be used to unlock the tablet 2000 or to encrypt and/or decrypt information of the subject. The information may be stored in modules or units of the tablet capable of storing, a cloud account, or the like, or a combination thereof. In some embodiments, the tablet 2000 may acquire different subjects' fingerprints and each fingerprint may be associated with a specific subject. The fingerprint sensor 2008 may be in an arbitrary location of the shell 2002, including the top surface of the shell 2002 or the bottom surface of the shell 2002. For example, the fingerprint sensor 2008 may be located near a corner of the shell 2002.

In some embodiments, the tablet 2000 may further include an adapter 2009 connected with the processor 2010. The adapter 2009 may be configured to transmit the acquired signals and the calculated physiological parameters of interest to the terminal 130, the health information management engine 120, the database 140, or a portion thereof, or the like, or a combination thereof. The adapter 2009 may include a WiFi adapter, a 2G electrode wireless network adapter, a 3G electrode wireless network adapter, a 4G electrode wireless network adapter, or the like, or a combination thereof.

In some embodiments, the electrodes and sensors (including the first electrode 2004, the second electrode 2005, the third electrode 2006, the optical sensor 2007, and the fingerprint sensor 2008) may be placed in a groove (not shown) located on the shell 2002, or may be fixed on the surface of the shell 2002 using a glue or by a fixture or a fastening structure, or the like, or a combination thereof. In some embodiments, they may be screwed onto the shell 2002.

Referring back to FIG. 20-B, during a duration that a subject uses the tablet 2000, when a subject holds the tablet 2000 with two hands, fingers of one hand may contact the first electrode 2004, the second electrode 2005 and the optical sensor 2007, fingers of the other hand may contact the third electrode 2006, an ECG signal and a consecutive pulse wave signal may be detected. The detection may be continuous, or periodic, or triggered by a triggering event. Physiological parameters of interest may be generated, including, for example, a heart rate, a heart rate variation, a pulse rate, a pulse rate variation, a blood oxygen saturation, and a blood pressure, or the like, or a combination thereof. Further, the health condition of the subject including, e.g., the level of fatigue, the psychological pressure, the stress tolerance of the subject, or the like may be analyzed. The acquired signals, the calculated physiological parameters of interest, and/or the generated health condition may be transmitted to the health information management engine 120, a terminal 130, etc., to be further processed and analyzed, or may be stored or displayed or presented by the tablet 2000. The subject or a user who has an access privilege may visit tablet 2000 and review the physiological information at any time.

The tablet 2000 may further may include a connection interface or port including a Universal Serial Bus (USB) port, a Video Graphics Array (VGA) port, a High Definition Multimedia Interface (HDMI) port, a headphone port, or the like, or a combination thereof. The connection interface may be configured for connecting the tablet 2000 with any related external device, e.g., a charging device, a display device, a data exchange or storage device, or the like, or a combination thereof.

FIG. 21-A and FIG. 21-B show flowcharts of an exemplary process for a health monitoring, according to some embodiments of the present disclosure. Beginning in step 2101, information relating to a subject may be acquired. The acquisition may be performed by the measuring device 110. The acquired information may be stored in the measuring device 110, or may be transmitted to a terminal 130-1, the health information management engine 120, or the database 140. The acquired information may include physiological signals of the subject, environmental information relating to the ambient surrounding the subject, and information provided by the subject or a user other than the subject. For example, the acquired information may include a PPG signal, an ECG signal, a body temperature signal, the height, weight, age, gender, arm length, illness history, room temperature, humidity, air pressure, air flow rate, ambient light intensity, or the like, or a combination thereof.

In step 2103, a data generation may be performed. During the data generation process, at least one feature of the acquired information may be identified. For example, the acquired information may include a plurality of physiological signals (e.g., a PPG signal and an ECG signal); the features of these signals including, for example, waveform, characteristic points, peak points, valley points, amplitude, time intervals, phase, frequencies, cycles, or the like, or a combination thereof may be identified; a plurality of physiological parameters of interest including a blood pressure, a blood oxygen level, or the like, may be calculated or estimated based on the identified features. During the data generation, analysis operations including pretreatment, recognition, calculation, and calibration may be performed (see FIG. 4-C and FIG. 5-C. For example, the pretreatment may be performed in order to reduce or remove noise or interferences in the signals originally acquired. The data generation may be performed by the data generation unit 403, the data management unit 502, or the data analysis unit 503. The data generation may be performed automatically or according to some requests from the health information management engine 120, or other terminals (e.g., 130-2, . . . , 130-N). For example, another remote terminal (e.g., the terminal 130-2) may request the terminal 130-1 or the health information management engine 120 for a blood pressure value, the data generation may be performed to generate a blood pressure value in response to the request from the remote terminal. In some embodiments, the data generation process may further include a data packaging step including, for example, data compression, data encoding, data encryption, or the like. It should be noted that after the data generation in step 2103, a new acquisition process may be performed in step 2101. After the data generation process, it may follow at least some steps starting from node A 2122 as illustrated in FIG. 21-B In step 2104, a connection check may be carried out. The connection check may be performed to check whether the connection for data transmission is proper. The connection check may be carried out by the interaction unit 401, or the communication unit 506. If the connection is bad or non-existent, the process may proceed to step 2105, in which the generated data may be stored for further use. If the connection is proper or becomes proper, the data may be retrieved and the process may proceed to 2106. If the connection is already proper, the process may proceed directly to step 2106. In step 2106, the generated data may be transmitted to a server or processor (e.g., the health information management engine 120), the database 140, or a terminal 130. The server or processor may be a local server or a remote server. The server or processor may be integrated in the terminal 130-1. The transmission may be performed by the interaction unit 401, the communication unit 406, or the communication unit 506. In some embodiments, an identity verification may be performed before the data transmitting; if the identity verification is satisfactory, the data transmitting may be executed. For example, the system, or a portion thereof (for example, the health information management engine 120, the database 140, etc.), may verify whether the terminal 130-1 has a data transmission permission before transmitting data to the terminal 130-1. As another example, while a user account is logged in the terminal 130-1, a data transmission from the system, or a portion thereof (for example, the health information management engine 120, the database 140, etc.), is allowed.

In step 2107, a criterion may be set. The criterion may include a rule regarding data combination, data classification, or the like, and/or a standard regarding data array, data format, data structure, or the like. The criterion may further include a standard regarding data storage, data processing, data analysis, or the like, or a combination thereof. The criterion may be set according to a default setting of the system (e.g., an industrial standard, etc.), or may be customized by the subject (e.g., classified by time, combined by physiological parameter category, screened by data type, or the like). The criterion may be set by an institution or user that has the authority to manage the date relating to the subject. Exemplary institutions or users may include a hospital, a research institute, a healthcare provider, a care provider, etc.

Merely by way of example, the received data may include a plurality of physiological information of various types, such as information including age, gender, or the like, initial signals including an ECG signal, a PPG signal, or the like, calculated or estimated physiological parameters including a blood pressure, a blood oxygen level, or the like. The criterion may be set as a rule regarding data classification expressed as classifying the received data by data type including basic information, initial signal and calculated parameter. As another example, the received data may include data of various formats including numerical value, text format, image format, or the like. The criterion may be set as a standard regarding the data format, for example, only the data of a specific format may be used for further analysis (e.g., in step 2112). In some embodiments, different criterions may be set by different subjects. For example, data regarding body height of a subject may be expressed as a value in millimeter, while data regarding body height of another subject may be expressed as a value in meter.

In step 2108, whether the criterion is satisfied may be checked. If the answer is "No," the data may be processed (such as data format conversion, data integration, data cleaning, or the like) in step 2109 to meets the requirements of the criterion. The processing may be performed by the data management unit 502. If the answer is "Yes," the process may proceed to step 2110 to store the data. The data may be stored in any storage device disclosed anywhere in the present disclosure. In some embodiments, the storing is not necessary, the data that meets the requirements pf the criterion may be transmitted directly for further use.

In step 2111, whether to use analysis model(s) available may be determined. As used herein, an analysis model may refer to a function expressed as equation 1.

$$\begin{bmatrix} HS \\ PD \\ RD \end{bmatrix} = a \begin{Bmatrix} (pp_1, pp_2, pp_3, \ldots, pp_n) \\ (bi_1, bi_2, bi_3, \ldots, bi_n) \\ (hi_1, hi_2, hi_3, \ldots, hi_n) \end{Bmatrix} + b^* f(ep_1, ep_2, \ldots, ep_n) + \\ c * f(hd_1, hd_2, \ldots, hd_n) + d * f(si_1, si_2, si_3, \ldots, si_n). \quad (1)$$

The dependent variable expressed as $$\begin{bmatrix} HS \\ PD \\ RD \end{bmatrix}$$

of Equation 1 may refer to an analysis result, and the independent variable may refer to a plurality of data. As used herein, HS may refer to a health status or condition (e.g., health, sub-health, therapeutic effect, rehabilitation effect, or the like, or a combination thereof); PD may refer to a prediction (e.g., risk of disease); RD may refer to a recommendation (e.g., recommendation for health maintenance, health tips, disease therapy, disease precaution, medical guide, or the like). As used herein, $pp_x$ (x=1, 2, ..., n) may refer to a physiological parameter (e.g., blood pressure, blood oxygen saturation, or the like, or a combination thereof); $bi_x$ (x=1, 2, ..., n) may refer to information regarding a subject (e.g., age, body weight, or the like, or a combination thereof); $hi_x$ (x=1, 2, ..., n) may refer to a health related information (e.g., food allergy, drug allergy, smoking or not, dietary habit, or the like, or a combination thereof); $ep_x$ (x=1, 2, ..., n) may refer to an environmental parameter (e.g., temperature, humidity, or the like); $hd_x$ (x=1, 2, ..., n) may refer to a history data regarding $pp_x$, $bi_x$, $hi_x$, and $ep_x$; $si_x$ (x=1, 2, ..., n) may refer to statistical information (e.g., incidence of a disease at different ages and regions, or the like, or a combination thereof). As used herein, a, b, c, d may refer to coefficients for different parts; $f$ may refer to a function (e.g., exponential function, trigonometric function, logarithmic function, or the like, or a combination thereof).

In some embodiments, a favorite model may be selected form a group of available models. As used herein, a favorite model may refer to a model that may provide a more accurate analysis result regarding the physiological information of the subject. In some embodiments, the determination may be made by the system default, or based on instructions by the subject or a user other than the subject. In step 2112, the data may be analyzed based on a favorite model. The data analysis process may be performed by the data analysis unit 503. Operations of the data analysis may include calculating a parameter based on the received data, extracting a feature of the data, refining useful information from a batch of data, generating a relationship among the received data, or the like, or a combination thereof. Exemplary analysis methods may include statistical analysis methods (e.g., regression analysis, factor analysis, clustering, recognition analysis, or the like) and intelligent analysis methods (e.g., neural network, genetic algorithms, rough sets, or the like). The data analysis may be performed at an individual level, a group level, or both. At individual level, the $pp_x$, $bi_x$, $hi_x$, $hd_x$, $ep_x$ in Equation 1 may refer to parameters regarding a specific subject, and HS, PD, RD in Equation 1 may refer to analysis results regarding the specific subject. At group level, the $pp_x$, $bi_x$, $hi_x$, $hd_x$, $ep_x$ may refer to parameters regarding a plurality of subjects, and HS, PD, RD may refer to analysis results regarding the plurality of subjects. The analysis results at individual level and/or group level may be used to guide modification of $si_x$ in equation 1. In some embodiments, during an individual level analysis, some group level related information may be used. An analysis result may be generated in step 2112.

If there is no model(s) available to be used, the process may proceed to step 2113 to perform a data mining process and to import data from a data source. The data source may be the database 140, or may be an external data source (e.g., a remote server). The data mining process may be performed by the data mining unit 504. The data mining may be performed to construct a new analysis model, or to determine a factor of a model to be factored. In some embodiments, the constructed new analysis model may be expressed as a model of the same type with an available model (as expressed in Equation 1) or a model of a different type such as a probabilistic model that may be express as Equation 2 below.

$$PR = f\begin{bmatrix} G \\ R \\ H \end{bmatrix} + f(a). \quad (2)$$

As used herein, coefficient G represents a group, such as a group with same age, a group with similar height, a group with similar weight, or the like. Coefficient R represents a region with a specific climate, e.g., a cold region, a hot region, a temperate region, or the like. Coefficient H represents a family hereditary condition. The function $f(a)$ represents a function regarding an abnormality of a physiological parameter of interest. The probabilistic model may be applied for predicting a probability of a specific disease, a trend of a family genetic disease, or the like.

In some embodiments, as illustrated in Equation 1, the factors a, b, c, and d may be determined based on the data acquired by the data mining process. The factors a, b, c, and d may be determined through a calibration, e.g., a regression. In some embodiments, the statistical information may be obtained by the data mining process. In some embodiments, an existent model may be retrieved by the data mining process. The new constructed, factored or retrieved model may be updated in step 2115. The newly updated models may be further used to analyze the data in step 2112.

In some embodiments, the data mining may be performed according to system default. For example, the data mining may be performed in a predetermined time interval (e.g., 30 minutes, 1 hours, 5 hours, 10 hours, 12 hours, 24 hours, or the like). As another example, the data mining may be performed at a particular time point of a day (e.g., 6:00, 12:00, 21:00, 0:00, or the like). As a further example, the data mining may be performed automatically while the system is in an idle state or during an off-peak period.

In step 2116, the analysis results may be delivered back from the server or processor (see step 2106). The delivery process may be performed by the interaction unit 410, the communication unit 406, or the communication unit 506. Merely by way of example, in step 2106, the generated data may be transmitted from the terminal 130-1 to the health information management engine 120, and in step 2116, the analysis results may be delivered from the health information management engine 120 back to the terminal 130-1. In some embodiments, a connection check may be performed before the analysis results delivery. After the data is delivered back, it may follow at least some steps starting from node A 903 as illustrated in FIG. 21-B.

FIG. 21-B illustrates the process starting from node A 2122 regarding a data transmitting process among one or more terminals 130 according to some embodiments of the present disclosure. In step 2117, whether the analysis results contain abnormal information may be checked. As used herein, abnormal information may refer to that at least some of the received data or the physiological parameters of interest exceed a threshold. As used herein, "exceed" may be larger than or lower than a threshold. For example, the received blood pressure value exceeds a threshold (e.g., the value of SBP is higher than 140 mmHg, the value of DBP is lower than 60 mmHg). If abnormal information is identified, a recommendation including a health tip, a medical guide, or the like, or a combination thereof, may be generated in 2121, and the process may proceed to step 2118 to determine whether other terminals 130 have an access privilege to receive the abnormal information and/or the recommendation. If no abnormal information is identified in the analysis results, whether an access request occurs from other terminals (e.g., the terminal 130-2, . . . , 130-N) may be checked in step 2119. If the answer is "No," the whole process may end and a new process may start. If the answer is "Yes," whether other terminals 130 have an access privilege may be determined in step 2118.

In step 2118, an identity verification may be performed. Merely by way of example, the identity may be a user ID of a terminal (e.g., 130-2, . . . , 130-N) that may be obtained when a user account is registered, and may be further recognized when the user account logs in. The user ID may be in form of text or two-dimensional code. A relationship between different user IDs may be constructed by manually inputted or scanning a two-dimensional code. Merely by way of example, suppose the terminal 130-1 has a user ID X, and the terminal 130-2 has a user ID Y, the terminal 130-1 may add the user ID Y to be labeled as a family member, a friend, or a doctor, or may scan the two-dimensional code of the user ID Y, then a specific relationship may be constructed between the terminal 130-1 and the terminal 130-2. Thus in this embodiment, the identity verification may be performed by checking the user IDs to determine whether there is a specific relationship between the receiver (e.g., the terminal 130-2) and the transmitter (e.g., the terminal 130-1). If the receiving terminal satisfies the verification, the data may be transmitted. Otherwise, the transmission may be refused, or a request may be provided to the receiving terminal to obtain a verified identity through registering or logging in an effective identity.

As another example, a specific terminal may correspond to a specific member. In some embodiments, if the specific member has a relationship (for example, being a family member, a healthcare provider, a care provider, etc.) with the subject (corresponding to the terminal 130-1), it means that the specific terminal satisfies the identity verification. In some embodiments, an identification information of a specific terminal (e.g., the terminal 130-2, 130-3, . . . , 130-N) may be verified. As used herein, the identification information may refer to an identification code of the terminal. If the verification is satisfied, the specific terminal with a specific identification code may visit the system or a portion thereof with a specific access privilege. In some embodiments, the verification process may be performed at any time point of the whole process.

In step 2120, the analysis results and/or the recommendation may be pushed to other terminals corresponding to related members that have satisfied the identity verification. This procedure may be carried out by the interaction unit 401, the communication unit 406, or the communication unit 506.

This description of the exemplary process is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, while an abnormal condition is identified, an alert may be generated based on the analysis result and the alert may be transmitted to a related member. As another example, the step 2104 and the step 2106 are not necessary, while the data generation process and the data analysis process may be performed in an independent module or unit (e.g., a terminal 130-1, the health information management engine 120, or the like). Obviously in this embodiment, the step 2116 is not necessary.

Figure 22:
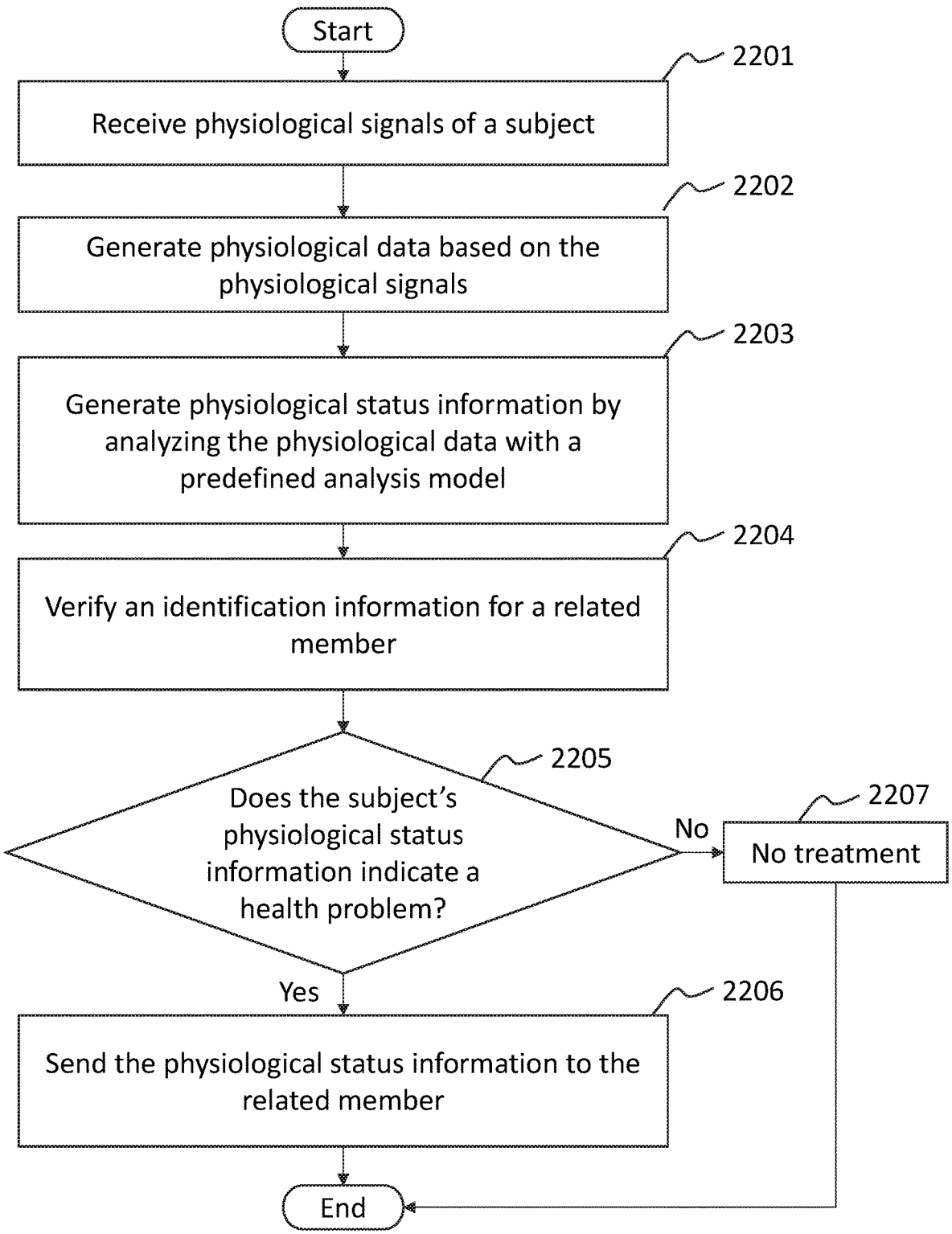
FIG. 22 provides an exemplary process for a mobile health monitoring according to some embodiments of the present disclosure.

FIG. 22 provides an exemplary process regarding a mobile health monitoring according to some embodiments of the present disclosure. Beginning in step 2201, a terminal (e.g., the terminal 130-1) or a server (e.g., the health information management engine 120) may receive physiological signals of a subject. The physiological signals may be received from one or more measuring devices 110 that may include a plurality of physiological sensors (e.g., ECG electrode, blood pressure sensor, blood oxygen saturation sensor, temperature sensor, or the like, see FIG. 3). The receiving may be performed by the interaction unit 401, the communication unit 406, or the communication unit 506. The physiological signals received from the measuring devices 110 may include, without limitations to, ECG signals, PPG signals, temperature signals, or the like.

In step 2202, physiological data may be generated based on the physiological signals. The data generation may be performed by the data generation unit 403, the data management unit 502, or the data analysis unit 503. The generated data may include, for example, a heart rate value calculated from ECG signals, a pulse rate value and a blood oxygen saturation value calculated from PPG signals, a body temperature value calculated from temperature signals, and a blood pressure value calculated from ECG signals and PPG signals (More detailed descriptions regarding the calculation a blood pressure) may be found in International Application No. PCT/CN2015/083334 filed Jul. 3, 2015). If in step 2201 the physiological signals of the subject are received by a terminal 130-1, the generated physiological data may be transmitted to a data processing server or processor (e.g., the health information management engine 120). The data processing server or processor may be a local server or a remote server. In some embodiments, the data processing server or processor may be integrated in the terminal 130-1. The data transmission may be performed by the interaction unit 401 or the communication unit 406. Before transmitting the physiological data, a check step to determine whether the connection is proper may be performed by the interaction unit 401 or the communication unit 506. If the connection is proper, the physiological data may be transmitted to the server (e.g., the health information management engine 120) successively. Otherwise, the physiological data may be stored for further use, and while the connection becomes proper, the physiological data may be extracted and transmitted to the data processing server.

In step 2203, physiological status information may be generated by the data processing server or processor and may be sent back to the terminal 130-1. The physiological status information may include, for example, health related information including health condition of the subject, therapeutic effect, rehabilitation effect, prediction of potential risks of sub-health, disease information, obesity or not, or the like; a recommendation regarding health maintenance, disease therapy, disease precaution, or the like. The physiological status information may be obtained by the data processing server (e.g., the health information management engine 120) through analyzing and processing the physiological data generated in step 2202 using some predefined analysis models.

In step 2204, an identification information of a related member may be verified. The verification process may be performed by the identity verification unit 402 or the communication unit 506. The identification information may indicate a specific relationship between the related member and the subject. In some embodiments, if the relationship may be a family relationship, a relative relationship, or a doctor-patient relationship, it means that the related member passes the verification. In some embodiments, the verification process may be performed while a request is received from the related member. In some embodiments, the verification process may be performed at any time point of the whole process. In some embodiments, an identification information of a specific terminal (e.g., the terminal 130-2, 130-3, . . . , 130-N) may be verified. As used herein, the identification information may refer to an identification code of the terminal, a logged in user account in the terminal, or the like. If the verification is passed, the specific terminal may access information relating to the subject in the system, or a portion thereof, according to a specific access privilege.

In step 2205, the system may proceed to check whether the physiological status information indicates a health problem. As used herein, a health problem may refer to an abnormal status (e.g., a sub-health condition, a potential health risk, a disease information (e.g., arrhythmia, cardiopathy, hypertension, hypotension, hyperpyrexia, hypothermia, genetic disease, or the like), or the like). If the answer is "yes," the process may proceed to step 2206 to transmit the physiological status information to the subject or a user other than the subject including, for example, a family member, a healthcare provider, a care provider, or the like, or a combination thereof. As used herein, such a user may also be referred to as a related member. Merely by way of example, while the related member receives the physiological status information indicating a health problem, a rescue or an assistance may be timely implemented. As another example, if the physiological status information indicates a genetic disease, a further pre-warning prompt may be sent to the related member having a family relationship with the subject to remind that there is a high risk of having the same genetic disease. In some embodiments, different pre-warning prompts with different levels may be sent to different members. For example, if the physiological status information of a father indicates that he may have a genetic disease, his son may receive a high-level pre-warning that he may suffer from the same disease, while a collateral relative may receive a low-level pre-warning.

If the answer is "No," the process may proceed to step 2207. No treatment may be performed regarding the physiological status information and the whole process may end. In some embodiments, while a request from a related member to visit the physiological status information of the subject is received, the physiological status information may be transmitted to the related member that has an access privilege.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure. In addition, the term "logic" is representative of hardware, firmware, software (or any combination thereof) to perform one or more functions. For instance, examples of "hardware" include, but are not limited to, an integrated circuit, a finite state machine, or even combinatorial logic. The integrated circuit may take the form of a processor such as a microprocessor, an application specific integrated circuit, a digital signal processor, a micro-controller, or the like.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "unit," "module," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device. In addition, the financial management system disclosed herein may be implemented as a firmware, firmware/software combination, firmware/hardware combination, or a hardware/firmware/software combination.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

We claim:

1. A device configured for monitoring blood pressure information of a subject, comprising:
   memory storing instructions; and
   at least one processor that executes the instructions to perform operations comprising:
   receiving an electrocardiograph (ECG) signal and a pulse related signal of a subject, wherein the ECG signal is acquired by an electric sensor, the electric sensor including an electrode, wherein the electrode comprises a flexible conductive layer, a gluing layer, and a metal button configured to connect the conductive layer and the gluing layer;
   generating a blood pressure of the subject based on the ECG signal and the pulse related signal;
   analyzing the blood pressure according to an analysis model, the analysis model being a function of a dependent variable and an independent variable and constructed based on a data mining process;
   generating a physiological analysis result of the blood pressure;
   providing a recommendation based on the physiological analysis result of the blood pressure; and
   transmitting, via a network, the recommendation to a terminal device associated with a related member with the subject;
   wherein the terminal device further comprises:
   an interaction unit;
   an identity verification unit; and
   a data generation unit, wherein the data generation unit is configured to receive and process the ECG and pulse signal of a subject, and further comprises:
   a pretreatment unit configured to pretreat the ECG and pulse signal;
   a recognition unit configured to analyze a feature of the ECG and pulse signal;
   a calculation unit configured to perform a calculation based on the feature from the recognition unit; and
   a calibration unit.

2. The device of claim 1, wherein the receiving the ECG signal and the pulse related signal comprises communicating with at least one physiological sensor configured to be located on at least one location on the body of the subject.

3. The device of claim 2, wherein the at least one physiological sensor comprises the electric sensor configured to acquire the ECG signal and an optical sensor configured to acquire the pulse related signal.

4. The device of claim 3, wherein the flexible conductive layer comprises a first opening through the flexible conductive layer and the gluing layer comprises a second opening through the gluing layer,
   and wherein the first opening corresponds to the second opening, and the metal button is fixed in the first opening and the second opening, and in contact with the flexible conductive layer.

5. The device of claim 2, wherein the location comprises at least one location selected from the head, the neck, the chest, the abdomen, the upper arm, the wrist, the waist, the upper leg, the knee, or the ankle of the subject.

6. The device of claim 1, wherein the physiological analysis result comprises a health condition evaluation indicating a health issue and the recommendation comprises a health tip or a medical guide.

7. The device of claim 6, wherein the health condition evaluation comprises a change of the blood pressure with time, a difference between the blood pressure and a reference blood pressure, or an abnormality associated with the blood pressure.

8. The device of claim 1, wherein the dependent variable comprises at least one of health condition, a prediction or the recommendation, and the independent variable comprises at least one of physiological signals, information of a subject, health related information, environmental information, history data, or statistical information.

9. The device of claim 1, wherein the operations further comprise:
verifying an identify of the related member; and
allowing an access privilege to the related member.

10. The device of claim 1, wherein
the gluing layer includes a first portion and a second portion, the first portion and the second portion are stuck together to fix the electrode along a body location of the subject; and
the electrode further includes a silicone placed protruded from a surface of the gluing layer.

11. A method implemented on at least one processor, a storage, and a communication platform connected to a network, the method comprising:
receiving an electrocardiograph (ECG) signal and a pulse related signal of a subject, wherein the ECG signal is acquired by an electric sensor, the electric sensor including an electrode, wherein the electrode comprises a flexible conductive layer, a gluing layer, and a metal button configured to connect the conductive layer and the gluing layer;
generating a blood pressure of the subject based on the ECG signal and the pulse related signal;
analyzing the blood pressure according to an analysis model, the analysis model being a function of a dependent variable and an independent variable and constructed based on a data mining process;
generating a physiological analysis result of the blood pressure;
providing a recommendation based on the physiological analysis result of the blood pressure; and
transmitting, via a network, the recommendation to a terminal device associated with a related member with the subject;
wherein the terminal device further comprises:
an interaction unit;
an identity verification unit; and
a data generation unit, wherein the data generation unit is configured to receive and process the ECG and pulse signal of a subject, and further comprises:
a pretreatment unit configured to pretreat the ECG and pulse signal;
a recognition unit configured to analyze a feature of the ECG and pulse signal;
a calculation unit configured to perform a calculation based on the feature from the recognition unit; and
a calibration unit.

12. The method of claim 11, wherein the receiving the ECG signal and the pulse related signal comprises communicating with at least one physiological sensor configured to be located on at least one location on the body of the subject.

13. The method of claim 12, wherein the at least one physiological sensor comprises the electric sensor configured to acquire the ECG signal and an optical sensor configured to acquire the pulse related signal.

14. The method of claim 11, wherein the flexible conductive layer comprises a first opening through the flexible conductive layer and the gluing layer comprises a second opening through the gluing layer,
and wherein the first opening corresponds to the second opening, and the metal button is fixed in the first opening and the second opening, and in contact with the flexible conductive layer.

15. The method of claim 12, wherein the location comprises at least one location selected from the head, the neck, the chest, the abdomen, the upper arm, the wrist, the waist, the upper leg, the knee, or the ankle of the subject.

16. The method of claim 11, wherein the physiological analysis result comprises a health condition evaluation indicating a health issue and the recommendation comprises a health tip or a medical guide.

17. The method of claim 16, wherein the health condition evaluation comprises a change of the blood pressure with time, a difference between the blood pressure and a reference blood pressure, or an abnormality associated with the blood pressure.

18. The method of claim 11, wherein the dependent variable comprises at least one of health condition, a prediction or the recommendation, and the independent variable comprises at least one of physiological signals, information of a subject, health related information, environmental information, history data, or statistical information.

19. The method of claim 11, further comprising:
verifying an identify of the related member; and
providing an access privilege to the related member.

20. The method of claim 11, wherein
the gluing layer includes a first portion and a second portion, the first portion and the second portion are stuck together to fix the electrode along a body location of the subject; and
the electrode further includes a silicone placed protruded from a surface of the gluing layer.

* * * * *